(12) United States Patent
Ali et al.

(10) Patent No.: US 10,011,615 B2
(45) Date of Patent: Jul. 3, 2018

(54) HETEROBICYCLO-SUBSTITUTED [1,2,4]TRIAZOLO[1,5-C]QUINAZOLIN-5-AMINE COMPOUNDS WITH A2A ANATAGONIST PROPERTIES

(71) Applicant: Merck Sharp & Dohme Corp., Rahway, NJ (US)

(72) Inventors: Amjad Ali, Freehold, NJ (US); Michael Man-Chu Lo, Bedminster, NJ (US); Yeon-Hee Lim, Piscataway, NJ (US); Andrew Stamford, Chatham, NJ (US); Rongze Kuang, Green Brook, NJ (US); Paul Tempest, Shanghai (CN); Younong Yu, East Brunswick, NJ (US); Xianhai Huang, Warren, NJ (US); Timothy J. Henderson, New Providence, NJ (US); Jae-Hun Kim, Scotch Plains, NJ (US); Christopher Boyce, Flemington, NJ (US); Pauline Ting, New Providence, NJ (US); Junying Zheng, New Providence, NJ (US); Edward Metzger, Somerset, NJ (US); Nicolas Zorn, Durmenach (FR); Dong Xiao, Warren, NJ (US); Gioconda V. Gallo, Summit, NJ (US); Walter Won, San Carlos, CA (US); Heping Wu, Edison, NJ (US); Qiaolin Deng, Edison, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/423,238

(22) Filed: Feb. 2, 2017

(65) Prior Publication Data
US 2017/0197991 A1    Jul. 13, 2017

Related U.S. Application Data

(63) Continuation of application No. 14/655,648, filed as application No. PCT/US2013/076781 on Feb. 20, 2013, now Pat. No. 9,708,347.

(30) Foreign Application Priority Data

Dec. 28, 2012   (WO) ............... PCT/CN2012/087865
Jun. 6, 2013    (WO) ............... PCT/CN2013/076853

(51) Int. Cl.
    *A01N 43/00*     (2006.01)
    *A01N 43/46*     (2006.01)
    *C07D 519/00*    (2006.01)
    *C07D 487/04*    (2006.01)

(52) U.S. Cl.
    CPC ......... *C07D 519/00* (2013.01); *C07D 487/04* (2013.01)

(58) Field of Classification Search
    CPC ........ A61K 47/14; A61K 47/32; A61K 47/38; A61K 9/0053; A61K 9/0056; A61K 9/006
    USPC ........................................................ 514/215
    See application file for complete search history.

(56) References Cited

U.S. PATENT DOCUMENTS

| 4,713,383 A | 12/1987 | Francis et al. |
| 5,571,775 A | 11/1996 | Van Heertum et al. |
| 5,736,564 A | 4/1998  | Elliott et al. |
| 5,929,106 A | 7/1999  | Elliott et al. |
| 6,630,475 B2 | 10/2003 | Neustadt et al. |
| 7,572,802 B2 | 8/2009  | Boyle et al. |
| 7,713,985 B2 | 5/2010  | Clasby et al. |
| 8,435,994 B2 | 5/2013  | Harris et al. |
| 2006/0135508 A1 | 6/2006 | Villa et al. |
| 2009/0029967 A1 | 1/2009 | Grzelak et al. |

(Continued)

FOREIGN PATENT DOCUMENTS

| EP | 0181282 | 5/1986 |
| EP | 0666079 | 8/1995 |

(Continued)

OTHER PUBLICATIONS

International Search Report-dated May 13, 2014.
El-Hashash et al, The Reactivity of 2-Ethoxy-4-Chloroquinazoline and Its Use in Synthesis of Novel Quinazoline Derivatives, Organic Chemistry International, 2011, 1-7.

*Primary Examiner* — Jean P Cornet
(74) *Attorney, Agent, or Firm* — H. Eric Fischer; John C. Todaro

(57) ABSTRACT

Disclosed are compounds of Formula G1:

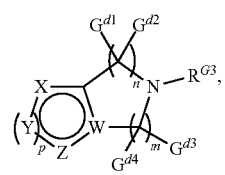

Formula GI where "$R^{G3}$", "$R^{d1}$" to "$R^{d4}$", "n", "m", "p", "W", "X", "Y", and "Z" are defined herein, which compounds are antagonists of $A_{2A}$ receptor. Disclosed herein also are uses of the compounds described herein as antagonists of the A2A receptor in the potential treatment or prevention of neurological disorders and diseases in which $A_{2A}$ receptors are involved. Disclosed herein also are pharmaceutical compositions comprising these compounds and uses of these pharmaceutical compositions.

14 Claims, No Drawings

(56) References Cited

U.S. PATENT DOCUMENTS

| | | |
|---|---|---|
| 2009/0062253 A1 | 3/2009 | Gahman et al. |
| 2012/0232086 A1 | 9/2012 | Harris et al. |
| 2016/0194330 A1 | 7/2016 | Ali et al. |

FOREIGN PATENT DOCUMENTS

| | | |
|---|---|---|
| WO | WO2001099264 | 12/2001 |
| WO | WO02055083 | 7/2002 |
| WO | WO2004094431 | 11/2004 |
| WO | WO2010084425 | 7/2010 |
| WO | WO20120135084 | 10/2012 |

HETEROBICYCLO-SUBSTITUTED [1,2,4]TRIAZOLO[1,5-C]QUINAZOLIN-5-AMINE COMPOUNDS WITH A2A ANATAGONIST PROPERTIES

CROSS-REFERENCE TO RELATED APPLICATIONS

This application is a Continuation Application of, and claims the priority of, U.S. patent application Ser. No. 14/655,648, which was filed pursuant to 35 U.S.C. § 371 on Jun. 25, 2015 from PCT Application No. PCT/US2013/076781, filed Dec. 20, 2013, which in turn claims the priority of international applications nos. PCT/CN2012/087865, filed Dec. 28, 2012 and PCT/CN2013/076853 filed on Jun. 6, 2013, each of which applications are incorporated herein by reference.

BACKGROUND OF THE INVENTION

Adenosine is known to be an endogenous modulator of a number of physiological functions. At the cardiovascular system level, adenosine is a strong vasodilator and a cardiac depressor. On the central nervous system, adenosine induces sedative, anxiolytic and antiepileptic effects. On the respiratory system, adenosine induces bronchoconstriction. At the kidney level, it exerts a biphasic action, inducing vasoconstriction at low concentrations and vasodilation at high doses. Adenosine acts as a lipolysis inhibitor on fat cells and as an anti-aggregant on platelets.

Adenosine action is mediated by the interaction with different membrane specific receptors which belong to the family of receptors coupled with G proteins. Biochemical and pharmacological studies, together with advances in molecular biology, have allowed the identification of at least four subtypes of adenosine receptors: $A_1$, $A_{2A}$, $A_{2b}$ and $A_3$. $A_1$ and $A_3$ are high-affinity, inhibiting the activity of the enzyme adenylate cyclase, and $A_{2A}$ and $A_{2b}$ are low-affinity, stimulating the activity of the same enzyme.

Analogs of adenosine able to interact as antagonists with the $A_1$, $A_{2A}$, $A_{2b}$ and $A_3$ receptors have also been identified. Selective antagonists for the $A_{2A}$ receptor are of pharmacological interest because of their reduced level of side effects. In the central nervous system, $A_{2A}$ antagonists can have antidepressant properties and stimulate cognitive functions. Moreover, data has shown that $A_{2A}$ receptors are present in high density in the basal ganglia, known to be important in the control of movement. Hence, $A_{2A}$ antagonists can improve motor impairment due to neurodegenerative diseases, for example, Parkinson's disease, senile dementia as in Alzheimer's disease, and psychoses of organic origin.

Some xanthine-related compounds have been found to be $A_1$ receptor selective antagonists, and xanthine and non-xanthine compounds have been found to have high $A_{2A}$ affinity with varying degrees of $A_{2A}$ vs. $A_1$ selectivity. Triazolo-pyrimidine adenosine $A_{2A}$ receptor antagonists with different substitution at the 7-position have been disclosed previously, for example in PCT International Application Publication Nos. WO 95/01356; U.S. Pat. No. 5,565,460; WO 97/05138; and WO 98/52568.

Parkinson's disease is characterized by progressive degeneration of the nigrostriatal dopaminergic pathway. The subsequent reduction in striatal dopamine levels is responsible for motor symptoms associated with Parkinson's disease, e.g., the loss of fine motor control or motor impairment manifested in those suffering from the disease. Current methodologies for alleviating motor symptoms associated with Parkinson's disease seek to replace dopamine either within the presynaptic terminal, for example, by administration of L-Dopa, directly through stimulation of the postsynaptic $D_2$ receptors, or by inhibiting metabolism, for example, by administration of monoamine oxidase type B (MAO-B) or catechol-O-methyltransferase (COMT). Long term use of such therapies is often associated with adverse events. For example, long term therapy with L-Dopa (currently the standard of care) is often associated with adverse events (e.g. motor complications), for example, "wearing-off", "random on-off" oscillations, or dyskinesia. These motor complications arising from therapy administered to manage Parkinson's disease often become progressively more severe with continued treatment.

As mentioned above, $A_{2A}$ receptors are present in high density in the basal ganglia and are known to be important in the control of fine motor movement. Highly selective $A_{2A}$ antagonists have demonstrated their efficacy in reducing motor symptoms associated with neurodegenerative diseases. Accordingly, compounds which are $A_{2A}$ receptor antagonists are believed to be useful in alleviating motor symptoms associated with Parkinson's disease. For example, U.S. Pat. No. 6,630,475 to Neustadt et al. (the '475 patent) describes the preparation of the compound of Formula PI:

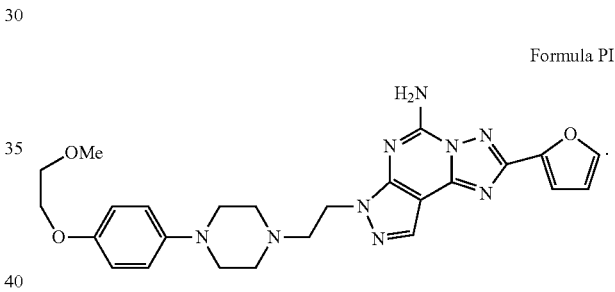

Formula PI

In the '475 patent example Schemes 1 to 5, along with preparative Schemes 1 to 4, show general methods of preparing compounds of Formula PI. The '475 patent describes also that the compound of Formula I can be prepared as a pharmaceutically acceptable salt which may be useful for treating Parkinson's disease.

The use of $A_{2A}$ receptor antagonists in the potential treatment of central nervous system diseases, in particular Parkinson's disease, and to pharmaceutical compositions comprising said compounds has elevated the need for potent, moderately lipophilic, brain penetrant inhibitors of the $A_{2A}$ receptor. Such compounds would provide an expansion of the arsenal of compounds which are believed to have value in the treatment of central nervous system disorders, in particular treating or managing the progression of such diseases, for example, but not limited to, Parkinson's disease.

SUMMARY OF THE INVENTION

In one aspect, the invention provides one or more compounds, or a pharmaceutically acceptable salt thereof, believed to have utility as an $A_{2A}$-receptor antagonist that have the structure of Formula GI:

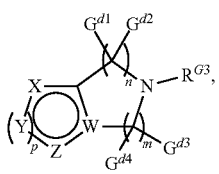

Formula GI wherein:

W is nitrogen or carbon;

m is 1, 2, 3, or 4; n is an integer of from 0 to 4, wherein the sum of n+m is at least 2 up to 4, and wherein, when W is N, m is at least 2;

$G^{d1}$ through $G^{d4}$ are independently hydrogen or a $C_{1-6}$-alkyl, and when alkyl is preferably methyl;

p is 1 or 2;

X, Y, and Z together with W and the carbon to which they are bonded form a 5 to 6 member aromatic or heteroaromatic moiety, and are independently:

(A) —($R^{G1}$)C=, wherein $R^{G1}$ is:
  i. hydrogen;
  ii. $C_{1-8}$-alkyl, optionally substituted with one or more halogen atoms;
  iii. —C(O)—$C_{1-8}$-alkyl;
  iv. —CN;
  v. —S—$C_{1-8}$-alkyl;
  vi. —O—$C_{1-6}$-alkyl;
  vii. —(CH2)$_{q1}$—(C=O)$_{q2}$—N($R^2$)$_2$, wherein "q¹" and "q²" are independently 0 or 1 and "$R^2$" is independently for each occurrence: (a) —H; (b) —$C_{1-6}$-alkyl; or (c) heteroaryl;
  viii. —C(O)O—$C_{1-8}$-alkyl;
  ix. halogen, wherein in some embodiments the halogen is F, Br or Cl, and is preferably F or Cl;
  x. a mono- or polycyclic heterocyclic moiety comprising up to 10 carbon atoms and one or more heteroatoms selected from N, S, or O, optionally substituted with one or more substituents which are, independently: (a) $C_{1-6}$-alkyl; morpholino; (b) phenyl (optionally substituted with halogen); (c) heteroaryl; or (d) halogen, and when the substituent is a monocyclic heterocyclic moiety, preferably it is independently:
    (1) morpholine, optionally substituted on any carbon atom thereof by one or more $C_{1-6}$-alkyl moieties;
    (2) piperazine, wherein the 4-N nitrogen is bonded to a substituent which is: (ai) H; (aii) $C_{1-6}$-alkyl (aiii) morpholino; (aiv) phenyl, optionally substituted with a halogen; (av) halogen; or (avi) heteroaryl;
    (3) piperidinyl, optionally substituted by $C_{1-6}$-alkyl or a morpholine moiety; or
    (4) pyrrolidine, optionally substituted with one or more halogen atoms, and when substituted with halogen, preferably the halogen is F;
  xi. aryl, which is optionally substituted with one or more substituents which are independently: (a) halogen; or (b) $C_{1-6}$-alkyl, which is optionally substituted with one or more halogen atoms, and when "$R^{G1}$" is selected to be an aryl moiety substituted with halogen, preferably the halogen is F;
  xii. —NH—C(O)—$R^3$, wherein $R^3$ is $C_{1-6}$-alkyl or heteroaryl; or
  xiii. heteroaryl, which is optionally substituted with $C_{1-6}$-alkyl, which alkyl moiety is optionally substituted with one or more substituents that are independently: (a) halogen; or (b) amino;

(B) >N$R^{G2}$, wherein $R^{G2}$ is: (i) H; (ii) $C_{1-8}$-alkyl; or (iii) an aromatic moiety of up to 10 carbon atoms, preferably aryl;

(C) —N=;

(D) —O—; or (E) —S—; and, $R^{G3}$ is a moiety of the structure:

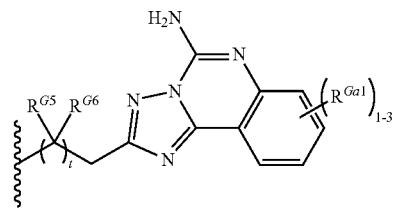

wherein:

t is 0, 1 or 2;

$R^{G5}$ and $R^{G6}$ are independently for each occurrence: (a) H; (b) $C_{1-10}$-alkyl, which is optionally substituted with one or more fluorine atoms; or (c) $R^{G5}$ and $R^{G6}$ taken together form a carbonyl moiety (C=O) with the proviso that if t=2, $R^{G5}$ and $R^{G6}$ are not selected to provide two adjacent carbonyl moieties; and, $R^{Ga1}$ is 1 to 3 substituents replacing an H on a ring carbon atom which are independently for each occurrence: (a) $C_{1-4}$-alkoxy, wherein the alkyl portion of the alkoxy moiety is optionally substituted with one or more halogen, and when halogen-substituted, preferably the halogen is F; (h) $C_{1-8}$-alkyl which is optionally substituted with one or more halogen atoms; c) halogen, preferably F or Cl; (d) —N($R^{G4}$)$_2$, wherein at least one of $R^{G4}$ is $C_{1-6}$alkyl and the other is H or $C_{1-6}$-alkyl; or (e) —CN.

i. In some embodiments, preferably $R^{G3}$ is a moiety of the structure:

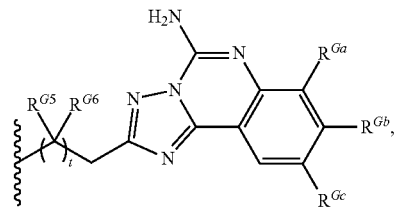

wherein:

t is 0, 1 or 2;

$R^{G5}$ and $R^{G6}$ are independently for each occurrence: (a) H; (b) $C_{1-10}$-alkyl which is optionally substituted with one or more fluorine atoms; or (c) $R^{G5}$ and $R^{G6}$ taken together form a carbonyl moiety (C=O) with the proviso that if t=2, $R^{G5}$ and $R^{G6}$ are not selected to provide two adjacent carbonyl moieties;

$R^{Ga}$, $R^{Gb}$, and $R^{Gc}$ are independently: (a) H; (b) $C_{1-4}$-alkoxy, wherein the alkyl portion of the alkoxy moiety is optionally substituted with one or more halogen, and when halogen-substituted, preferably the halogen is F; (c) C$_{1-8}$-alkyl, which is optionally substituted with one or more halogen atoms; (d) halogen, preferably F or Cl; (e) —N(R$^{G4}$)$_2$, wherein at least one of R$^{G4}$ is C$_{1-6}$-alkyl and the other is H or C$_{1-6}$-alkyl; or (f) —CN; with the proviso that at least one of R$^{Ga}$, R$^{Gb}$, or R$^{Gc}$ is H and at least one of R$^{Ga}$, R$^{Gb}$, or R$^{Gc}$ is not H.

In another aspect, the invention is a pharmaceutical formulation comprising at least one compound of Formula GI or a pharmaceutically acceptable salt thereof. In another aspect the invention is directed to the use of compounds, and pharmaceutical formulations thereof, in the potential treatment of movement disorders in which A$_{2A}$ receptors are involved.

In some aspects the present invention is the provision of a method of treating central nervous system disorders by administering to a subject in need thereof a therapeutic amount of at least one compound of Formula GI or a pharmaceutically acceptable salt thereof.

DETAILED DESCRIPTION OF THE INVENTION

As mentioned above, in one aspect the invention provides one or more compounds believed to have utility as an A$_{2A}$-receptor antagonist which have the structure of Formula GI.

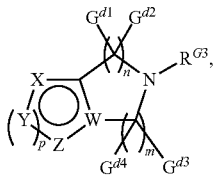

Formula GI or a pharmaceutically acceptable salt thereof, where p, m, n, W, X, Y, Z, R$^{Gd1}$ to R$^{Gd4}$, and R$^{G3}$ have been defined above.

In some embodiments, compounds of Formula GI preferably have the structure of Formula GII:

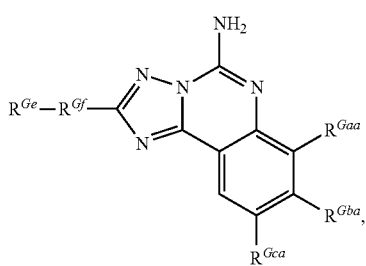

Formula GII or a salt thereof, wherein:
R$^{Gaa}$, R$^{Gba}$, and R$^{Gca}$ are independently for each occurrence:
(a) H; (b) C$_{1-6}$-alkyl; (c) C$_{1-4}$-alkoxy, which is optionally substituted with one or more fluorine atoms; (d) F; (e) Cl (f) Br; (g) CN; or (h) —N(R$^{G9}$)$_2$, wherein R$^{G9}$ is independently for each occurrence: (i) C$_{1-6}$-alkyl; or (ii) H; and wherein R$^{Gaa}$, R$^{Gba}$, and R$^{Gca}$ are selected such that at least one of R$^{Gaa}$, R$^{Gba}$, and R$^{Gca}$ is H and at least one of R$^{Gaa}$, R$^{Gba}$, and R$^{Gca}$ is not H;

R$^{Gf}$ is: (a) —CH$_2$—; (b) ethyl, which is optionally substituted with C$_{1-6}$-alkyl (optionally substituted with one or more fluorine atoms); (c) propyl; or (d) —C(O)—CH$_2$—; and, R$^{Ge}$ is a heteroaryl bicyclic moiety comprising up to 12 ring atoms of the structure:

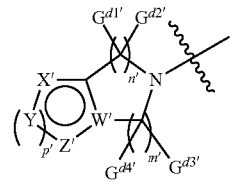

wherein
W' is nitrogen or carbon;
m' is 1, 2, 3, or 4;
n' is an integer of from 0 to 4, wherein the sum of n'+m' is at least 2 up to 4, and wherein, when W' is N, m' is at least 2;
p' is 1 or 2;
G$^{d1}$ through G$^{d4'}$ are independently H or a C$_{1-6}$-alkyl;
X', Y', and Z' together with W' and the carbon to which they are bonded form a 5 to 6 member aromatic or heteroaromatic moiety, and are independently:
(a) —(R$^{G1'}$)C═, wherein R$^{G1'}$ is:
  i. hydrogen;
  ii. C$_{1-8}$-alkyl, optionally substituted with one or more halogen atoms CF$_3$);
  iii. —C(O)—C$_{1-8}$-alkyl;
  iv. —CN;
  v. —S—C$_{1-8}$-alkyl;
  vi. —O—C$_{1-6}$-alkyl;
  vii. —(CH$_2$)$_q$—C(O)—N(R$^{2'}$)$_2$, wherein R$^{2'}$ is independently for each occurrence H, C$_{1-4}$-alkyl or pyridyl, and wherein q is 0 or 1;
  viii. —C(O)O—C$_{1-8}$-alkyl;
  ix. halogen, wherein in some embodiments the halogen is F, Br or Cl, and is preferably F or Cl;
  x. morpholine, optionally substituted on any carbon atom thereof by one or more C$_{1-6}$-alkyl moieties;
  xi. piperazine, wherein the 4-N nitrogen is bonded to a substituent which is: (ai) H; (aii) C$_{1-6}$-alkyl; (aiii) morpholine; (aiv) phenyl, optionally substituted with a halogen; (av) halogen; or (avi) heteroaryl;
  xii. piperidinyl, optionally substituted by C$_{1-6}$-alkyl or a morpholine moiety; or
  xiii. pyrrolidine, optionally substituted with one or more halogen atoms, and when substituted with halogen, preferably the halogen is F;
  xiv. phenyl, which is optionally substituted with one or more halogen atoms or C$_{1-6}$-alkyl (which optionally substituted with one or more halogen atoms), and when the aryl is substituted with halogen, preferably the halogen is F;
  xv. —NH—C(O)—R$^{3'}$, wherein R$^{3'}$ is C$_{1-4}$-alkyl or pyridinyl;
  xvi. heteroaryl, which is optionally substituted with CF$_3$, C$_{1-6}$-alkyl or amino; or
  xvii. —N(R$^{4'}$)$_2$, wherein R$^{4'}$ is independently for each occurrence H or C$_{1-6}$-alkyl;
(b) >NR$^{G2'}$, wherein R$^{G2'}$ is: (i) H; (ii) C$_{1-8}$-alkyl; or (iii) an aromatic moiety of up to 10 carbon atoms;

(c) —N═;
(d) —O—; or
(e) —S—.

In some embodiments, $R^{Gaa}$ is preferably methoxy and $R^{Gba}$ and $R^{Gca}$ are both H.

In some embodiments, in compounds of Formula GII, $R^{Ge}$ is preferably a moiety of Formula $R^{GeA}$:

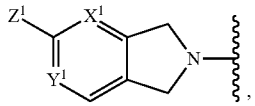

Formula $R^{GeA}$ where $X^1$, $Y^1$ and $Z^1$ are defined in Table I below:

TABLE I

| $X^1$ | $Y^1$ | $Z^1$ |
|---|---|---|
| N | C(H) | Cl |
| N | N | CF$_3$ |
| N | N | H |
| N | N | CH$_3$ |
| C(H) | C(H) | H |
| C(H) | C(H) | CF$_3$ |
| C(H) | C(H) | F |
| N | C(H) | H |
| C(H) | C(H) | F |
| C(F) | C(H) | H |
| C(F) | C(F) | H |

In some embodiments, in compounds of Formula GII, $R^{Ge}$ is preferably a moiety of Formula $R^{GeB}$:

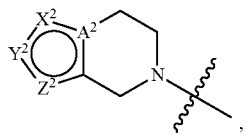

Formula $R^{GeB}$ where $A^2$, $X^2$, $Y^2$ and $Z^2$ are defined in Table II below:

TABLE II

| $X^2$ | $Y^2$ | $Z^2$ | $A^2$ |
|---|---|---|---|
| —C(—S—CH$_3$)═ | —N═ | —N═ | N |
| —C(—C(O)—NH—propyl)═ | —N═ | —N═ | N |
| —C(Br)═ | —N═ | —N═ | N |
| —C(C(O)—O—ethyl)═ | —N═ | —N═ | N |
| —N(cyclopropyl)— | —C(H)═ | —N═ | C═ |
| —C(isopropyl)═ | —C(H)═ | —N═ | N |
| —C(—C(O)—cyclopropyl)═ | —N═ | —C(H)═ | N |
| —N═ | —N═ | —C(—CF$_3$)═ | N |
| —N═ | —N═ | —C(cyclopropyl)═ | N |
| —C(ethyl)═ | —C(H)═ | —N═ | N |
| —N═ | —N(H)— | —C(—CF$_3$)═ | C═ |
| —C(—CF$_3$)═ | —N═ | —N═ | N |
| —C(ethyl)═ | —N═ | —N═ | N |
| —N(CH$_3$)— | —C(H)══ | —N═ | C═ |
| —N(H)— | —C(H)═ | —N═ | C═ |
| —N(H)— | —C(CH$_3$)═ | —N═ | C═ |
| —N(H)— | —C(CF$_3$)═ | —N═ | C═ |
| —C(isopropyl)═ | —N(H)— | —N═ | C═ |
| —N═ | —C(H)═ | —C(CF$_3$)═ | N |
| —C(—CF$_3$)═ | —N(H)— | —N═ | C═ |
| —C(H)═ | —N═ | —C(CF$_3$)═ | N |
| —C(ethyl)═ | —N═ | —N═ | N |

In some embodiments, in compounds of Formula GII, $R^{Ge}$ is preferably a moiety of Formula $R^{GeC}$:

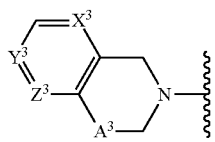

Formula $R^{GeC}$ where X, $Y^3$, $Z^3$ and $A^3$ are defined in Table III below:

TABLE III

| $X^3$ | $Y^3$ | $Z^3$ | $A^3$ |
|---|---|---|---|
| N | C(Br) | C(H) | CH$_2$ |
| C(H) | C(F) | C(H) | CH$_2$ |
| N | C(H) | C(H) | CH$_2$ |
| C(H) | C(—OCH$_3$) | C(H) | CH$_2$ |
| N | N | C(H) | CH$_2$ |
| N | N | N | CH$_2$ |
| C(H) | C(H) | C(H) | C(CH$_3$)$_2$ |
| N | C(H) | C(—Br) | CH$_2$ |
| N | C(H) | 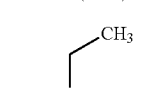 | CH$_2$ |
| N | C(H) | 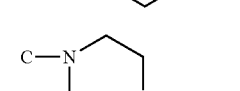 | CH$_2$ |
| N | C(H) | 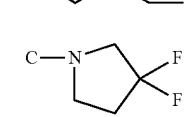 | CH$_2$ |
| C(H) | C(H) | C(H) | CH$_2$ |
| C(H) | C(CN) | C(H) | CH$_2$ |

In some embodiments, in compounds of Formula GII, $R^{Ge}$ preferably a moiety of Formula $R^{GeD}$:

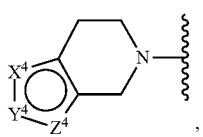

Formula $R^{GeD}$ where $X^4$, $Y^4$ and $Z^4$ are defined in Table IV below:

TABLE IV

| $X^4$ | $Y^4$ | $Z^4$ |
|---|---|---|
| —N═ | —O— | —C(CF$_3$)═ |
| —C(—CN)═ | —C(—cyclopropyl)═ | —S— |
| —S— | —C(CH$_3$)═ | —N═ |
| —S— | —C(CH$_3$)═ | —N═ |
| —O— | —C(CH$_3$)═ | —N═ |
| —N═ | —C(CH$_3$)═ | —O— |
| —N═ | —C(CH$_3$)═ | —S— |
| —N═ | —C(—isopropyl)═ | —S— |
| —N═ | —C(—isopropyl)═ | —O— |
| —O— | —N═ | —C(H)═ |
| —S— | —C(H)═ | —C(H)═ |
| —N═ | —C(H)═ | —S— |

TABLE IV-continued

| $X^4$ | $Y^4$ | $Z^4$ |
|---|---|---|
| —S— | —C(H)= | —N= |
| —N= | —C(H)= | —O— |
| —N= | —C(CHF$_2$)= | —O— |
| —N= | —C(CH$_2$OCH$_3$)= | —O— |

In some embodiments, in compounds of Formula GII, $R^{Ge}$ is preferably a moiety of Formula $R^{GeE}$:

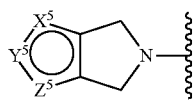

Formula $R^{GeE}$ where $X^5$, $Y^5$ and $Z^5$ are defined in Table V below:

TABLE V

| $X^5$ | $Y^5$ | $Z^5$ |
|---|---|---|
| —S— | —C(CH$_3$)= | —N= |
| —N= | —C(—phenyl)= | —NH— |
| —NH— | —N= | —C(—phenyl)= |
| —C(H)= | —N= | —NH— |
| —C(H)= | —N= | —N(CH$_3$)— |
| —N= | —C(—isopropyl)= | —S— |
| —N= | —C(CH$_3$)= | —S— |
| —N= | —C(CH$_3$)= | —O— |
| —N= | —C(—cyclopropyl)= | —S— |
| —S— | —C(—ethyl)= | —N= |
| —O— | —C(CH$_3$)= | —N= |
| —N= | —C(—cyclopropyl)= | —O— |

In some embodiments, in compounds of Formula GII, $R^{Ge}$ is preferably the following moiety:

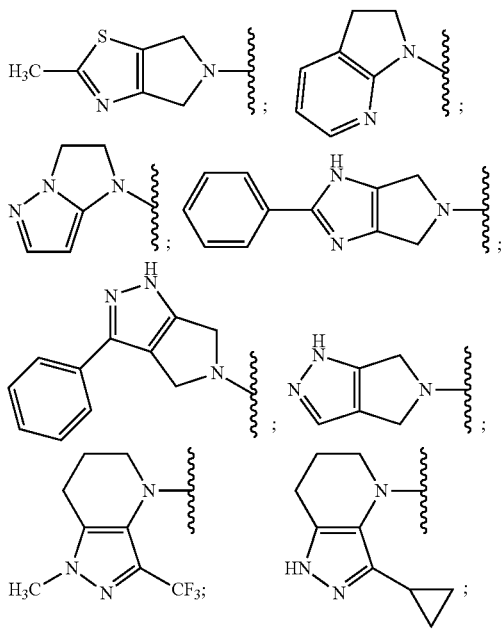

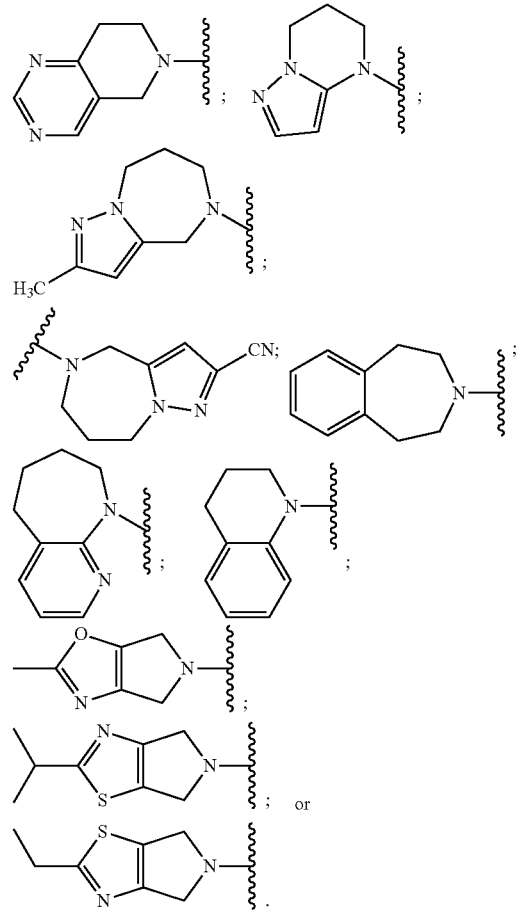

In some embodiments $R^{Gf}$ is preferably —CH$_2$—
In some embodiments $R^{Gf}$ is preferably —(CH$_2$)$_2$—.
In some embodiments, preferably compounds of the invention have the structure of GIIa:

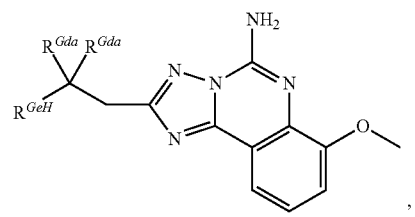

wherein:
$R^{Gda}$ is, independently for each occurrence: (a) H; (b) methyl; or (c) ethyl; and
$R^{Ge}$ is:

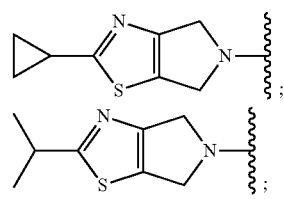

-continued

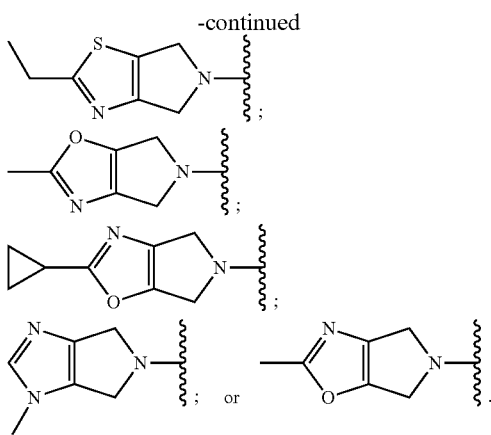

In some embodiments R$^{Gf}$ is preferably —CH(CH$_3$)—CH$_2$—.

In some embodiments a compound of the invention is:
7-methoxy-2-(2-(3-(methylthio)-5,6-dihydro[1,2,4]triazolo[4,3-a]pyrazin-7(8H)-yl)ethyl)-[1,2,4]triazolo[1,5-c]quinazolin-5-amine;
7-(2-(5-amino-7-methoxy-[1,2,4]triazolo[1,5-c]quinazolin-2-yl)ethyl)-N-tert-butyl-5,6,7,8-tetrahydro-[1,2,4]triazolo[4,3-a]pyrazine-3-carboxamide;
2-(2-(3-bromo-5,6-dihydro-[1,2,4]triazolo[4,3-a]pyrazin-7(8-H)-yl)ethyl)-7-methoxy-[1,2,4]triazolo[1,5-c]quinazolin-5-amine;
ethyl 7-(2-(5-amino-7-methoxy-[1,2,4]triazolo[1,5-c]quinazolin-2-yl)ethyl)-5,6,7,8-tetrahydro-[1,2,4]triazolo[4,3-a]pyrazine-3-carboxylate;
2-(2-(2-chloro-5H-pyrrolo[3,4-b]pyridin-6(7H)-yl)ethyl)-7-methoxy-[1,2,4]triazolo[1,5-c]quinazolin-5-amine;
2-(2-(4-bromo-5,6-dihydro-1,7-naphthyridin-7(8H)-yl)ethyl)-7-methoxy-[1,2,4]-triazolo[1,5-c]quinazolin-5-amine;
2-(2-(1-cyclopropyl-6,7-dihydro-1H-pyrazolo[4,3-c]pyridin-5(4H)-yl)ethyl)-7-methoxy-[1,2,4]triazolo[1,5-c]quinazolin-5-amine;
2-(2-(3-isopropyl-5,6-dihydroimidazo[1,5-a]pyrazin-7(8H)-yl)ethyl)-7-methoxy-[1,2,4]triazolo[1,5-c]quinazolin-5-amine;
7-methoxy-2-(2-(trifluoromethyl)-6,7-dihydroisoxazolo[4,3-]pyridin-5(4H)-yl)ethyl-[1,2,4]triazolo[1,5-c]quinazolin-5-amine;
(7-(2-(5-amino-7-methoxy-[1,2,4]triazolo[1,5-c]quinazolin-2-yl)ethyl)-5,6,7,8-tetrahydroimidazo[1,2-a]pyrazin-2-yl)(cyclopropyl)methanone;
7-methoxy-2-(2-(2-(trifluoromethyl)-5,6-dihydro-[1,2,4]triazolo[1,5-a]pyrazin-7(8H)-yl)ethyl)-[2,4]triazolo[1,5-c]quinazolin-5-amine;
2-(2-(2-cyclopropyl-5,6-dihydro-[1,2,4]triazolo[1,5-a]pyrazin-7(8H)-yl)ethyl-7-methoxy-[1,2,4]triazolo[1,5-c]quinazolin-5-amine;
2-(2-(3-ethyl-5,6-dihydroimidazo[1,5-a]pyrazin-7(8H)-yl)ethyl)-7-methoxy-[1,2,4]triazolo[1,5-c]quinazolin-5-amine;
7-methoxy-2-(2-(2-methyl-4H-pyrrolo[3,4-d]thiazol-5(6H)-yl)ethyl)-[1,2,4]triazolo[1,5-c]quinazolin-5-amine;
6-(2-(5-amino-7-methoxy-[1,2,4]triazolo[1,5-c]quinazolin-2-yl)ethyl)-2-cyclopropyl-4,5,6,7-tetrahydrothieno[2,3-c]pyridine-3-carbonitrile;
7-methoxy-2-(2-(2-(trifluoromethyl)-6,7-dihydro-3H-imidazo[4,5-c]pyridin-5(4H)-yl)ethyl)-[1,2,4]triazolo[1,5-c]quinazolin-5-amine;
7-methoxy-2-(2-(3-(trifluoromethyl)-5,6-dihydro-[1,2,4]triazolo[4,3-a]pyrazin-7(8H)-yl)ethyl)-[1,2,4]triazolo[1,5-c]quinazolin-5-amine;
7-methoxy-2-(2-(2-(trifluoromethyl)-5H-pyrrolo[3,4-d]pyrimidin-6(7H)-yl)ethyl)-[1,2,4]triazolo[1,5-c]quinazolin-5-amine;
2-(2(5H-pyrrolo[3,4-d]pyrimidin-6(7H)-yl)ethyl)-7-methoxy-[1,2,4]triazolo[1,5-c]quinazolin-5-amine;
2-(2-(7,8-dihydro-5H-pyrido[2,3-b]azepin-9(6H)-yl)ethyl)-7-methoxy-[1,2,4]triazolo[1,5-c]quinazolin-5-amine;
2-(2-(2,3-dihydro-1H-pyrrolo[2,3-b]pyridin-1-yl)ethyl)-7-methoxy-[1,2,4]triazolo[1,5-c]quinazolin-5-amine;
2-(2-(3-ethyl-5,6-dihydro-[1,2,4]triazolo[4,3-a]pyrazin-7(8H)-yl)ethyl)-7-methoxy-[1,2,4]triazolo[1,5-c]quinazolin-5-amine;
7-methoxy-2-(2-(2-methyl-5H-pyrrolo[3,4-d]pyrimidin-6(7H)-yl)ethyl)-[1,2,4]triazolo[1,5-c]quinazolin-5-amine;
2-(2-(isoindolin-2-yl)ethyl)-7-methoxy-[1,2,4]triazolo[1,5-c]quinazolin-5-amine;
7-methoxy-2-(2-(2-methyl-6,7-dihydrothiazolo[4,5-c]pyridin-5(4H)-yl)ethyl)-[1,2,4]triazolo[1,5-c]quinazolin-5-amine;
7-methoxy-2-(2-(2-(trifluoromethyl)-6,7-dihydrothiazolo[4,5-c]pyridin-5(4H)-yl)ethyl)-[1,2,4]triazolo[1,5-c]quinazolin-5-amine;
7-methoxy-2-(2-(2-methyl-6,7-dihydrooxazolo[4,5-c]pyridin-5(4H)-yl)ethyl)-[1,2,4]triazolo[1,5-c]quinazolin-5-amine;
7-methoxy-2-(2(2-methyl)-6,7-dihydrooxazolo[4,5-c]pyridin-5(4H)-yl)ethyl)-[1,2,4]triazolo[1,5-c]quinazolin-5-amine;
7-methoxy-2-(2-(2-methyl-6,7-dihydrothiazolo[5,4-c]pyridin-5(4H)-yl)ethyl)-[1,2,4]triazolo[1,5-c]quinazolin-5-amine;
2-(2-(2-cyclopropyl-6,7-dihydrothiazolo[5,4-c]pyridin-5(4H)-yl)ethyl)-7-methoxy-[1,2,4]triazolo[1,5-c]quinazolin-5-amine;
2-(2-(2-cyclopropyl-6,7-dihydrothiazolo[5,4-c]pyridin-5(4H)-yl)ethyl)-7-methoxy-[1,2,4]triazolo[1,5-c]quinazolin-5-amine;
7-methoxy-2-(2-(1-methyl-3-(trifluoromethyl)-6,7-dihydro-1H-pyrazolo[4,3-c]pyridin-5(4H)-yl)ethyl)-[1,2,4]triazolo[1,5-c]quinazolin-5-amine;
2-(2-(2,3-dihydro-1H-imidazo[1,2-b]pyrazol-1-yl)ethyl)-7-methoxy-[1,2,4]triazolo[1,5-c]quinazolin-5-amine;
7-methoxy-2-(2-(2-phenylpyrrolo[3,4-d]imidazol-5(1H,4H,6H)-yl)ethyl)-[1,2,4]triazolo[1,5-c]quinazolin-5-amine;
2-(2-(6,7-dihydroisoxazolo[4,5-c]pyridin-5(4H)-yl)ethyl)-7-methoxy-[1,2,4]triazolo[1,5-c]quinazolin-5-amine;
2-(2-(6,7-dihydro-1H-pyrazolo[4,3-c]pyridin-5(4H)-yl)ethyl)-7-methoxy-[1,2,4]triazolo[1,5-c]quinazolin-5-amine;
7-methoxy-2-(2-(3-methyl-6,7-dihydro-1H-pyrazolo[4,3-c]pyridin-5(4H)-yl)ethyl)-[1,2,4]triazolo[1,5-c]quinazolin-5-amine;
7-methoxy-2-(2-(3-(trifluoromethyl)-6,7-dihydro-1H-pyrazolo[4,3-c]pyridin-5(4H)-yl)ethyl)-[1,2,4]triazolo[1,5-c]quinazolin-5-amine;
2-(2-(6,7-dihydrothieno[3,2-c]pyridin-5(4H)-yl)ethyl)-7-methoxy-[1,2,4]triazolo[1,5-c]quinazolin-5-amine;

2-(2-(3-cyclopropyl-4,5-dihydro-1H-pyrazolo[3,4-c]pyridin-6(7H)-yl)ethyl)-7-methoxy-[1,2,4]triazolo[1,5-c]quinazolin-5-amine;

7-methoxy-2-(2-(2-methyl-6,7-dihydropyrazolo[1,5-a]pyrazin-5(4H)-yl)ethyl)-[1,2,4]triazolo[1,5-c]quinazolin-5-amine;

7-methoxy-2-(2-(3-(trifluoromethyl)-4,5-dihydro-1H-pyrazolo[3,4-c]pyridin-6(7H)-yl)ethyl)-[1,2,4]triazolo[1,5-c]quinazolin-5-amine;

7-methoxy-2-(2-(1-methyl-3-(trifluoromethyl)-6,7-dihydro-1H-pyrazolo[4,3-b]pyridin-4(5H)-yl)ethyl)-[1,2,4]triazolo[1,5-c]quinazolin-5-amine;

2-(2-(6-fluoro-3,4-dihydroisoquinolin-2(1H)-yl)ethyl)-7-methoxy-[1,2,4]triazolo[1,5-c]quinazolin-5-amine;

2-(2-(5,6-dihydro-1,7-naphthyridin-7(8H)-yl)ethyl)-7-methoxy-[1,2,4]triazolo[1,5-c]quinazolin-5-amine;

7-methoxy-2-(2-(5-(trifluoromethyl)isoindolin-2-yl)ethyl)-[1,2,4]triazolo[1,5-c]quinazolin-5-amine;

2-(2-(5-fluoroisoindolin-2-yl)ethyl)-7-methoxy-[1,2,4]triazolo[1,5-c]quinazolin-5-amine;

2-(2-(5H-pyrrolo[3,4-b]pyridin-6(7H)-yl)ethyl)-7-methoxy-[1,2,4]triazolo[1,5-c]quinazolin-5-amine;

7-methoxy-2-(2-(3-phenylpyrrolo[3,4-c]pyrazol-5(1H,4H,6H)-yl)ethyl)-[1,2,4]triazolo[1,5-c]quinazolin-5-amine;

7-methoxy-2-(2-(pyrrolo[3,4-c]pyrazol-5(1H,4H,6H)-yl)ethyl)-[1,2,4]triazolo[1,5-c]quinazolin-5-amine;

2-(2-(3-cyclopropyl-6,7-dihydro-1H-pyrazolo[4,3-b]pyridin-4(5H)-yl)ethyl)-7-methoxy-[1,2,4]triazolo[1,5-c]quinazolin-5-amine;

2-(2-(5,6-dihydropyrido[3,4-d]pyrimidin-7(8H)-yl)ethyl)-7-methoxy-[1,2,4]triazolo[1,5-c]quinazolin-5-amine;

2-(2-(7,8-dihydropyrido[4,3-d]pyrimidin-6(5H)-yl)ethyl)-7-methoxy-[1,2,4]triazolo[1,5-c]quinazolin-5-amine;

2-(2-(7,8-dihydropyrido[4,3-b]pyrazin-6(5H)-yl)ethyl)-7-methoxy-[1,2,4]triazolo[1,5-c]quinazolin-5-amine;

2-(2-(6,7-dihydrothiazolo[5,4-c]pyridin-5(4H)-yl)ethyl)-7-methoxy-[1,2,4]triazolo[1,5-c]quinazolin-5-amine;

2-(2-(6,7-dihydrothiazolo[4,5-c]pyridin-5(4H)-yl)ethyl)-7-methoxy-[1,2,4]triazolo[1,5-c]quinazolin-5-amine;

7-methoxy-2-(2-(2-(trifluoromethyl)-5,6-dihydroimidazo[1,2-a]pyrazin-7(8H)-yl)ethyl)-[1,2,4]triazolo[1,5-c]quinazolin-5-amine;

2-(2-(6,7-dihydropyrazolo[1,5-a]pyrimidin-4(5H)-yl)ethyl)-7-methoxy-[1,2,4]triazolo[1,5-c]quinazolin-5-amine;

7-methoxy-2-(2-(2-methyl-7,8-dihydro-4H-pyrazolo[1,5-a][1,4]diazepin-5(6H)-yl)ethyl)-[1,2,4]triazolo[1,5-c]quinazolin-5-amine;

5-(2-(5-amino-7-methoxy-[1,2,4]triazolo[1,5-c]quinazolin-2-yl)ethyl)-5,6,7,8-tetrahydro-4H-pyrazolo[1,5-a][1,4]diazepine-2-carbonitrile;

2-(2-(4,4-dimethyl-3,4-dihydroisoquinolin-2(1H)-yl)ethyl)-methoxy-[1,2,4]triazolo[5-c]quinazolin-5-amine;

7-methoxy-2-(2-(2-(4-methylpiperazin-1-yl)-5H-pyrrolo[3,4-b]pyridin-6(7H)-yl)ethyl)-[1,2,4]triazolo[1,5-c]quinazolin-5-amine;

7-methoxy-2-(2-(2-morpholino-5H-pyrrolo[3,4-b]pyridin-6(7H)-yl)-ethyl)-[1,2,4]triazolo[1,5-c]quinazolin-5-amine;

7-methoxy-2-(2-(2-(pyrrolidin-1-yl)-5H-pyrrolo[3,4-b]pyridin-6(7H)-yl)ethyl)-[1,2,4]triazolo[1,5-c]quinazolin-5-amine;

2-(2-(2-(4-ethylpiperazin-1-yl)-5H-pyrrolo[3,4-b]pyridin-6(7H)-yl)ethyl)-7-methoxy-[1,2,4]triazolo[1,5-c]quinazolin-5-amine;

2-(2-(2-(2,2-dimethylmorpholino)-5H-pyrrolo[3,4-b]pyridin-6(7H)-yl)ethyl)-7-methoxy-[1,2,4]triazolo[1,5-c]quinazolin-5-amine;

2-(2-(2-((2S,6R)-2,6-dimethylmorpholino)-5H-pyrrolo[3,4-b]pyridin-6(7H)-yl)ethyl)-7-methoxy-[1,2,4]triazolo[1,5-c]quinazolin-5-amine;

2-(2-(2-(4-(cyclopropylmethyl)piperazin-1-yl)-5H-pyrrolo[3,4-b]pyridin-6(7H)-yl)ethyl)-7-methoxy-[1,2,4]triazolo[1,5-c]quinazolin-5-amine;

2-(2-(2-(4-(4-fluorophenyl)piperazin-1-yl)-5H-pyrrolo[3,4-b]pyridin-6(7H)-yl)ethyl)-7-methoxy-[1,2,4]triazolo[1,5-c]quinazolin-5-amine;

7-methoxy-2-(2-(2-(4-morpholinopiperidin-1-yl)-5H-pyrrolo[3,4-b]pyridin-6(7H)-yl)ethyl)-[1,2,4]triazolo[1,5-c]quinazolin-5-amine;

2-(2-(4-(4-ethylpiperazin-1-yl)-5,6-dihydro-1,7-naphthyridin-7(8H)-yl)ethyl)-7-methoxy-[1,2,4]triazolo[1,5-c]quinazolin-5-amine;

2-(2-(4-(diethylamino)-5,6-dihydro-1,7-naphthyridin-7(8H)-yl)ethyl)-7-methoxy-[1,2,4]triazolo[1,5-c]quinazolin-5-amine;

2-(2-(4-(3,3-difluoropyrrolidin-1-yl)-5,6-dihydro-1,7-naphthyridin-7(8H)-yl)ethyl)-7-methoxy-[1,2,4]triazolo[1,5-c]quinazolin-5-amine;

2-(5-amino-7-methoxy-[1,2,4]triazolo[1,5-c]quinazolin-2-yl)-1-(5H-pyrrolo[3,4-b]pyridin-6(7H)-yl)ethanone;

2-(5-amino-7-methoxy-[1,2,4]triazolo[1,5-c]quinazolin-2-yl)-1-(4,5-dihydro-1H-benzo[d]azepin-3(2H)-yl)ethanone;

2-(2-(5H-pyrrolo[3,4-b]pyridin-6(7H)-yl)ethyl)-7-(fluoromethoxy)-[1,2,4]triazolo[1,5-c]quinazolin-5-amine;

7-chloro-2-(2-(5-fluoroisoindolin-2-yl)ethyl)-[1,2,4]triazolo[1,5-c]-quinazolin-5-amine;

7-chloro-2-(2-(3,4-dihydroquinolin-1(2H)-yl)ethyl)-[1,2,4]triazolo[1,5-c]quinazolin-5-amine;

2-[2-(5,7-dihydro-6H-pyrrolo[3,4-b]pyridin-6-yl)ethyl]-7-fluoro[1,2,4]triazolo[1,5-c]quinazolin-5-amine;

2-(2-(3,4-dihydroquinolin-1(2H)-yl)ethyl)-7-fluoro-[1,2,4]triazolo[1,5-c]quinazolin-5-amine;

7-fluoro-2-(2-(5-fluoroisoindolin-2-yl-ethyl)-[1,2,4]triazolo[1,5-c]quinazolin-5-amine;

2-(2-(3-ethyl-5,6-dihydro-[1,2,4]triazolo[4,3-a]pyrazin-7(8H)-yl)ethyl)-7-fluoro-[1,2,4]triazolo[1,5-c]quinazolin-5-amine;

2-(2-(3,4-dihydroisoquinolin-2(1H)-yl)ethyl)-7-fluoro-[1,2,4]triazolo[1,5-c]quinazolin-5-amine;

7-fluoro-2-(2-(2-(trifluoromethyl)-5H-pyrrolo[3,4-d]-6(7H)-yl)ethyl)-[1,2,4]triazolo[1,5-c]quinazolin-5-amine;

7-fluoro-2-(2-(4-fluoroisoindolin-2-yl)ethyl)-[1,2,4]triazolo[1,5-c]quinazolin-5-amine;

2-(2-(3,4-dihydroisoquinolin-2(1H)-yl)ethyl)-7-methyl-[1,2,4]triazolo[1,5-c]quinazolin-5-amine;

8-fluoro-2-(2-(5-fluoroisoindolin-2-yl)ethyl)-[1,2,4]triazolo[1,5-c]quinazolin-5-amine;

2-(2-(5H-pyrrolo[3,4-b]pyridin-6(7H)-yl)ethyl)-8-fluoro-[1,2,4]triazolo[1,5-c]quinazolin-5-amine;

2-(2-(3,4-dihydroisoquinolin-2(1H)-yl)ethyl)-8-fluoro-[1,2,4]triazolo[1,5-c]quinazolin-5-amine;

2-(2-(3,4-dihydroquinolin-1(2H)-yl)ethyl)-8-fluoro-[1,2,4]triazolo[1,5-c]quinazolin-5-amine;

2-(2-(3-ethyl-5,6-dihydro-[1,2,4]triazolo[4,3-a]pyrazin-7(8H)-yl)ethyl)-8-fluoro-[1,2,4]triazolo[1,5-c]quinazolin-5-amine;

8-fluoro-2-(2-(4-fluoroisoindolin-2-yl)ethyl)-[1,2,4]triazolo[1,5-c]quinazolin-5-amine;

2-(2-(5H-pyrrolo[3,4-b]pyridin-6(7H)-yl)ethyl)-7,8-dimethoxy-[1,2,4]triazolo[1,5-c]quinazolin-5-amine;

2-(2-(5H-pyrrolo[3,4-b]pyridin-6(7H)-yl)ethyl)-9-fluoro-7-methoxy-[1,2,4]triazolo[1,5-c]quinazolin-5-amine;

2-(2-(5H-pyrrolo[3,4-b]pyridin-6(7H)-yl)ethyl)-8,9-difluoro-[1,2,4]triazolo[1,5-c]quinazolin-5-amine;

2-(2-(5H-pyrrolo[3,4-b]pyridin-6(7H)-yl)ethyl)-7,9-difluoro-[1,2,4]triazolo[1,5-c]quinazolin-5-amine;

2-(3,3-difluoro-2-(5H-pyrrolo[3,4-b]pyridin-6(7H)-yl)propyl)-7-methoxy-[1,2,4]triazolo[1,5-c]quinazolin-5-amine;

(R)-2-(3,3-difluoro-2-(5H-pyrrolo[3,4-b]pyridin-6(7H)-yl)propyl)-7-methoxy-[1,2,4]triazolo[1,5-c]quinazolin-5-amine;

(S)-2-(3,3-difluoro-2-(5H-pyrrolo[3,4-b]pyridin-6(7H)-yl)propyl)-7-methoxy-[1,2,4]triazolo[1,5-c]quinazolin-5-amine;

2-(3-fluoro-2-(5H-pyrrolo[3,4-b]pyridin-6(7H)-yl)propyl)-7-methoxy-[1,2,4]triazolo[1,5-c]quinazolin-5-amine;

2-(2-(5H-pyrrolo[3,4-b]pyridin-6(7H)-yl)propyl)-7-methoxy-[1,2,4]triazolo[1,5-c]quinazolin-5-amine;

(S)-2-(2-(5H-pyrrolo[3,4-b]pyridin-6(7H)-yl)propyl)-7-methoxy-[1,2,4]triazolo[1,5-c]quinazolin-5-amine;

(R)-2-(2(5H-pyrrolo[3,4-b]pyridin-6(7H)-yl)propyl)-7-methoxy-[1,2,4]triazolo[1,5-c]quinazolin-5-amine;

7-methoxy-2-(3,3,3-trifluoro-2-(5H-pyrrolo[3,4-b]pyridin-6(7H)-yl)propyl)-[1,2,4]triazolo[1,5-c]quinazolin-5-amine;

(S)-7-methoxy-2-(3,3,3-trifluoro-2-(5H-pyrrolo[3,4-b]pyridin-6(7H)-yl)propyl)-[1,2,4]triazolo[1,5-c]quinazolin-5-amine;

(R)-7-methoxy-2-(3,3,3-trifluoro-2-(5H-pyrrolo[3,4-b]pyridin-6(7H)-yl)propyl)-[1,2,4]triazolo[1,5-c]quinazolin-5-amine;

2-(2-(5H-pyrrolo[3,4-b]pyridin-6(7H)-yl)butyl)-7-methoxy-[1,2,4]triazolo[1,5-c]quinazolin-5-amine;

(R)-2-(2-(5H-pyrrolo[3,4-]pyridin-6(7H)-yl)butyl)-7-methoxy-[1,2,4]triazolo[1,5-c]quinazolin-5-amine;

(S)-2-(2-(5H-pyrrolo[3,4-b]pyridin-6(7H)-yl)butyl)-7-methoxy-[1,2,4]triazolo[1,5-c]quinazolin-5-amine;

2-(2-(5-fluoroisoindolin-2-yl)propyl)-7-methoxy-[1,2,4]triazolo[1,5-c]quinazolin-5-amine;

2-(2-(5H-pyrrolo[3,4-b]pyridin-6(7H)-yl)pentyl-7-methoxy-[1,2,4]triazolo[1,5-c]quinazolin-5-amine;

7-methoxy-2-(2-(2-methyl-6,7-dihydrooxazolo[5,4-c]pyridin-5(4H)-yl)propyl)-[1,2,4]triazolo[1,5-c]quinazolin-5-amine;

2-((5-fluoroisoindolin-2-yl)methyl)-7-methoxy-[1,2,4]triazolo[1,5-c]quinazolin-5-amine;

2-((5H-pyrrolo[3,4-b]pyridin-6(7H)-yl)methyl)-7-methoxy-[1,2,4]triazolo[1,5-c]quinazolin-5-amine;

2-((3,4-dihydroquinolin-1(2H)-yl)methyl)-7-methoxy-[1,2,4]triazolo[1,5-c]quinazolin-5-amine;

2-((2H-benzo[b][1,4]oxazin-4(3H)-yl)methyl)-7-methoxy-[1,2,4]triazolo[1,5-c]quinazolin-5-amine;

2-((3,4-dihydroisoquinolin-2(1H)-yl)methyl)-7-methoxy-[1,2,4]triazolo[1,5-c]quinazolin-5-amine;

2-((5-amino-7-methoxy-[1,2,4]triazolo[1,5-c]quinazolin-2-yl)methyl)-1,2,3,4-tetrahydroisoquinoline-6-carbonitrile;

2-((5,6-dihydro-1,7-naphthyridin-7(8H)-yl)methyl)-7-methoxy-[1,2,4]triazolo[1,5-c]quinazolin-5-amine;

7-methoxy-2-((7-methoxy-4,5-dihydro-1H-benzo[d]azepin-3(2H)-yl)methyl)-[1,2,4]triazolo[1,5-c]quinazolin-5-amine;

2-((3,4-dihydro-2,7-naphthyridin-2(1H)-yl)methyl)-7-methoxy-[1,2,4]triazolo[1,5-c]quinazolin-5-amine;

7-methoxy-2-((8-((4-(pyridin-2-yl)piperazin-1-yl)methyl)-3,4-dihydroisoquinolin-2(1H)-yl)methyl)-[1,2,4]triazolo[1,5-c]quinazolin-5-amine;

7-methoxy-2-((5-(trifluoromethyl)isoindolin-2-yl)methyl)-[2,4]triazolo[1,5-c]quinazolin-5-amine;

7-methoxy-2-((2,3,1,5-tetrahydro-1H-benzo[b]azepin-1-yl)methyl)-[1,2,4]triazolo[1,5-c]quinazolin-5-amine;

7-methoxy-2-((3-(trifluoromethyl)-7,8-dihydro-1,6-naphthyridin-6(5H)-yl)methyl)-[1,2,4]triazolo[1,5-c]quinazolin-5-amine;

2-((6-fluoro-3,4-dihydroisoquinolin-2(1H)-yl)methyl)-7-methoxy-[1,2,4]triazolo[1,5-c]quinazolin-5-amine;

2-((4,5-dihydro-1H-benzo[d]azepin-3(2H)-yl)methyl)-7-methoxy-[1,2,4]triazolo[1,5-c]quinazolin-5-amine;

2-((4,5-dihydro-1H-benzo[c]azepin-2(3H)-yl)methyl)-7-methoxy-[1,2,4]triazolo[1,5-c]quinazolin-5-amine;

2-((3,4-dihydro-1,5-naphthyridin-1(2H)-yl)methyl)-7-methoxy-[1,2,4]triazolo[1,5-c]quinazolin-5-amine;

2-(3,4-dihydro-1,6-naphthyridin-1(2H)-yl)methyl)-7-methoxy-[1,2,4]triazolo[1,5-c]quinazolin-5-amine;

2-((3,4-dihydro-1,7-naphthyridin-1(2H)-yl)methyl)-7-methoxy-[1,2,4]triazolo[1,5-c]quinazolin-5-amine;

2-((7-chloro-4-methyl-2,3,4,5-tetrahydro-1H-benzo[e][1,4]diazepin-1-yl)methyl)-7-methoxy-[1,2,4]triazolo[1,5-c]quinazolin-5-amine;

2-((2-chloro-5H-pyrrolo[3,4b]-pyridin-6(7H)-yl-methyl-7-methoxy-[1,2,4]triazolo[1,5-c]quinazoline-5-amine;

7-methoxy-2-(3-(methylthio)-5,6-dihydro-[1,2,4]triazolo[4,3-a]pyrazin-7(8H)-yl)methyl)-[1,2,4]triazolo[1,5-c]quinazolin-5-amine;

ethyl 7-((5-amino-7-methoxy-[1,2,4]triazolo[1,5-c]quinazolin-2-yl)methyl)-5,6,7,8-tetrahydro-[1,2,4]triazolo[4,3-a]pyrazine-3-carboxylate;

2-((3-bromo-5,6-dihydro-[1,2,4]triazolo[4,3-a]pyrazin-7(8H)-yl)methyl)-7-methoxy-[1,2,4]triazolo[1,5-c]quinazolin-5-amine;

2-((5,6-dihydro-[1,2,4]triazolo[4,3-a]pyrazin-7(8H)-yl)methyl)-7-methoxy-[1,2,4]triazolo[1,5-c]quinazolin-5-amine;

2-((3-ethyl-5,6-dihydro-[1,2,4]triazolo[4,3-a]pyrazin-7(8H)-yl)methyl)-7-methoxy-[1,2,4]triazolo[1,5-c]quinazolin-5-amine;

7-((5-amino-7-methoxy-[1,2,4]triazolo[1,5-c]quinazolin-2-yl)methyl)-N-tert-butyl-5,6,7,8-tetrahydro-[1,2,4]triazolo[4,3-a]pyrazine-3-carboxamide;

7-methoxy-2-((3-methoxy-5,6-dihydro-[1,2,4]triazolo[4,3-a]pyrazin-7(8H)-yl)methyl)-[1,2,4]triazolo[1,5-c]quinazolin-5-amine;

2-((5,5-dimethyl-3-(trifluoromethyl)-5,6-dihydro-[1,2,4]triazolo[4,3-a]pyrazin-7(8H)-yl)methyl)-7-methoxy-[1,2,4]triazolo[1,5-c]quinazolin-5-amine;

2-((8,8-dimethyl-3-(trifluoromethyl)-5,6-dihydro-[1,2,4]triazolo[4,3-a]pyrazin-7(8H)-yl)methyl)-7-methoxy-[1,2,4]triazolo[1,5-c]quinazolin-5-amine;

2-((4-bromo-5,6-dihydro-1,7-naphthyridin-7(8H)-yl)methyl)-7-methoxy-[1,2,4]triazolo[1,5-c]quinazolin-5-amine;

2-((2-isopropyl-4H-pyrrolo[3,4-d]thiazol-5(6H)-yl)methyl)-7-methoxy-[1,2,4]triazolo[1,5-c]quinazolin-5-amine;

2-((7,8-dihydropyrido[4,3-b]pyrazin-6(5H)-yl)methyl)-7-methoxy-[1,2,4]triazolo[1,5-c]quinazolin-5-amine;

2-((5,6-dihydropyrido[3,4-d]pyrimidin-7(8H)-yl)
methyl)-7-methoxy-[1,2,4]triazolo[1,5-c]quinazolin-5-amine;
7-methoxy-2-((2-(trifluoromethyl)-5H-pyrrolo[3,4-d]pyrimidin-6(7H)-yl)methyl)-[1,2,4]triazolo[1,5-c]quinazolin-5-amine;
7-methoxy-2-((3-(trifluoromethyl)-5,6-dihydro-[1,2,4]triazolo[4,3-a]pyrazin-7(8H)-yl)methyl)-[1,2,4]triazolo[1,5-c]quinazolin-5-amine;
2-((2,3-dihydro-1H-pyrrolo[2,3-b]pyridin-1-yl)methyl)-7-methoxy-[1,2,4]triazolo[1,5-c]quinazolin-5-amine;
2-((5-bromo-2,3-dihydro-1H-pyrrolo[2,3-b]pyridin-1-yl)methyl)-7-methoxy-[1,2,4]triazolo[1,5-c]quinazolin-5-amine;
7-methoxy-2-((7-methyl-3,4-dihydro-1,8-naphthyridin-1(2H)-yl)methyl)-[1,2,4]triazolo[1,5-c]quinazolin-5-amine;
2-((7,8-dihydro-5H-pyrido[2,3-b]azepin-9(6H)-yl)methyl)-7-methoxy-[1,2,4]triazolo[1,5-c]quinazolin-5-amine;
2-((2,3-dihydro-1H-pyrrolo[2,3-b]pyridin-1-yl)methyl)-7-methoxy-[1,2,4]triazolo[1,5-c]quinazolin-5-amine;
2-((2-chloro-7,8-dihydro-5H-pyrido[2,3-b]azepin-9(6H)-yl)methyl)-7-methoxy-[1,2,4]triazolo[1,5-c]quinazolin-5-amine;
2-((3,4-dihydro-1,8-naphthyridin-1(2H)-yl)methyl)-7-methoxy-[1,2,4]triazolo[1,5-c]quinazolin-5-amine;
7-methoxy-2-((2-(pyridin-2-yl)-7,8-dihydro-5H-pyrido[2,3-b]azepin-9(6H)-yl)methyl)-[1,2,4]triazolo[1,5-c]quinazolin-5-amine;
2-((4,4-dimethyl-3,4-dihydroisoquinolin-2(1H)-yl)methyl)-7-methoxy-[1,2,4]triazolo[1,5-c]quinazolin-5-amine;
2-((5H-pyrrolo[3,4-b]pyridin-6(7H)-yl)methyl)-9-fluoro-7-methoxy-[1,2,4]triazolo[1,5-c]quinazoline-5-amine;
7-methoxy-2-((7-(pyrimidin-5-yl)-3,4-dihydroisoquinolin-2(1H)-yl)methyl)-[1,2,4]triazolo[1,5-c]quinazolin-5-amine;
N-(2-((5-amino-7-methoxy-[1,2,4]triazolo[1,5-c]quinazolin-2-yl)methyl)-1,2,3,4-tetrahydroisoquinolin-7-yl)picolinamide;
N-(2-((5-amino-7-methoxy-[1,2,4]triazolo[1,5-c]quinazolin-2-yl)methyl)-1,2,3,4-tetrahydroisoquinolin-7-yl)acetamide;
2-((7-(3,4-difluorophenyl)-3,4-dihydroisoquinolin-2(1H)-yl)methyl)-7-methoxy-[1,2,4]triazolo[1,5-c]quinazolin-5-amine;
7-methoxy-2-(2-(7-(pyrimidin-5-yl)-3,4-dihydroisoquinolin-2(1H)-ethyl)-[1,2,4]triazolo[1,5-c]quinazolin-5-amine;
2-(2-((5-amino-7-methoxy-[1,2,4]triazolo[1,5-c]quinazolin-2-yl)methyl)-1,2,3,4-tetrahydroisoquinolin-7-yl)-N-(pyridine-3-yl)acetamide;
7-methoxy-2-((5-(pyrimidin-5-yl)isoindolin-2-yl)methyl)-[1,2,4]triazolo[1,5-c]quinazolin-5-amine;
7-methoxy-2-((8-(pyrimidin-5-yl)-3,4-dihydroisoquinolin-2(1H)-yl)methyl)-[1,2,4]triazolo[1,5-c]quinazolin-5-amine;
7-methoxy-2-((7-(2-(trifluoromethyl)pyrimidin-5-yl)-3,4-dihydroisoquinolin-2(1H)-yl)methyl)-[1,2,4]triazolo[1,5-c]quinazolin-5-amine;
7-methoxy-2-((7-(1-methyl-1H-pyrazol-4-yl)-3,4-dihydroisoquinolin-2(1H)-yl)methyl)-[1,2,4]triazolo[1,5-c]quinazolin-5-amine;
7-methoxy-2-((7-(1-methyl-5-(trifluoromethyl)-1H-pyrazol-4-yl)-3,4-dihydroisoquinolin-2(1H)-yl)methyl)-[1,2,4]triazolo[1,5-c]quinazolin-5-amine;
7-methoxy-2-((7-(1-methyl-3-(trifluoromethyl)-1H-pyrazol-4-yl)-3,4-dihydroisoquinolin-2(1H)-yl)methyl)-[1,2,4]triazolo[1,5-c]quinazolin-5-amine;
7-methoxy-2-((7-(2-(trifluoromethyl)phenyl)-3,4-dihydroisoquinolin-2(1H)-yl)methyl)-[1,2,4]triazolo[1,5-c]quinazolin-5-amine;
2-((7-(2-amino-4-(trifluoromethyl)pyrimidin-5-yl)-3,4-dihydroisoquinolin-2(1H)-yl)methyl)-7-methoxy-[1,2,4]triazolo[1,5-c]quinazolin-5-amine;
7-methoxy-2-(2-(7-(2-(trifluoromethyl)pyrimidin-5-yl)-3,4-dihydroisoquinolin-2(1H)-yl)ethyl)-[1,2,4]triazolo[1,5-c]quinazolin-5-amine;
7-bromo-2-((5,6-dihydro-1,7-naphthyridin-7(8H)-yl)methyl)-[1,2,4]triazolo[1,5-c]quinazolin-5-amine;
2-((5H-pyrrolo[3,4-b]pyridin-6(7H)-yl)methyl)-7-bromo-[1,2,4]triazolo[1,5-c]quinazolin-5-amine;
5-amino-2-((5,6-dihydro-1,7-naphthyridin-7(8H)-yl)methyl)-[1,2,4]triazolo[1,5-c]quinazoline-7-carbonitrile;
2-((5H-pyrrolo[3,4-b]pyridin-6(7H)-yl)methyl)-5-amino-[1,2,4]triazolo[1,5-c]quinazoline-7-carbonitrile;
2-((5H-pyrrolo[3,4-b]pyridin-6(7H)-yl)methyl)-7-(methoxymethyl)-[1,2,4]triazolo[1,5-c]quinazolin-5-amine;
2-((5,6-dihydro-1,7-naphthyridin-7(8H)-yl)methyl)-7-(methoxymethyl)-[1,2,4]triazolo[1,5-c]quinazolin-5-amine;
2-((5H-pyrrolo[3,4-b]pyridin-6(7H)-yl)methyl)-7-methyl-[1,2,4]triazolo[1,5-c]quinazolin-5-amine;
2-((5,6-dihydro-1,7-naphthyridin-7(8H)-yl)methyl)-7-methyl-[1,2,4]triazolo[1,5-c]quinazolin-5-amine;
2-((5,6-dihydro-1,7-naphthyridin-7(8H)-yl)methyl)-7-(2-fluoroethoxy)-[1,2,4]triazolo[1,5-c]quinazolin-5-amine;
2-((5H-pyrrolo[3,4-b]pyridin-6(7H)-yl)methyl)-7-ethoxy-[1,2,4]triazolo[1,5-c]quinazolin-5-amine;
2-((5,6-dihydro-1,7-naphthyridin-7(8H)-yl)methyl)-7-ethoxy-[1,2,4]triazolo[1,5-c]quinazoline-5-amine;
2-((5,6-dihydro-1,7-naphthyridin-7(8H)-yl)methyl)-7-(fluoromethoxy)-[1,2,4]triazolo[1,5-c]quinazolin-5-amine;
(R)-7-methoxy-2-(2-(2-methyl-6,7-dihydrooxazolo[5,4-c]pyridin-5(4H)-yl)propyl)-[1,2,4]triazolo[1,5-c]quinazolin-5-amine;
(S)-7-methoxy-2-(2-(2-methyl-6,7-dihydrooxazolo[5,4-c]pyridin-5(4H)-yl)propyl)-[1,2,4]triazolo[1,5-c]quinazolin-5-amine;
7-methoxy-2-(2-(2-methyl-6,7-dihydrooxazolo[4,5-c]pyridin-5(4H)-yl)propyl)-[1,2,4]triazolo[1,5-c]quinazolin-5-amine;
(R)-7-methoxy-2-(2-(2-methyl-6,7-dihydrooxazolo[4,5-c]pyridin-5(4H)-yl)propyl)-[1,2,4]triazolo[1,5-c]quinazolin-5-amine;
(S)-7-methoxy-2-(2-(2-methyl-6,7-dihydrooxazolo[4,5-c]pyridin-5(4H)-yl)propyl)-[1,2,4]triazolo[1,5-c]quinazolin-5-amine;
(R)-7-methoxy-2-(2-(2-methyl-6,7-dihydrothiazolo[5,4-c]pyridin-5(4H)-yl)propyl)-[1,2,4]triazolo[1,5-c]quinazolin-5-amine;
(S)-7-methoxy-2-(2-(2-methyl-6,7-dihydrothiazolo[5,4-c]pyridin-5(4H)-yl)propyl)-[1,2,4]triazolo[1,5-c]quinazolin-5-amine;
(R)-7-methoxy-2-(2-(2-methyl-6,7-dihydrothiazolo[4,5-c]pyridin-5(4H)-yl)propyl)-[1,2,4]triazolo[1,5-c]quinazolin-5-amine;

(S)-7-methoxy-2-(2-(2-methyl-6,7-dihydrothiazolo[4,5-c]pyridin-5(4H)-yl)propyl)-[1,2,4]triazolo[1,5-c]quinazolin-5-amine;
(R)-7-methoxy-2-(2-(2-methyl-4H-pyrrolo[3,4-d]thiazol-5(6H)-yl)propyl)-[1,2,4]triazolo[1,5-c]quinazolin-5-amine;
(R)-7-methoxy-2-(2-(2-methyl-6,7-dihydropyrazolo[1,5-a]pyrazin-5(4H)-yl)propyl)-[1,2,4]triazolo[1,5-c]quinazolin-5-amine;
(S)-7-methoxy-2-(2-(2-methyl-6,7-dihydropyrazolo[1,5-a]pyrazin-5(4H)-yl)propyl)-[1,2,4]triazolo[1,5-c]quinazolin-5-amine;
(R)-2-(2-(2-(difluoromethyl)-6,7-dihydropyrazolo[1,5-a]pyrazin-5(4H)-yl)propyl)-7-methoxy-[1,2,4]triazolo[1,5-c]quinazolin-5-amine;
(S)-2-(2-(2-(difluoromethyl)-6,7-dihydropyrazolo[1,5-a]pyrazin-5(4H)-yl)propyl)-7-methoxy-[1,2,4]triazolo[1,5-c]quinazolin-5-amine;
(R)-2-(2-(2-(difluoromethyl)-6,7-dihydrothiazolo[5,4-c]pyridin-5(4H)-yl)propyl)-7-methoxy-[1,2,4]triazolo[1,5-c]quinazolin-5-amine;
(S)-7-methoxy-2-(2-(2-(trifluoromethyl)-6,7-dihydrothiazolo[4,5-c]pyridin-5(4H)-yl)propyl)-[1,2,4]triazolo[1,5-c]quinazolin-5-amine;
2-(3-(5H-pyrrolo[3,4-b]pyridin-6(7H)-yl)propyl)-7-methoxy-[1,2,4]triazolo[1,5-c]quinazolin-5-amine;
2-(3-(4-fluoroisoindolin-2-yl)propyl)-7-methoxy-[1,2,4]triazolo[1,5-c]quinazolin-5-amine;
2-(3-(5-fluoroisoindolin-2-yl)propyl)-7-methoxy-[1,2,4]triazolo[1,5-c]quinazolin-5-amine;
7-methoxy-2-(3-(5-(trifluoromethyl)isoindolin-2-yl)propyl)-[1,2,4]triazolo[1,5-c]quinazolin-5-amine;
7-methoxy-2-(2-(2,7,7-trimethyl-6,7-dihydrothiazolo[5,4-c]pyridin-5(4H)-yl)ethyl)-[1,2,4]triazolo[1,5-c]quinazolin-5-amine;
2-(2-(2,4-dimethyl-6,7-dihydrooxazolo[5,4-c]pyridin-5(4H)-yl)ethyl)-7-methoxy-[1,2,4]triazolo[1,5-c]quinazolin-5-amine;
2-(2-(2,6-dimethyl-6,7-dihydrooxazolo[5,4-c]pyridin-5(4H)-yl)ethyl)-7-methoxy-[1,2,4]triazolo[1,5-c]quinazolin-5-amine;
7-methoxy-2-(2-(2,7,7-trimethyl-6,7-dihydrothiazolo[5,4-c]pyridin-5(4H)-yl)ethyl)-[1,2,4]triazolo[1,5-c]quinazolin-5-amine;
2-(2-(2-cyclopropyl-4H-pyrrolo[3,4-d]thiazol-5(6H)-yl)ethyl)-7-methoxy-[1,2,4]triazolo[1,5-c]quinazolin-5-amine;
2-(2-(2-isopropyl-4H-pyrrolo[3,4-d]thiazol-5(6H)-yl)ethyl)-7-methoxy-[1,2,4]triazolo[1,5-c]quinazolin-5-amine;
2-(2-(2-ethyl-4H-pyrrolo[3,4-d]thiazol-5(6H)-yl)ethyl)-7-methoxy-[1,2,4]triazolo[1,5-c]quinazolin-5-amine;
7-methoxy-2-(2-(2-methyl-4H-pyrrolo[3,4-d]oxazol-5(6H)-yl)ethyl)-[1,2,4]triazolo[1,5-c]quinazolin-5-amine;
2-(2-(2-cyclopropyl-4H-pyrrolo[3,4-d]oxazol-5(6H)-yl)ethyl)-7-methoxy-[1,2,4]triazolo[1,5-c]quinazolin-5-amine;
7-methoxy-2-(2-(1-methylpyrrolo[3,4-c]pyrazol-5(1H,4H,6H)-yl)ethyl)-[1,2,4]triazolo[1,5-c]quinazolin-5-amine;
(R)-7-methoxy-2-(2-(2-methyl-4H-pyrrolo[3,4-d]oxazol-5(6H)-yl)propyl)-[1,2,4]triazolo[1,5-c]quinazolin-5-amine; or
(R)-7-methoxy-2-(2-(2-methyl-4H-pyrrolo[3,4-d]oxazol-5(6H)-yl)butyl)-[1,2,4]triazolo[1,5-c]quinazolin-5-amine, or a salt of any thereof.

In some embodiments a compound of the invention is:
2-(2-(2-cyclopropyl-4H-pyrrolo[3,4-d]thiazol-5(6H)-yl)ethyl)-7-methoxy-[1,2,4]triazolo[1,5-c]quinazolin-5-amine;
2-(2-(2-isopropyl-4H-pyrrolo[3,4-d]thiazol-5(6H)-yl)ethyl)-7-methoxy-[1,2,4]triazolo[1,5-c]quinazolin-5-amine;
2-(2-(2-ethyl-4H-pyrrolo[3,4-d]thiazol-5(6H)-yl)ethyl)-7-methoxy-[1,2,4]triazolo[1,5-c]quinazolin-5-amine;
7-methoxy-2-(2-(2-methyl-4H-pyrrolo[3,4-d]oxazol-5(6H)-yl)ethyl)-[1,2,4]triazolo[1,5-c]quinazolin-5-amine;
2-(2-(2-cyclopropyl-4H-pyrrolo[3,4-d]oxazol-5(6H)-yl)ethyl)-7-methoxy-[1,2,4]triazolo[1,5-c]quinazolin-5-amine;
7-methoxy-2-methylpyrrolo[3,4-c]pyrazol-5(1H,4H,6H)-yl)ethyl)-[1,2,4]triazolo[1,5-c]quinazolin-5-amine;
(R)-7-methoxy-2-(2-(2-methyl-4H-pyrrolo[3,4-d]oxazol-5(6H)-yl)propyl)-[1,2,4]triazolo[1,5-c]quinazolin-5-amine;
(R)-7-methoxy-2-(2-(2-methyl-4H-pyrrolo[3,4-d]oxazol-5(6H)-yl)butyl)-[1,2,4]triazolo[1,5-c]quinazolin-5-amine, or a salt of any thereof.

In some embodiments, preferably a compound of the invention is the compound 2-(2-(2-cyclopropyl-4H-pyrrolo[3,4-d]thiazol-5(6H)-yl)ethyl)-7-methoxy-[1,2,4]triazolo[1,5-c]quinazolin-5-amine, or a salt thereof. In some embodiments, preferably a compound of the invention is the compound 2-(2-(2-isopropyl-4H-pyrrolo[3,4-d]thiazol-5(6H)-yl)ethyl)-7-methoxy-[1,2,4]triazolo[1,5-c]quinazolin-5-amine, or a salt thereof. In some embodiments, preferably a compound of the invention is the compound 2-(2-(2-ethyl-4H-pyrrolo[3,4-d]thiazol-5(6H)-yl)ethyl)-7-methoxy-[1,2,4]triazolo[1,5-c]quinazolin-5-amine, or a salt thereof. In some embodiments, preferably a compound of the invention is the compound 7-methoxy-2-(2-(2-methyl-4H-pyrrolo[3,4-d]oxazol-5(6H)-yl)ethyl)-[1,2,4]triazolo[1,5-c]quinazolin-5-amine, or a salt thereof. In some embodiments, preferably a compound of the invention is the compound 2-(2-(2-cyclopropyl-4H-pyrrolo[3,4-d]oxazol-5(6H)-yl)ethyl)-7-methoxy-[1,2,4]triazolo[1,5-c]quinazolin-5-amine, or a salt thereof. In some embodiments, preferably a compound of the invention is the compound 7-methoxy-2-(2-(1-methylpyrrolo[3,4-c]pyrazol-5(1H,4H,6H)-yl)ethyl)-[1,2,4]triazolo[1,5-c]quinazolin-5-amine, or a salt thereof. In some embodiments, preferably a compound of the invention is the compound (R)-7-methoxy-2-(2-(2-methyl-4H-pyrrolo[3,4-d]oxazol-5(6H)-yl)propyl)-[1,2,4]triazolo[1,5-c]quinazolin-5-amine, or a salt thereof. In some embodiments, preferably a compound of the invention is the compound (R)-7-methoxy-2-(2-(2-methyl-4H-pyrrolo[3,4-d]oxazol-5(6H)-yl)butyl)-[1,2,4]triazolo[1,5-c]quinazolin-5-amine, or a salt thereof.

As described herein, unless otherwise indicated, the use of a compound in treatment means that an amount of the compound, generally presented as a component of a formulation that comprises other excipients, is administered in aliquots of an amount, and at time intervals, which provides and maintains at least a therapeutic serum level of at least one pharmaceutically active form of the compound over the time interval between dose administration.

Absolute stereochemistry is illustrated by the use of hashed and solid wedge bonds. As shown in Illus-I and Illus-II. Accordingly, the methyl group of is emerging from the page of the paper and the ethyl group in Illus-II is descending into the page, where the cyclohexene ring resides within the plane of the paper. It is assumed that the hydrogen on the same carbon as the methyl group of Illus-I desends into the page and the hydrogen on the same carbon as the ethyl group of emerges from the page. The convention is the same where both a hashed and solid rectangle are appended to the same carbon as in the Methyl group is emerging from the plane of the paper and the ethyl group is descending into the plane of the paper with the cyclohexene ring in the plane of the paper.

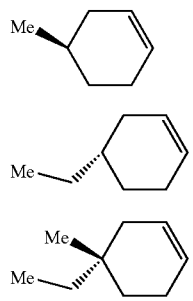

As is conventional, ordinary "stick" bonds or "wavy" bonds are used where there is a mixture of possible isomers present, including a racemic mixture of possible isomers As used herein, unless otherwise specified, the following terms have the following meanings:

The phrase "at least one" used in reference to the number of components comprising a composition, for example, "at least one pharmaceutical excipient" means that one member of the specified group is present in the composition, and more than one may additionally be present. Components of a composition are typically aliquots of isolated pure material added to the composition, where the purity level of the isolated material added into the composition is the normally accepted purity level of a substance appropriate for pharmaceutical use.

The phrase "at least one" used in reference to substituents on a compound or moiety appended to the core structure of a compound means that one substituent of the group of substituents specified is present, and more than one substituent may be bonded to chemically accessible bonding points of the core.

Whether used in reference to a substituent on a compound or a component of a pharmaceutical composition the phrase "one or more", means the same as "at least one";

"concurrently" and "contemporaneously" both include in their meaning (1) simultaneously in time (e.g., at the same time); and (2) at different times but within the course of a common treatment schedule;

"consecutively" means one following the other;

"sequentially" refers to a series administration of therapeutic agents that awaits a period of efficacy to transpire between administering each additional agent; this is to say that after administration of one component, the next component is administered after an effective time period after the first component; the effective time period is the amount of time given for realization of a benefit from the administration of the first component;

"effective amount" or "therapeutically effective amount" is meant to describe the provision of an amount of at least one compound of the invention or of a pharmaceutical composition comprising at least one compound of the invention which is effective in treating or inhibiting a disease, disorder or condition described herein, and thus produce the desired therapeutic, ameliorative, inhibitory or preventative effect. For example, in treating movement disorders with one or more of the compounds described herein "effective amount" (or "therapeutically effective amount") means, for example, providing the amount of at least one compound or pharmaceutically acceptable salt thereof of Formula GI that results in a therapeutic response in a patient afflicted with a central nervous system disorder, including a response suitable to manage, alleviate, ameliorate, or treat the disorder or alleviate, ameliorate, reduce, or eradicate one or more symptoms attributed to the disorder and/or long-term stabilization of the disorder, for example, as may be determined by the analysis of pharmacodynamic markers or clinical evaluation of patients afflicted with the disorder;

"patient" and "subject" means an animal, such as a mammal (e.g., a human being) and is preferably a human being;

"prodrug" means compounds that are rapidly transformed, for example, by hydrolysis in blood, in vivo to the parent compound, e.g., conversion of a prodrug of Formula GI to a compound of Formula GI, or to a pharmaceutically acceptable salt thereof; a thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference; the scope of this invention includes prodrugs of the novel compounds of this invention;

"solvate" means a physical association of a compound of this invention with one or more solvent molecules; this physical association involves varying degrees of ionic and covalent bonding, including hydrogen bonding; in certain instances the solvate will be capable of isolation, for example when one or more solvent molecules are incorporated in the crystal lattice of the crystalline solid; "solvate" encompasses both solution-phase and isolatable solvates; non-limiting examples of suitable solvates include ethanolates, methanolates, and the like; "hydrate" is a solvate wherein the solvent molecule is $H_2O$.

The term "substituted" means that one or more of the enumerated substituents (or, where a list of substituents are not specifically enumerated, the default substituents specified in this "Definitions" section for the particular type of substrate which contains variable substituents) can occupy one or more of the bonding positions on the substrate typically occupied by "—H", provided that such substitution does not exceed the normal valency rules for the atom in the bonding configuration present in the substrate, and that the substitution ultimate provides a stable compound, e.g., mutually reactive substituents are not present geminal or vicinal to each other, and wherein such a compound is sufficiently robust to survive isolation to a useful degree of purity from a reaction mixture; when the text indicates optional substitution of a moiety (e.g. "optionally substituted") the term means "if present, one or more of the enumerated (or default substituents for the specified substrate) can be present on the substrate in a bonding position normally occupied by a hydrogen atom" in accordance with the definition of "substituted" presented herein.

As used herein, unless otherwise specified, the following terms used to describe moieties, whether comprising the entire definition of a variable portion of a structural representation of a compound of the invention or a substituent appended to a variable portion of a structural representation of a group of compounds of the invention have the following meanings, and unless otherwise specified, the definitions of each term (i.e., moiety or substituent) apply when that term is used individually or as a component of another term (e.g., the definition of aryl is the same for aryl and for the aryl portion of arylalkyl, alkylaryl, arylalkynyl moieties, and the like); moieties are equivalently described herein by structure, typographical representation or chemical terminology without intending any differentiation in meaning, for example, the chemical term "acyl", defined below, is equivalently described herein by the term itself, or by typographical representations "R'—(C=O)—" or "R'—C(O)—", or by the structural representation:

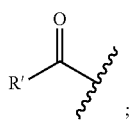

"acyl" means an R'—C(O)—, where R' is linear, branched or cyclic alkyl; linear, branched or cyclic alkenyl; or linear, branched or cyclic alkynyl moiety, each of which moieties can be substituted; wherein the acyl substituent is bonded through the carbonyl carbon to the substrate of which it is a substituent, or —NH—SO$_2$—R', where —R' is as previously defined; non-limiting examples of suitable acyl groups include formyl, acetyl, propanoyl, 2-methylpropanoyl, butanoyl and cyclohexanoyl;

"alkenyl" means an aliphatic hydrocarbon moiety which is not aromatic but includes its structure at least one constituent of the structure —(R'C=CR'$_2$) or —(R'C=CR'$_2$)—, where R' is a defined substituent, for example —H or -alkyl; the alkenyl moiety can be incorporated into a linear hydrocarbon chain, or incorporated into a cyclic hydrocarbon chain (termed "cycloalkenyl") and can comprise further, linear, branched, or cyclic substituents depending from the carbon atoms of the chain, preferably the chain comprises about 2 to about 15 carbon atoms; more preferably from about 2 to about 12 carbon atoms; and more preferably chains comprise from about 2 to about 6 carbon atoms;

the term "substituted alkenyl", unless specified otherwise by a recitation of specific substituents defining the term, means that the alkenyl group is substituted by one or more substituents which are independently for each occurrence: C$_{1-10}$ alkyl, C$_{3-10}$ cycloalkyl, and C$_{1-10}$ alkoxy;

"-alkoxy" means a moiety of the structure: alkyl-O— (i.e., the bond to the substrate moiety is through the ether oxygen), wherein the alkyl portion of the moiety is as defined below for alkyl; non-limiting examples of suitable alkoxy groups include methoxy, ethoxy, n-propoxy, iso-propoxy, n-butoxy and heptoxy;

"alkoxyalkyl" means a moiety of the structure: alkoxy-alkyl- (i.e., the bond to the substrate moiety is through an alkyl moiety, which is terminated by, or substituted with, an alkoxy substituent that is not itself bonded to the substrate, non-limiting examples of alkoxyalkyl groups include H$_3$C—(CH$_2$)$_y$—O—CH$_2$—(CH$_2$)$_x$— wherein "y" and "x" are independently an integer of from 0 to 6;

"alkoxycarbonyl" means a moiety of the structure alkyl-O—C(O)—, equivalently represented as [alkyl-O—(C=O)—] and also as R—O(C=O)—, where "R" is a defined alkyl moiety, (i.e., the bond to the parent moiety is through the carbonyl carbon) wherein the alkoxy portion of the moiety is as previously defined; non-limiting examples of suitable alkoxycarbonyl groups include methoxycarbonyl and ethoxycarbonyl;

"-alkyl" (including the alkyl portions of other moieties, such as trifluoromethyl-alkyl- and (-alkoxy) means an aliphatic hydrocarbon chain comprising from about 1 to about 20 carbon atoms (that is, "C$_{1-20}$ alkyl"), preferably 1 to about 10 carbon atoms (herein "C$_{1-10}$ alkyl"), unless the term is modified by an indication that a shorter chain is contemplated, for example, an alkyl moiety of up to 8 carbon atoms (designated herein "C$_{1-8}$-alkyl"); the term "alkyl", unless specifically limited by another term, for example, "linear", "branched", or "cyclic", includes alkyl moieties which are linear (a hydrocarbon chain with no aliphatic hydrocarbon "branches" appended to it); branched (a main hydrocarbon chain comprising up to the maximum specified number of carbon atoms with a lower-alkyl chain appended to one or more carbon atoms comprising, but not terminating, the main hydrocarbon chain); and cyclic (the main hydrocarbon chain forms an cyclic aliphatic moiety of from 3 carbon atoms, the minimum number necessary to provide a cyclic moiety, up to the maximum number of specified carbon atoms accordingly when unmodified, the term "C$_{1-x}$ alkyl" refers to linear, branched, or cyclic alkyl, and the "C$_{1-x}$" designation means: for a cyclic moiety a ring comprising at minimum 3 carbon atoms up to "X" carbon atoms; for a branched moiety, a main chain of at least 3 carbon atoms up to "X" carbon atoms with at least one linear or branched alkyl moiety bonded to a carbon atom which does not terminate the chain; and for a linear alkyl, a moiety comprising one carbon atom (i.e., -methyl), up to "X" carbon atoms; when the term "alkyl" is modified by "substituted" or "optionally substituted" it means an alkyl group having substituents in accordance with the relevant definitions appearing below; where use of the terms "substituted" or "optionally substituted" modify "alkyl" and substituent moieties are not specifically enumerated, the substituents bonded to the alkyl substrate are independently for each occurrence accordance with definitions appearing herein): C$_{1-20}$ alkyl; halogen; -alkoxy; —OH; —CN; alkylthio-; amino, —NH(alkyl), —NH(cycloalkyl), —N(alkyl)$_2$, —(C=O)—OH; —C(O)O-alkyl; —S(alkyl); or —S(O$_2$)-alkyl; or -aryl; cycloalkyl moieties may alternatively, or in addition, be substituted with one or more, "ring-system substituents" as that term is defined herein. Examples of suitable alkyl groups include, but are not limited to, methyl, ethyl, n-propyl, isopropyl, n-butyl, t-butyl, n-pentyl, heptyl, nonyl, decyl, fluoromethyl, trifluoromethyl and cyclopropylmethyl, where the term "alkyl" is indicated with two hyphens (i.e., "-alkyl-" it indicates that the alkyl moiety is bonded in a manner that the alkyl moiety connects a substrate with another moiety, for example, "-alkyl-OH" indicates an alkyl moiety connecting a hydroxyl moiety to a substrate;

"lower alkyl" means a group comprising about 1 to about 6 carbon atoms in the chain (i.e. C$_{1-6}$); non-limiting examples of suitable lower alkyl groups include methyl, ethyl, n-propyl, isopropyl, n-butyl, t-butyl, n-pentyl, and hexyl;

"alkylaryl" (or alkaryl) means an alkyl-aryl-group (i.e., the bond to the parent moiety is through the aryl group) wherein the alkyl group is unsubstituted or substituted as defined above, and the aryl group is unsubstituted or substituted as defined below; preferred alkyl aryl moieties comprise a lower alkyl group; non-limiting examples of suitable alkylaryl groups include o-tolyl, p-tolyl and xylyl;

in general, as exemplified by the term "alkyl-aryl" defined above, a substituent which is the called out by the combination of terms used to define two other substituent fragments indicates that the substituent called out by the last term used is bonded to the substrate whilst the preceding term called out is bonded in turn to the substituent fragment it precedes, proceeding right to left to understand the order in which the various fragments are bonded to the substrate;

"alkynyl" means an aliphatic hydrocarbon group (chain) comprising at least one moiety of the structure:

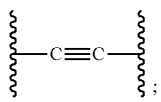

or the structure:

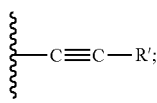

wherein R' is a defined substituent, the alkynyl moiety can be incorporated into a linear or branched hydrocarbon chain, or incorporated into a cyclic hydrocarbon chain (non-aromatic, termed "cycloalkynyl"); preferably hydrocarbon chains of an alkynyl moiety comprises about 2 to about 15 carbon atoms; more preferably alkynyl groups comprise about 2 to about 12 carbon atoms in the chain; and more preferably about 2 to about 4 carbon atoms in the chain;

"amino" means an —$NR^2$ group wherein R is selected independently for each occurrence from —H or alkyl, alkylamino means —$NR'_2$, wherein one R' is -alkyl and the other is —H or -alkyl selected independently for each occurrence, non-limiting examples of alkylamino moieties are —NH—$CH_3$ (methylamino-) and —$N(CH_3)_2$ (dimethylamino);

"ammonium ion" means —$N^+R_3$ wherein R is independently —H, alkyl, substituted alkyl, or the cationic portion of a dissociated acid capable of producing an ammonium ion from an amine; when not explicitly shown in representations herein the presence of an ammonium ion presumes that a charge-balancing anion is associated with the ammonium ion moiety, which anion is derived from the anionic portion of the acid used to provide said ammonium ion, it will be appreciated that many of the nitrogen atoms present in compounds of the invention can be converted to an ammonium ion thereby providing a salt of the parent compound, which is within the scope of the invention;

"aryl" (sometimes abbreviated "ar") means an aromatic monocyclic or multicyclic ring system comprising about 6 to about 14 carbon atoms (denoted herein also as "$C_{6-14}$-aryl"), preferably about 6 to about 10 carbon atoms ("$C_{6-10}$-aryl"); the aryl group can be optionally substituted with one or more independently selected "ring system substituents" (defined below). Non-limiting examples of suitable aryl groups include naphthyl

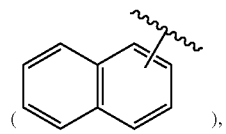

and phenyl

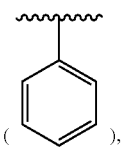

which is also abbreviated herein "Ph" for convenience, wherein bonding can be through any of the carbons in the aromatic ring, and wherein any ring carbon atoms not participating in a bond to the substrate may have bonded to it a substituent other than —H, independently selected in each instance from the list of "ring-system substituents" defined herein, or as defined in each instance where the term is used in conjunction with an enumerated list of substituents;

"aryloxy" means an aryl-O-group (i.e., the moiety is bonded to a substrate through the ether oxygen) wherein the aryl group is unsubstituted or substituted as defined above; non-limiting examples of suitable aryloxy groups include phenoxy and naphthoxy;

"aryloxycarbonyl" means an aryl-O—C(O)-group (i.e., the bond to a substrate is through the carbonyl carbon) wherein the aryl group is unsubstituted or substituted as previously defined; non-limiting examples of suitable aryloxycarbonyl groups include phenoxycarbonyl and naphthoxycarbonyl;

a "carboxylic acid" moiety means a substituent having the formula "—C(O)—OH", wherein the moiety is bonded to a substrate is through the carbonyl carbon;

"cycloalkyl" defined above with the "alkyl" definition, means a non-aromatic mono- or multicyclic ring system comprising about 3 to about 20 carbon atoms which may be substituted as defined herein; the term includes multicyclic cycloalkyls, for example, 1-decalin, norbornyl, adamantyl and the like;

"halogen" means fluorine, chlorine, bromine, or iodine; preferred halogens, unless specified otherwise where the term is used, are fluorine, chlorine and bromine, a substituent which is a halogen atom means —F, —Cl, —Br, or —I, and "halo" means fluoro, chloro, bromo, or iodo substituents bonded to the moiety defined, for example, "haloalkyl" means an alkyl, as defined above, wherein one or more of the bonding positions on the alkyl moiety typically occupied by hydrogen atoms are instead occupied by a halo group, perhaloalkyl means that all bonding positions not participating in bonding the alkyl substituent to a substrate are occupied by a halogen, for example, perfluoroalkyl, where alkyl is methyl, means —$CF_3$;

"heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination; preferred heteroaryl moieties comprise 5 ring atoms, for example, thiazole thiadiazole, imidazole, isothiazole, oxazole, oxadiazole, or pyrazole; the "heteroaryl" can be optionally substituted at chemically available ring atoms by one or more independently selected "ring system substituents" (defined below); the prefix aza, azo, oxa, oxo, thia or thio before the heteroaryl root name means that at least a nitrogen, oxygen or sulfur atom, respectively, is present as a ring atom, and in some embodiments 2 or more heteroatoms are present in a ring, for example, a pyrazole or a thiazole moiety; a nitrogen atom of a heteroaryl can be optionally oxidized to the corresponding N-oxide; non-limiting examples of heteroaryl moieties include: pyridyl-

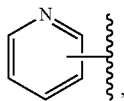

thiopenyl-

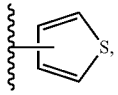

furanyl-

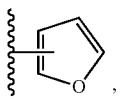

triazolyl

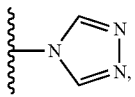

oxazolyl

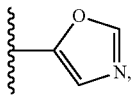

pyrazinyl, thienyl, pyrimidinyl, isoxazolyl, isothiazolyl, thiazolyl, pyrazolyl, furazanyl, pyrrolyl, pyrazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazan, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl, furopyridine, for example:

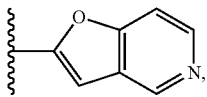

and the like (unless otherwise noted, bonded to the substrate through any available atom that results in a stable bonding arrangement);

"heterocyclyl" (or heterocycloalkyl) means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination; there are no adjacent oxygen and/or sulfur atoms present in the ring system; preferred heterocyclyl moieties contain about 5 to about 6 ring atoms; the prefix aza, oxa or thia before the heterocyclyl root name means that at least one nitrogen, oxygen or sulfur atom, respectively, is present as a ring atom; the heterocyclyl can be optionally substituted by one or more independently selected "ring system substituents" (defined below); the nitrogen or sulfur atom of the heterocyclyl can be optionally oxidized to the corresponding N-oxide, S-oxide or S,S-dioxide; non-limiting examples of suitable monocyclic heterocyclyl rings include piperidyl, pyrrolidinyl, piperazinyl, morpholinyl-

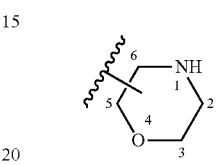

(where unless otherwise noted the moiety is bonded to the substrate through any of ring carbon atoms C2, C3, C5, or C6), thiomorpholinyl, thiazolidinyl, 1,3-dioxolanyl, 1,4-dioxanyl, tetrahydrofuranyl, tetrahydrothiophenyl, tetrahydrothiopyranyl, and the like;

"tetrahydropyranyl" moiety means a 6-member cyclic ether of the formula:

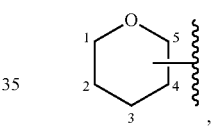

where, the bond line having an open end in the center of the structure and terminated at the other end with a wavy line indicates that the substituent is bonded to the substrate to which it is attached through any of carbon atoms 1 to 5, and wherein any of the bonding positions on carbons 1 to 5 normally occupied by a hydrogen atom, that is, the bonding positions on carbon atoms 1 to 5 which are not occupied by the bond to the substrate can optionally be occupied by specified or optional substituents;

"piperidinyl" means:

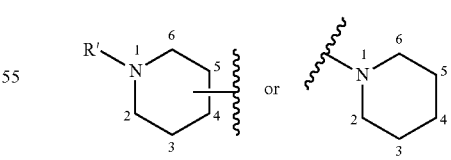

where, the open bond line terminated on one end with a wavy line indicates the ring atom through which the moiety is bonded to the substrate (i.e., any of carbon atoms 2 to 6 (left-hand structure) or the ring nitrogen atom (right-hand structure), and wherein any of the bonding positions on the nitrogen atom or on carbon atoms 2 to 6 not participating in a bond to the substrate and normally occupied by a hydrogen atom can be bonded to a specified or optional substituent, and wherein R', if present, is either or another specified substituent;

"pyridinyl" means:

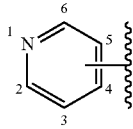

where, the bond-terminated-with-wavy-line indicates that the pyridinyl moiety is bonded to the substrate at any of carbon atoms 2 to 6, and wherein any of the bonding positions on carbons 2 to 6 normally occupied by a hydrogen atom, that is, any position on carbon 2 to 6 which is not the bond to the substrate, can optionally be occupied by a specified substituent;

"quinoline" means:

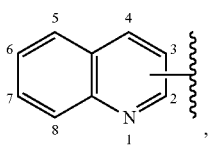

where, the bond-terminated-with-wavy-line indicates that the moiety is bonded to the substrate through any of carbon atoms 2 to 8, and wherein any of the bonding positions on carbon atoms 2 to 8 normally occupied by a hydrogen atom, that is, any bonding positions on carbon atoms 2 to 8 which are not bonded to the substrate, can optionally be occupied by one of a list of enumerated substituents;

for any of the foregoing ring-system moieties, bonding of the moiety through a specific ring carbon atom (or heteroatom) is sometimes described for convenience and "bonded through C—X to C—Y carbon atoms", where "X" and "Y" are integers referring to the carbon atoms, for example, as numbered in the examples above;

"hydroxyl moiety" and "hydroxy" means an HO— group, "hydroxyalkyl" means a substituent of the formula: "HO-alkyl-", wherein the alkyl group is bonded to the substrate and may be substituted or unsubstituted as defined above; preferred hydroxyalkyl moieties comprise a lower alkyl; Non-limiting examples of suitable hydroxyalkyl groups include hydroxymethyl and 2-hydroxyethyl; and bonding sequence is indicated by hyphens where moieties are represented in text, for example -alkyl, indicates a single bond between a substrate and an alkyl moiety, -alkyl-X, indicates that an alkyl group bonds an "X" substituent to a substrate, and in structural representation, bonding sequence is indicated by a wavy line terminating a bond representation, for example:

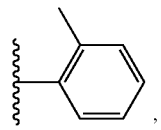 [SMILES: *c1ccccc1C]

indicates that the methylphenyl moiety is bonded to a substrate through a carbon atom ortho to the methyl substituent, while a bond representation terminated with a wavy line and drawn into a structure without any particular indication of an atom to which it is bonded indicates that the moiety may be bonded to a substrate via any of the atoms in the moiety which are available for bonding, for example:

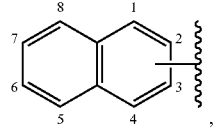

indicates that the naphthalene moiety may be bonded to the substrate through any of carbons 1 to 8.

Where substituents are presented in text, unless defined differently at the point of use, bonding arrangement is indicated with hyphens (indicating single bonds), equal signs (indicating double bonds), parentheses (indicating bonding to the adjacent atom, see the carbonyl example below) and "carrots" (i.e. "<" or ">") indicating two single bonds.

Thus, for example, the carbonyl moiety:

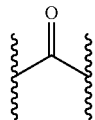 [SMILES: *C(*)=O]

may be represented in text as >C=O or alternatively as —C(O)— and a cyano-substituent may be represented as —C(N) or —CN. In the same regard, unsaturated nitrogen moiety, for example:

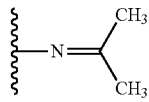

may be represented in text as —N=C(CH$_3$)$_2$, and a saturated nitrogen moiety, for example, where one definition of "A" in the structure:

is methyl-substituted nitrogen, thus providing the structure:

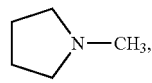

when defining "A" the nitrogen moiety can be represented herein in text as: >N—CH$_3$, or alternatively —(N—CH$_3$)—.

The foregoing are illustrative of the various text notation used herein for defining structural variables and substituents using text representation.

Any carbon or heteroatom with unsatisfied valences in the text, schemes, examples, structural formulae, and any Tables herein is assumed to have a hydrogen atom or atoms of sufficient number to satisfy the valences;

The term "pharmaceutical composition" as used herein encompasses both the bulk composition and individual dosage units comprised of more than one (e.g., two) pharmaceutically active agents such as, for example, a compound of the present invention and an additional agent as described herein, along with any pharmaceutically inactive excipients. As will be appreciated by the ordinarily skilled artisan, excipients are any constituent which adapts the composition to a particular route of administration or aids the processing of a composition into a dosage form without itself exerting an active pharmaceutical effect. The bulk composition and each individual dosage unit can contain fixed amounts of the afore-said "more than one pharmaceutically active agents". The bulk composition is material that has not yet been formed into individual dosage units.

This invention also includes the compounds of this invention in isolated and purified form obtained by routine techniques. Polymorphic forms of the compounds of Formula GI, and of the salts thereof, are intended to be included in the present invention. Certain compounds of the invention may exist in different isomeric (e.g., enantiomers, diastereoisomers, atropisomers) forms. The invention contemplates all such isomers both in pure form and in admixture, including racemic mixtures.

All stereoisomers (for example, geometric isomers, optical isomers and the like) of the present compounds (including prodrugs of compounds of the invention as well as the salts and solvates of the inventive compounds and their prodrugs), such as those which may exist due to asymmetric carbons present in a compound of the invention, and including enantiomeric forms (which may exist even in the absence of asymmetric carbons), rotameric forms, atropisomers, and diastereomeric forms, are contemplated within the scope of this invention. Individual stereoisomers of the compounds of the invention may be isolated in a pure form, for example, substantially free of other isomers, or may be isolated as an admixture of two or more stereoisomers or as a racemate. The chiral centers of the present invention can have the S or R configuration as defined by the IUPAC 1974 Recommendations. The use of the terms "salt", "solvate" "prodrug" and the like, is intended to equally apply to salts, solvates and prodrugs of isolated enantiomers, stereoisomer pairs or groups, rotamers, tautomers, or racemates of the inventive compounds.

Where diasteromeric mixtures can be separated into their individual diastereomers on the basis of their physical chemical differences by methods well known to those skilled in the art, for example, by chiral chromatography and/or fractional crystallization. As is known, enantiomers can also be separated by converting the enantiomeric mixture into a diasteromeric mixture by reaction with an appropriate optically active compound (e.g., chiral auxiliary such as a chiral alcohol or Mosher's acid chloride), separating the diastereomers and converting (e.g., hydrolyzing) the individually isolated diastereomers to the corresponding enantiomers.

Where the compounds of the invention form salts by known, ordinary methods, these salts are also within the scope of this invention. Reference to a compound of the invention herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of the invention contains both a basic moiety, for example, but not limited to, a nitrogen atom, for example, an amine, pyridine or imidazole, and an acidic moiety, for example, but not limited to a carboxylic acid, zwitterions ("inner salts") may be formed and are included within the term "salt(s)" as used herein. Pharmaceutically acceptable (i.e., non-toxic, physiologically acceptable salts) are preferred. Salts of the compounds of the invention may be formed, for example, by reacting a compound of the invention with an amount of acid or base, for example, an equivalent amount, in a medium in which the salt precipitates or in an aqueous medium wherein the product is obtained by lyophilization. Acids (and bases) which are generally considered suitable for the formation of pharmaceutically useful salts from basic (or acidic) pharmaceutical compounds are discussed, for example, by S. Berge et al., *Journal of Pharmaceutical Sciences* (1977) 66(1) 1-19; P. Gould, *International J of Pharmaceutics* (1986) 33 201-217; Anderson et al, *The Practice of Medicinal Chemistry* (1996), Academic Press, New York; in *The Orange Book* (Food & Drug Administration, Wash., D.C, on their website); and P. Heinrich Stahl, Camille G. Wermuth (Eds.), *Handbook of Pharmaceutical Salts: Properties, Selection, and Use*, (2002) Intl. Union of Pure and Applied Chemistry, pp. 330-331. These disclosures are incorporated herein by reference.

Where it is possible to provide an acid addition salt with a compound, in general, acid addition salts include, but are not limited to, acetates, including trifluoroacetate salts, adipates, alginates, ascorbates, aspartates, benzoates, benzenesulfonates, bi sulfates, borates, butyrates, citrates, camphorates, catnphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenytpropionates, phosphates, picrates, pivalates, propionates, salicylates, succinates, sulfates, sulfonates (such as those mentioned herein), tartarates, thiocyanates, toluenesulfonates (also known as tosylates) undecanoates, and the like.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis(dehydroabietyl)ethylenediamine), N-methyl-D-glucamines, N-methyl-D-glucamides, t-butyl amines, piperazine, phenylcyclohexyl-amine, choline, tromethamine, and salts with amino acids such as arginine, lysine and the like. Basic nitrogen-containing groups may be converted to an ammonium ion or quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid and base salts are intended to be pharmaceutically acceptable salts within the scope of the invention and all acid and base salts are considered equivalent to the free forms of the corresponding compounds for purposes of the invention.

Compounds of the invention may exist in exist in different tautomeric forms. All such forms are embraced and included within the scope of the invention. Examples of well-known tautomeric forms include, but are not limited to, ketone/enol tautomeric forms, imine-enamine tautomeric forms, and for example heteroaromatic forms such as the following moieties:

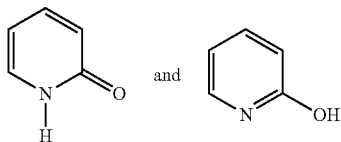

Where a compound of the invention can exist in more than one such form, representation or presentation of one tautomeric form of such compound is considered herein equivalent to presentation of all the tautomeric forms in which the compound exists.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, and in sufficient purity to be characterized by standard analytical techniques described herein or well known to the skilled artisan.

A functional group in a compound termed "protected" means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, N.Y.

When a variable (e.g., aryl, heterocycl, $R^3$, etc.) appears more than once in any moiety or in any compound of the invention, the selection of moieties defining that variable for each occurrence is independent of its definition at every other occurrence unless specified otherwise in the variable definition.

As used herein, the term "composition" is intended to encompass a product comprising the specified ingredients in the specified amounts, and any product which results, directly or indirectly, from combination of the specified ingredients in the specified amounts.

The present invention also embraces isotopically-labeled compounds of the present invention which are structurally identical to those recited herein, but for the fact that a statistically significant percentage of one or more atoms in that form of the compound are replaced by an atom having an atomic mass or mass number different from the atomic mass or mass number of the most abundant isotope usually found in nature, thus altering the naturally occurring abundance of that isotope present in a compound of the invention. Examples of isotopes suitable for inclusion in the compounds of the invention include isotopes of hydrogen (such as $^2H$ and $^3H$), carbon (such as $^{11}C$, $_{13}C$ and $^{14}C$), nitrogen (such as $^{13}N$ and $^{15}N$), oxygen (such as $^{15}O$, $^{17}O$ and $^{18}O$), phosphorus (such as $^{32}P$), sulfur (such as $^{35}S$), fluorine (such as $^{18}F$), iodine (such as $^{123}I$ and $^{125}I$) and chlorine (such as $^{36}Cl$). It will be appreciated that other isotopes may be incorporated by known means also.

Certain isotopically-labeled compounds of the invention (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly useful for their ease of preparation and detection. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the Schemes and/or in the Examples herein below, by substituting an appropriate isotopically labeled reagent for a non-isotopically labeled reagent. Such compounds are included also in the present invention.

In one aspect, as mentioned above, the present invention provides pharmaceutical formulations (pharmaceutical compositions) for use in antagonizing $A_{2A}$ receptors an to potentially treat central nervous system (CNS) disorders, for example, movement disorders associated with Parkinson's disease or the treatment thereof, wherein the compositions comprising at least one compound, or pharmaceutically acceptable salt thereof, of Formula GI, as defined herein.

As mentioned above, in one aspect the invention provides pharmaceutical formulations (pharmaceutical compositions) suitable for use in blocking adenosine A2a receptors found in the basal ganglia, comprising at least one compound of Formula GI presented above, or a pharmaceutically acceptable salt thereof, and at least one pharmaceutically acceptable carrier (described below). It will be appreciated that pharmaceutically formulations of the invention may comprise more than one compound of the invention, for example, the combination of two or three compounds of the invention, each present by adding to the formulation the desired amount of the compound in a pharmaceutically acceptably pure form. It will be appreciated that compositions of the invention may comprise, in addition to one or more of compounds of the invention, one or more other compounds which also have pharmacological activity, for example, as described herein below.

While formulations of the invention may be employed in bulk form, it will be appreciated that for most applications the inventive formulations will be incorporated into a dosage form suitable for administration to a patient, each dosage form comprising an amount of the selected formulation which contains an effective amount of said one or more compounds of the invention. Examples of suitable dosage forms include, but are not limited to, dosage forms adapted for: (i) oral administration, e.g., a liquid, gel, powder, solid or semi-solid pharmaceutical composition which is loaded into a capsule or pressed into a tablet and may comprise additionally one or more coatings which modify its release properties, for example, coatings which impart delayed release or formulations which have extended release properties; (ii) a dosage form adapted for intramuscular administration (IM), for example, an injectable solution or suspension, and which may be adapted to form a depot having extended release properties; (iii) a dosage form adapted for intravenous administration (IV), for example, a solution or suspension, for example, as an IV solution or a concentrate to be injected into a saline IV bag; (iv) a dosage form adapted for administration through tissues of the oral cavity, for example, a rapidly dissolving tablet, a lozenge, a solution, a gel, a sachette or a needle array suitable for providing intramucosal administration; (v) a dosage form adapted for administration via the mucosa of the nasal or upper respiratory cavity, for example a solution, suspension or emulsion formulation for dispersion in the nose or airway; (vi) a dosage form adapted for transdermal administration, for example, a patch, cream or gel; (vii) a dosage form adapted for intradermal administration, for example, a microneedle array; and (viii) a dosage form adapted for delivery via rectal or vaginal mucosa, for example, a suppository.

For preparing pharmaceutical compositions from the compounds described by this invention, generally pharmaceutically active compounds are combined with one or more pharmaceutically inactive excipients. These pharmaceutically inactive excipients impart to the composition properties which make it easier to handle or process, for example, lubricants or pressing aids in powdered medicaments intended to be tableted, or adapt the formulation to a desired route of administration, for example, excipients which provide a formulation for oral administration, for example, via absorption from the gastrointestinal tract, transdermal or transmucosal administration, for example, via adhesive skin "patch" or buccal administration, or injection, for example, intramuscular or intravenous, routes of administration. These excipients are collectively termed herein "a carrier".

Pharmaceutical compositions can be solid, semi-solid or liquid. Solid form preparations can be adapted to a variety of modes of administration and include powders, dispersible granules, mini-tablets, beads, and the like for example, for tableting, encapsulation, or direct administration. Typically formulations may comprise up to about 95 percent active ingredient, although formulations with greater amounts may be prepared.

Liquid form preparations include solutions, suspensions and emulsions. Examples of liquid forms of medicament include, but are not limited to, water or water/surfactant mixtures, for example a water-propylene glycol solution, which can be employed in the preparation of formulations intended, for example, for parenteral injection, for example, as a solvent or as a suspending medium for the preparation of suspensions and emulsions where a medicament comprises constituents which are insoluble in water or water/surfactant mixtures. Liquid form preparations may also include solutions or suspensions for intranasal administration and may also include, for example, viscosity modifiers to adapt the formulation for application to particular mucosa tissues accessible via nasal administration.

Aerosol preparations, for example, suitable for administration via inhalation or via nasal mucosa, may include solutions and solids in powder form, which may be in combination with a pharmaceutically acceptable propellant, for example, an inert compressed gas, e.g. nitrogen. Also included are solid form preparations which are intended to be converted, shortly before use, to a suspension or a solution, for example, for oral or parenteral administration. Examples of such solid forms include freeze dried formulations and liquid formulations adsorbed into a solid absorbent medium.

The compounds of the invention may also be deliverable transdermally or transmucosally, for example, from a liquid, suppository, cream, foam, gel, or rapidly dissolving solid form. It will be appreciated that transdermal compositions can take also the form of creams, lotions, aerosols and/or emulsions and can be provided in a unit dosage form which includes a transdermal patch of any know in the art, for example, a patch which incorporates either a matrix comprising the pharmaceutically active compound or a reservoir which comprises a solid or liquid form of the pharmaceutically active compound.

Examples of pharmaceutically acceptable carriers and methods of manufacture for various compositions mentioned above may be found in A. Gennaro (ed), Remington: The Science and Practice of Pharmacy, $20^{th}$ Edition, (2000), Lippincott Williams & Wilkins, Baltimore, Md.

Preferably, the pharmaceutical preparation is in a unit dosage form. In such form, the preparations subdivided into suitably sized unit doses containing appropriate quantities of the active component, e.g., an effective amount to achieve the desired purpose.

The actual dosage employed may be varied depending upon the requirements of the patient and the severity of the condition being treated. Determination of the proper dosage regimen for a particular situation is within the skill in the art. For convenience, the total daily dosage may be divided and administered in portions during the day as required.

In another embodiment the present invention provides for use of the compounds described herein for the potential treatment, management, alleviation or amelioration of conditions or disease states which can be, or are believed to be, treated, managed, alleviated or ameliorated by specific blocking of adenosine A2a receptors, for example, central nervous system diseases or disorders, including but not limited to the treatment of movement disorders (e.g., tremors, bradykinesias, gait, dystonias, dyskinesias, tardive dyskinesias, other extrapyramidal syndromes, Parkinson's disease and disorders associated with Parkinson's disease). The compounds of the invention also have the potential for use in preventing or lessening the effect of drugs that cause movement disorders.

In accordance with the present invention, blocking adenosine A2a receptors is accomplished by administering to a patient in need of such therapy an effective amount of one or more compounds of the invention, or a pharmaceutically acceptable salt thereof.

In some embodiments it is preferred for the compound to be administered in the form of a pharmaceutical composition comprising the compound of the invention, or a salt thereof, and at least one pharmaceutically acceptable carrier (described below). It will be appreciated that pharmaceutically formulations of the invention may comprise more than one compound of the invention or a salt thereof, for example, the combination of two or three compounds of the invention, each present by adding to the formulation the desired amount of the compound or a salt thereof which has been isolated in a pharmaceutically acceptably pure form.

As mentioned above, administration of a compound of the invention to effect antagonism of A2a receptor sites, which is believed to be beneficial in the treatment of central nervous system diseases is preferably accomplished by incorporating the compound into a pharmaceutical formulation incorporated into a dosage form, for example, one of the above-described dosage forms comprising an effective amount of at least one compound of the invention (e.g., 1, 2 or 3, or 1 or 2, or 1, and usually 1 compound of the invention), or a pharmaceutically acceptable salt thereof, for example. Methods for determining safe and effective administration of compounds which are pharmaceutically active, for example, a compound of the invention, are known to those skilled in the art, for example, as described in the standard literature, for example, as described in the "Physicians' Desk Reference" (PDR), e.g., 1996 edition (Medical Economics Company, Montvale, N.J. 07645-1742, USA), the Physician's Desk Reference, $56^{th}$ Edition, 2002 (published by Medical Economics company, Inc. Montvale, N.J. 07645-1742), or the Physician's Desk Reference, 57$^{th}$ Edition, 2003 (published by Thompson PDR, Montvale, N.J. 07645-1742); the disclosures of which is incorporated herein by reference thereto. The amount and frequency of administration of the compounds of the invention and/or the pharmaceutically acceptable salts thereof will be regulated according to the judgment of the attending clinician considering such factors as age, condition and size of the patient as well as severity of the symptoms being treated. Compounds of the instant invention can be administered at a total daily dosage of up to 1,000 mg, which can be administered in one daily dose or can be divided into two to four doses per day.

In general, in whatever form administered, the dosage form administered will contain an amount of at least one compound of the invention, or a salt thereof, which will provide a therapeutically effective serum level of the compound in some form for a period of at least 2 hours, preferably at least four hours, and preferably longer. In general, as is known in the art, dosages of a pharmaceutical composition providing a therapeutically effective serum level of a compound of the invention, e.g., a compound of Formula GI or GII, or a pharmaceutically acceptable salt thereof, can be spaced in time to provide serum level meeting or exceeding the minimum therapeutically effective serum level on a continuous basis throughout the period during which treatment is administered. As will be appreciated the dosage form administered may also be in a form providing an extended release period for the pharmaceutically active compound which will provide a therapeutic serum level for a longer period, necessitating less frequent dosage intervals. As mentioned above, a composition of the invention can incorporate additional pharmaceutically active components or be administered simultaneously, contemporaneously, or sequentially with other pharmaceutically active compositions as may be additionally needed in the course of providing treatment. Such additional therapeutic agents can include compounds with dopaminergic activity, for example, i) L-DOPA; ii) DOPA decarboxylase inhibitors; and iii) COMT inhibitors.

Those skilled in the art will appreciate that treatment protocols utilizing at least one compound of the invention, for example, a compound of Formula GI or GII, can be varied according to the needs of the subject or patient. Thus, compounds of the invention used in the methods of this invention can be administered in variations of the protocols described above. For example, the compounds of this invention can be administered discontinuously rather than continuously during the treatment cycle.

There follows synthetic schemes by which compounds of the invention may be prepared and examples of preparation of compounds of the invention.

EXAMPLES

In the following examples the following common abbreviations are used for convenience: DMF (dimethylformamide); DCM (dichloromethane); DMB (dimethoxybenzene); EtOAc (ethylacetate); Hex (hexanes); RT (room temperature, nominally about 25° C.); THF (tetrahydrofuran); BSTA (N,O-Bis(trimethylsilyl)acetamide); NMP (N-methyl-2-pyrrolidone); TEA (Trifluoroacetic acid). Other abbreviations employed in the examples and schemes are defined proximal to their point of use.

There follows general synthetic schemes that are useful herein for preparation of intermediates and reagents used in the preparation of 8-ethyl-9-isopropyl-7-methoxy-2-substi- tuted-[1,2,4]triazolo[1,5-c]quinazolin-5-amine(7, 8, or 9-substituted) "right-side" precursor reagents from which compounds of the invention can be prepared.

General Preparation Scheme 1: Preparation of Hydroxy-Alkyl-Hydrazide Reagent

Scheme GP-1

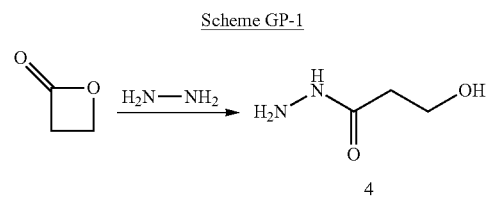

Preparation of 3-hydroxypropanehydrazide (Cmpd-4)

To a stirred methanol (125 mL) solution of oxetan-2-one (15 g, 167 mmol) was added hydrazine hydrate (20.2 mL, 333 mmol). The reaction mixture was heated to 60° C. for 2 hours in a sealed tube, and then cooled to RT. The reaction mixture was transferred to a rotary evaporator, and the solvent was stripped using a 95° C. water bath for 30 minutes. The residue was cooled to room temperature. DCM was added to the residue, precipitating a white crystalline solid that was collected by filtration. The solid was washed with DCM and dried under high vacuum overnight to afford the title product.

There follows examples of preparation of compounds of the invention.

Example 1: Preparation of dimethoxybenzene-protected 2-(5-amino-7-methoxy-[1,2,4]triazolo[1,5-c] quinazolin-2-yl)ethyl methanesulfonates (compound s and preparation of 7-methoxy-2-(2-(3-(methylthio)-5,6-dihydro-[1,2,4]triazolo[4,3-a]pyrazin-7 (8H)-yl)ethyl)-[1,2,4]triazolo[1,5-c]quinazolin-5-amine (Ex-1)

SCHEME 1

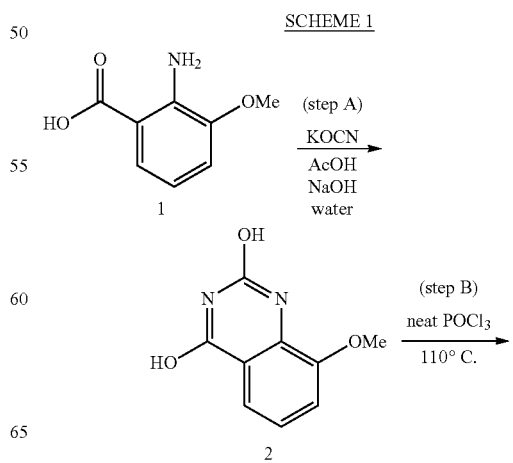

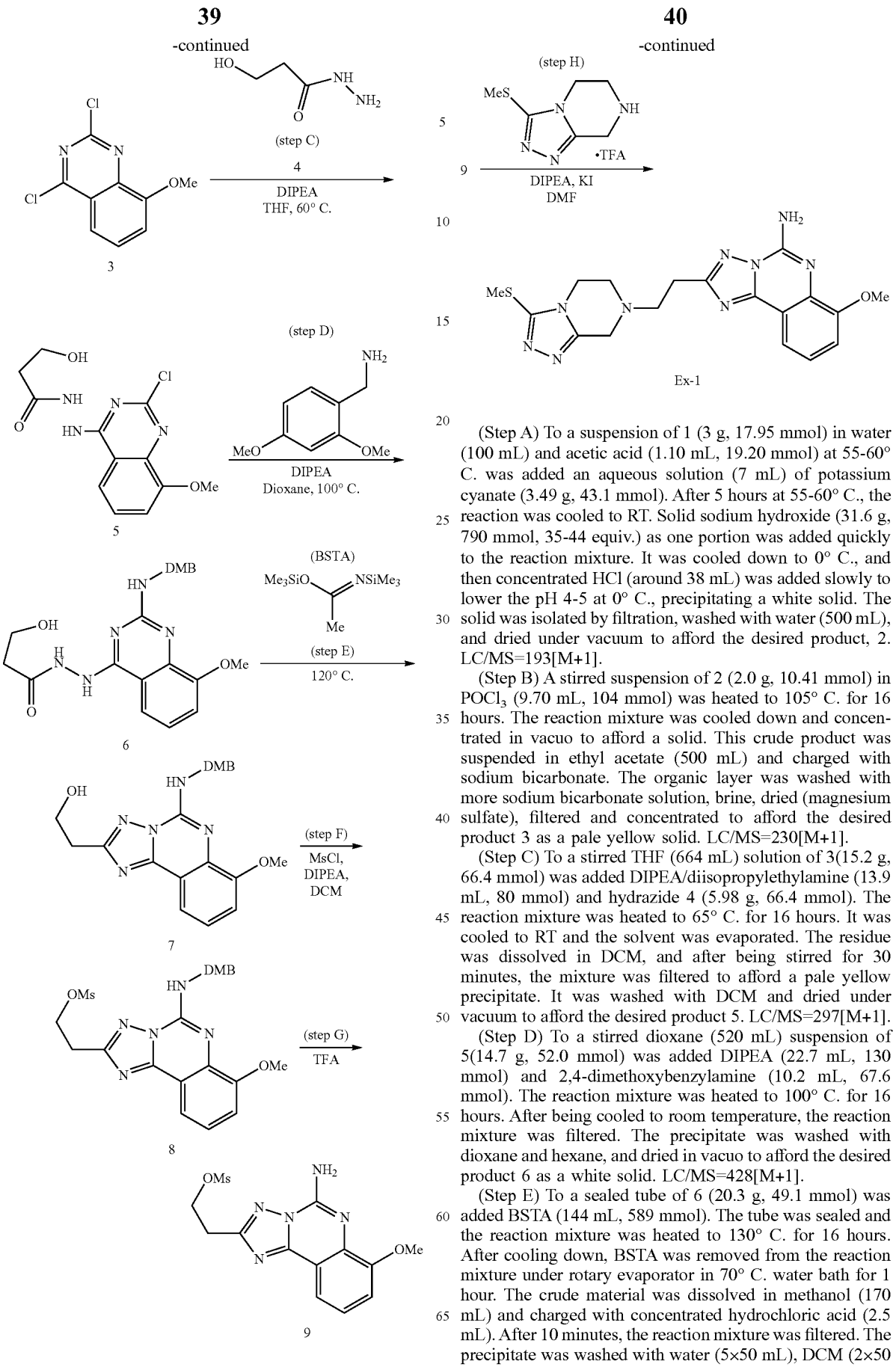

(Step A) To a suspension of 1 (3 g, 17.95 mmol) in water (100 mL) and acetic acid (1.10 mL, 19.20 mmol) at 55-60° C. was added an aqueous solution (7 mL) of potassium cyanate (3.49 g, 43.1 mmol). After 5 hours at 55-60° C., the reaction was cooled to RT. Solid sodium hydroxide (31.6 g, 790 mmol, 35-44 equiv.) as one portion was added quickly to the reaction mixture. It was cooled down to 0° C., and then concentrated HCl (around 38 mL) was added slowly to lower the pH 4-5 at 0° C., precipitating a white solid. The solid was isolated by filtration, washed with water (500 mL), and dried under vacuum to afford the desired product, 2. LC/MS=193[M+1].

(Step B) A stirred suspension of 2 (2.0 g, 10.41 mmol) in $POCl_3$ (9.70 mL, 104 mmol) was heated to 105° C. for 16 hours. The reaction mixture was cooled down and concentrated in vacuo to afford a solid. This crude product was suspended in ethyl acetate (500 mL) and charged with sodium bicarbonate. The organic layer was washed with more sodium bicarbonate solution, brine, dried (magnesium sulfate), filtered and concentrated to afford the desired product 3 as a pale yellow solid. LC/MS=230[M+1].

(Step C) To a stirred THF (664 mL) solution of 3(15.2 g, 66.4 mmol) was added DIPEA/diisopropylethylamine (13.9 mL, 80 mmol) and hydrazide 4 (5.98 g, 66.4 mmol). The reaction mixture was heated to 65° C. for 16 hours. It was cooled to RT and the solvent was evaporated. The residue was dissolved in DCM, and after being stirred for 30 minutes, the mixture was filtered to afford a pale yellow precipitate. It was washed with DCM and dried under vacuum to afford the desired product 5. LC/MS=297[M+1].

(Step D) To a stirred dioxane (520 mL) suspension of 5(14.7 g, 52.0 mmol) was added DIPEA (22.7 mL, 130 mmol) and 2,4-dimethoxybenzylamine (10.2 mL, 67.6 mmol). The reaction mixture was heated to 100° C. for 16 hours. After being cooled to room temperature, the reaction mixture was filtered. The precipitate was washed with dioxane and hexane, and dried in vacuo to afford the desired product 6 as a white solid. LC/MS=428[M+1].

(Step E) To a sealed tube of 6 (20.3 g, 49.1 mmol) was added BSTA (144 mL, 589 mmol). The tube was sealed and the reaction mixture was heated to 130° C. for 16 hours. After cooling down, BSTA was removed from the reaction mixture under rotary evaporator in 70° C. water bath for 1 hour. The crude material was dissolved in methanol (170 mL) and charged with concentrated hydrochloric acid (2.5 mL). After 10 minutes, the reaction mixture was filtered. The precipitate was washed with water (5×50 mL), DCM (2×50 mL), and water. It was then under vacuum to afford the desired product 7 as a pale yellow powder. LC/MS=410 [M+1].

(Step F) To a stirred DCM (73 mL) solution of 7 (3 g, 7.33 mmol) was added triethylamine (3.06 mL, 21.98 mmol) and methanesulfonyl chloride (0.856 mL, 10.99 mmol) at 0° C. The reaction mixture was stirred at RT for 2 hours. Saturated aqueous sodium bicarbonate was added, and the reaction mixture was extracted with DCM. The organic layer was dried (magnesium sulfate), filtered and concentrated. The crude product was purified by column chromatography (ethyl acetate/hexanes) to give the desired product 8. LC/MS=488[M+1].

(Step G) To a round bottom flask of 8 (3.5 g, 7.18 mmol) was added TFA (71.8 mL). The reaction mixture was stirred at 50° C. for 16 hours and cooled down to RT. TFA was evaporated, and the residue was charged with DCM and saturated aqueous sodium bicarbonate solution. The precipitate was collected by filtration, and the aqueous layer was extracted with DCM (×5). The organic extracts were combined with the precipitate and concentrated in vacuo. The crude solid was purified by column chromatography (100% ethyl acetate to 10% MeOH/DCM) to afford the desired product 9 as a pale yellow solid. LC/MS=338 [M+1].

(Step H) To a stirred DMF (637 μL) solution of 9 (100 mg, 0.318 mmol) was added 3-(methylthio)-5,6,7,8-tetrahydro-[1,2,4]triazolo[4,3-α]pyrazine (136 mg, 0.477 mmol), DIPEA (111 μL, 0.637 mmol), and potassium iodide (106 mg, 0.637 mmol). The reaction mixture was heated to 60° C. for 16 hours. After cooling, the reaction mixture was charged with saturated aqueous sodium bicarbonate solution and extracted with DCM. The organic layer was dried (magnesium sulfate), filtered and concentrated. The crude product was purified by column chromatography (1/1 EtOAc/Hex to 10% MeOH/DCM) to give the compound Ex-1, LC/MS=412 [M+1]

Additional compounds of the Formula AI:

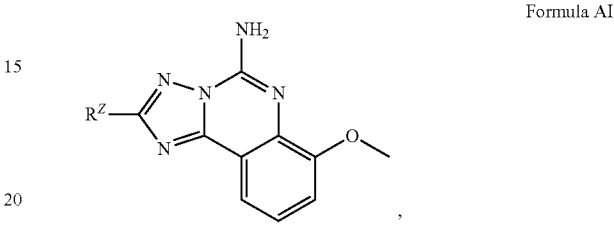

Formula AI where $R^Z$ is elucidated in Table VI, were prepared by using methods described in Scheme I and the example presented above and characterized by LC/MS (data presented also in Table VI). See also Example 16, Scheme 16, for an alternative synthesis scheme for compound Ex-14.

TABLE VI

| Compound No. | Structure | LC-MS |
|---|---|---|
| Ex-2 | 7-(2-(5-amino-7-methoxy-[1,2,4]triazolo[1,5-c]quinazolin-2-yl)ethyl)-N-tert-butyl-5,6,7,8-tetrahydro-[1,2,4]triazolo[4,3-a]pyrazine-3-carboxamide | 465 [M + 1] |
| Ex-3 | 2-(2-(3-bromo-5,6-dihydro-[1,2,4]triazolo[4,3-a]pyrazin-7(8H)-yl)ethyl)-7-methoxy-[1,2,4]triazolo[1,5-c]quinazolin-5-amine | 445 [M + 1] |
| Ex-4 | ethyl 7-(2-(5-amino-7-methoxy-[1,2,4]triazolo[1,5-c]quinazolin-2-yl)ethyl)-5,6,7,8-tetrahydro-[1,2,4]triazolo[4,3-a]pyrazine-3-carboxylate | 438 [M + 1] |

TABLE VI-continued

| Compound No. | Structure | LC-MS |
|---|---|---|
| Ex-5 | 2-(2-(2-chloro-5H-pyrrolo[3,4-b]pyridin-6(7H)-yl)ethyl)-7-methoxy-[1,2,4]triazolo[1,5-c]quinazolin-5-amine | 396 [M + 1] |
| Ex-6 | 2-(2-(4-bromo-5,6-dihydro-1,7-naplithyridin-7(8H)-yl)ethyl)-7-methoxy-[1,2,4]triazolo[1,5-c]quinazolin-5-amine | 455 [M + 1] |
| Ex-7 | 2-(2-(1-cyclopropyl-6,7-dihydro-1H-pyrazolo[4,3-c]pyridin-5(4H)-yl)ethyl)-7-methoxy-[1,2,4]triazolo[1,5-c]iquinazolin-5-amine | 405 [M + 1] |
| Ex-8 | 2-(2-(3-isopropyl-5,6-dihydroimidazo[1,5-a]pyrazin-7(8H)-yl)ethyl)-7-methoxy-[1,2,4]triazolo[1,5-c]quinazolin-5-amine | 407 [M + 1] |
| Ex-9 | 7-methoxy-2-(2-(3-(trifluoromethyl)-6,7-dihydroisoxazolo[4,3-c]pyridin-5(4H)-yl)ethyl)-[1,2,4]triazolo[1,5-c]quinazolin-5-amine | 434 [M + 1] |

TABLE VI-continued

| Compound No. | Structure | LC-MS |
|---|---|---|
| Ex-10 | (7-(2-(5-amino-7-methoxy[1,2,4]triazolo[1,5-c]quinazolin-2-yl)ethyl)-5,6,7,8-tetrahydroimidazo[1,2-a]pyrazin-2-yl)(cyclopropyl)methanone | 433 [M + 1] |
| Ex-11 | 7-methoxy-2-(2-(2-(trifluoromethyl)-5,6-dihydro-1,2,4]triazolo[1,5-a]pyrazin-7(8H)--yl)ethyl)-[1,2,4]triazolo[1,5-c]quinazolin-5-amine | 434 [M + 1] |
| Ex-12 | 2-(2-(2-cyclopropyl-5,6-dihydro-[1,2,4]triazolo[1,5-a]pyrazin-7(8H)-yl)ethyl)-7-methoxy-[1,2,4]triazolo[1,5-c]quinazolin-5-amine | 406 [M + 1] |
| Ex-13 | 2-(2-(3-ethyl-5,6-dihydroimidazo[1,5-a]pyrazin-7(8H)-yl)ethyl)-7-methoxy-[1,2,4]triazolo[1,5-c]quinazolin-5-amine | 393 [M + 1] |
| Ex-14 | 7-methoxy-2-(2-(2-methyl-4H-pyrrolo[3,4-d]thiazol-5(6H)-yl)ethyl)-[1,2,4]triazolo[1,5-c]quinazolin-5-amine | 382 [M + 1] |

TABLE VI-continued

| Compound No. | Structure | LC-MS |
|---|---|---|
| Ex-15 | 6-(2-(5-amino-7-methoxy-[1,2,4]triazolo[1,5-c]quinazolin-2-yl)ethyl)-2-cyclopropyl-4,5,6,7-tetrahydrothieno[2,3-c]pyridine-3-carbonitrile | 446 [M + 1] |
| Ex-16 | 7-methoxy-2-(2-(2-(trifluoromethyl)-6,7-dihydro-3H-imidazo[4,5-c]pyridin-5(4H)-yl)ethyl)-[1,2,4]triazolo[1,5-c]quinazolin-5-amine | 433 [M + 1] |
| Ex-17 | 7-methoxy-2-(2-(3-(trifluoromethyl)-5,6-dihydro[1,2,4]triazolo[4,3-a]pyrazin-7(8H)-yl)ethyl)-[1,2,4]triazolo[1,5-c]quinazolin-5-amine | 434 [M + 1] |
| Ex-18 | 7-methoxy-2-(2-(2-(trifluoromethyl)-5H-pyrrolo[3,4-d]pyrimidin-6(7H)-yl)ethyl)-[1,2,4]triazolo[1,5-c]quinazolin-5-amine | 431 [M + 1] |
| Ex-19 | 2-(2-(5H-pyrrolo[3,4-d]pyrimidin-6(7H)-yl)ethyl)-7-methoxy-[1,2,4]triazolo[1,5-c]quinazolin-5-amine | 363 [M + 1] |

TABLE VI-continued

| Compound No. | Structure | LC-MS |
|---|---|---|
| Ex-20 | 2-(2-(7,8-dihydro-5H-pyrido[2,3-b]azepin-9(6H)-yl)ethyl)-7-methoxy-[1,2,4]triazolo[1,5-c]quinazolin-5-amine | 390 [M + 1] |
| Ex-21 | 2-(2-(2,3-dihydro-1H-pyrrolo[2,3-b]pyridin-1-yl)ethyl)-7-methoxy-[1,2,4]triazolo[1,5-c]quinazolin-5-amine | 362 [M + 1] |
| Ex-22 | 2-(2-(3-ethyl-5,6-dihydro-[1,2,4]triazolo[4,3-a]pyrazin-7(8H)-yl)ethyl)-7-methoxy-[1,2,4]triazolo[1,5-c]quinazolin-5-amine | 394 [M + 1] |
| Ex-23 | 7-methoxy-2-(2-(2-methyl-5H-pyrrolo[3,4-d]pyrimidin-6(7H)-yl)-ethyl)-[1,2,4]triazolo[1,5-c]quinazolin-5-amine | 3377 [M + 1] |
| Ex-24 | 2-(2-(isoindolin-2-yl)ethyl)-7-methoxy-[1,2,4]triazolo[1,5-c]quinazolin-5-amine | 361 [M + 1] |

TABLE VI-continued

| Compound No. | Structure | LC-MS |
|---|---|---|
| Ex-25 | 7-methoxy-2-(2-(2-methyl-6,7-dihydrothiazolo[4,5-c]pyridin-5(4H)-yl)ethyl)-[1,2,4]triazolo[1,5-c]quinazolin-5-amine | 396 [M + 1] |
| Ex-26 | 7-methoxy-2-(2-(2-(trifluoromethyl)-6,7-dihydrothiazolo[4,5-c]pyridin-5(4H)-yl)ethyl)-[1,2,4]triazolo[1,5-c]quinazolin-5-amine | 450 [M + 1] |
| Ex-27 | 7-methoxy-2-(2-(2-methyl-6,7-dihydrooxazolo[4,5-c]pyridin-5(4H)-yl)ethyl)-[1,2,4]triazolo[1,5-c]quinazolin-5-amine | 380 [M + 1] |
| Ex-28 | 7-methoxy-2-(2-(2-methyl-6,7-dihydrooxazolo[5,4-c]pyridin-5(4H)-yl)ethyl)-[1,2,4]triazolo[1,5-c]quinazolin-5-amine | 380 [M + 1] |
| Ex-29 | 7-methoxy-2-(2-(2-methyl-6,7-dihydrothiazolo[5,4-c]pyridin-5(4H)-yl)ethyl)-[1,2,4]triazolo[1,5-c]quinazolin-5-amine | 396 [M + 1] |

TABLE VI-continued

| Compound No. | Structure | LC-MS |
|---|---|---|
| Ex-30 | 2-(2-(2-cyclopropyl-6,7-dihydrothiazolo[5,4-c]pyridin-5(4H)-yl)ethyl)-7-methoxy-[1,2,4]triazolo[1,5-c]quinazolin-5-amine | 422 [M + 1] |
| Ex-31 | 2-(2-(2-cyclopropyl-6,7-dihydrooxazolo[5,4-c]pyridin-5(4H)-yl)ethyl)-7-methoxy[1,2,4]triazolo[1,5-c]quinazolin-5-amine | 406 [M + 1] |
| Ex-32 | 7-methoxy-2-(2-(1-methyl-3-(trifluoromethyl)-6,7-dihydro-1H-pyrazolo[4,3-c]pyridin-5(4H)-yl)ethyl)-[1,2,4]triazolo[1,5-c]quinazolin-5-amine | 447 [M + 1] |
| Ex-33 | 2-(2-(2,3-dihydro-1H-imidazo[1,2-b]pyrazol-1-yl)ethyl)-7-methoxy-[1,2,4]triazolo[1,5-c]quinazolin-5-amine | 351 [M + 1] |

TABLE VI-continued

| Compound No. | Structure | LC-MS |
|---|---|---|
| Ex-34 | 7-methoxy-2-(2-2-phenylpyrrolo[3,4-d]imidazol-5(1H,4H,6H)-yl)ethyl)-[1,2,4]triazolo[1,5-c]quinazolin-5-amine | 427 [M + 1] |
| Ex-35 | 2-(2-(6,7-dihydroisoxazolo[4,5-c]pyridin-5(4H)-yl)ethyl)-7-methoxy-[1,2,4]triazolo[1,5-c]quinazolin-5-amine | 366 [M + 1] |
| Ex-36 | 2-(2-(6,7-dihydro-1H-pyrazolo[4,3-c]pyridin-5(4H)-yl)ethyl)-7-methoxy-[1,2,4]triazolo[1,5-c]quinazolin-5-amine | 365 [M + 1] |
| Ex-37 | 7-methoxy-2-(2-(3-methyl-6,7-dihydro-1H-pyrazolo[4,3-c]pyridin-5(4H)-yl)ethyl)-[1,2,4]triazolo[1,5-c]quinazolin-5-amine | 379 [M + 1] |

TABLE VI-continued

| Compound No. | Structure | LC-MS |
|---|---|---|
| Ex-38 | 7-methoxy-2-(2-(3-(trifluoromethyl)-6,7-dihydro-1H-pyrazolo[4,3-c]pyridin-5(4H)-yl)ethyl)-[1,2,4]triazolo[1,5-c]quinazolin-5-amine | 433 [M + 1] |
| Ex-39 | 2-(2-(6,7-dihydrothieno[3,2-c]pyridin-5(4H)-yl)ethyl-7-methoxy-[1,2,4]triazolo[1,5-c]quinazolin-5-amine | 381 [M + 1] |
| Ex-40 | 2-(2-(3-cyclopropyl-4,5-dihydro-1H-pyrazolo[3,4-c]pyridin-6(7H)-yl)ethyl)-7-methoxy-[1,2,4]triazolo[1,5-c]quinazolin-5-amine | 405 [M + 1] |
| Ex-41 | 7-methoxy-2-(2-(2-methyl-6,7-dihydropyrazolo[1,5-a]pyrazin-5(4H)-yl)ethyl)-[1,2,4]triazolo[1,5-c]quinazolin-5-amine | 379 [M + 1] |
| Ex-42 | 7-methoxy-2-(2-(3-(trifluoromethyl)-4,5-dihydro-1H-pyrazolo[3,4-c]pyridin-6(7H)-yl)ethyl)-[1,2,4]triazolo[1,5-c]quinazolin-5-amine | 433 [M + 1] |

TABLE VI-continued

| Compound No. | Structure | LC-MS |
|---|---|---|
| Ex-43 | 7-methoxy-2-(2-(1-methyl-3-(trifluoromethyl)-6,7-dihydro-1H-pyrazolo[4,3-b]pyridin-4(5H)-yl)ethyl)-[1,2,4]triazolo[1,5-c]quinazolin-5-amine | 447 [M + 1] |
| Ex-44 | 2-(2-(6-fluoro-3,4-dihydroisoquinolin-2(1H)-yl)ethyl)-7-methoxy-[1,2,4]triazolo[1,5-c]quinazolin-5-amine | 393 [M + 1] |
| Ex-45 | 2-(2-(5,6-dihydro-1,7-naphthyridin-7(8H)-yl)ethyl)-7-methoxy-[1,2,4]triazolo[1,5-c]quinazolin-5-amine | 376 [M + 1] |
| Ex-46 | 7-methoxy-2-(2-(5-(trifluoromethyl)isoindolin-2-yl)ethyl)-[1,2,4]triazolo[1,5-c]quinazolin-5-amine | 429 [M + 1] |
| Ex-48 | 2-(2-(5-fluoroisoindolin-2-yl)ethyl)-7-methoxy-[1,2,4]triazolo[1,5-c]quinazolin-5-amine | 379 [M + 1] |

TABLE VI-continued

| Compound No. | Structure | LC-MS |
|---|---|---|
| Ex-49 | 2-(2-(5H-pyrrolo[3,4-b]pyridin-6(7H)-yl)ethyl)-7-methoxy-[1,2,4]triazolo[1,5-c]quinazolin-5-amine | 362 [M + 1] |
| Ex-50 | 7-methoxy-2-(2-(3-phenylpyrrolo[3,4-c]pyrazol-5(1H,4H,6H)-yl)ethyl)-[1,2,4]triazolo[1,5-c]quinazolin-5-amine | 427 [M + 1] |
| Ex-51 | 7-methoxy-2-(2-(pyrrolo[3,4-c]pyrazol-5(1H,4H,6H)--yl)ethyl)-[1,2,4]triazolo[1,5-c]quinazolin-5-amine | 351 [M + 1] |
| Ex-52 | 2-(2-(3-cyclopropyl-6,7-dihydro-1H-pyrazolo[4,3-b]pyridin-4(5H)-yl)ethyl)-7-methoxy[1,2,4]triazolo[1,5-c]quinazolin-5-amine | 405 [M + 1] |

TABLE VI-continued

| Compound No. | Structure | LC-MS |
|---|---|---|
| Ex-53 | 2-(2-(5,6-dihydropyrido[3,4-d]pyrimidin-7(8H)-yl)ethyl)-7-methoxy-[1,2,4]triazolo[1,5-c]quinazolin-5-amine | 377 [M + 1] |
| Ex-54 | 2-(2-(7,8-dihydropyrido[4,3-d]pyrimidin-6(5H)-yl)ethyl)-7-methoxy-[1,2,4]triazolo[1,5-c]quinazolin-5-amine | 377 [M + 1] |
| Ex-55 | 2-(2-(7,8-dihydropyrido[4,3-b]pyrazin-6(5H)-yl)ethyl)-7-methoxy-[1,2,4]triazolo[1,5-c]quinazolin-5-amine | 377 [M + 1] |
| Ex-56 | 2-(2-(6,7-dihydrothiazolo[5,4-c]pyridin-5(4H)-yl)ethyl)-7-methoxy-[1,2,4]triazolo[1,5-c]quinazolin-5-amine | 382 [M + 1] |
| Ex-57 | 2-(2-(6,7-dihydrothiazolo[4,5-c]pyridin-5(4H)-yl)ethyl)-7-methoxy-[1,2,4]triazolo[1,5-c]quinazolin-5-amine | 382 [M + 1] |

TABLE VI-continued

| Compound No. | Structure | LC-MS |
|---|---|---|
| Ex-58 | 7-methoxy-2-(2-(2-(trifluoromethyl)-5,6-dihydroimidazo[1,2-a]pyrazin-7(8H)-yl)ethyl)-[1,2,4]triazolo[1,5-c]quinazolin-5-amine | 433 [M + 1] |
| Ex-59 | 2-(2-(6,7-dihydropyrazolo[1,5-a]pyrimidin-4(5H)-yl)ethyl)-7-methoxy-[1,2,4]triazolo[1,5-c]quinazolin-5-amine | 365 [M + 1] |
| Ex-60 | 7-methoxy-2-(2-(2-methyl-7,8-dihydro-4H-pyrazolo[1,5-a][1,4]diazepin-5(6H)-yl)ethyl)-[1,2,4]triazolo[1,5-c]quinazolin-5-amine | 393 [M + 1] |
| Ex-61 | 5-(2-(5-amino-7-methoxy-[1,2,4]triazolo[1,5-c]quinazolin-2-yl)ethyl)-5,6,7,8-tetrahydro-4H-pyrazolo[1,5-a][1,4]diazepine-2-carbonitrile | 404 [M + 1] |

TABLE VI-continued
| Compound No. | Structure | LC-MS |
|---|---|---|
| Ex-62 | 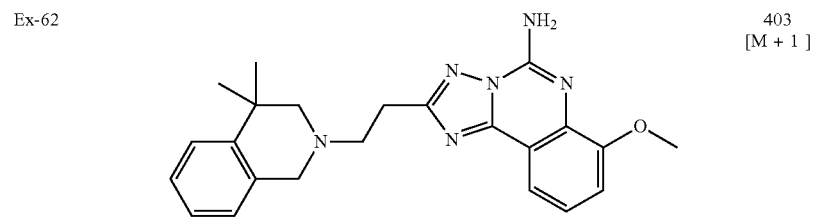<br>2-(2-(4,4-dimethyl-3,4-dihydroisoquinolin-2(1H)-yl)ethyl)-7-methoxy-[1,2,4]triazolo[1,5-c]quinazolin-5-amine | 403 [M + 1] |
| Ex-172 | 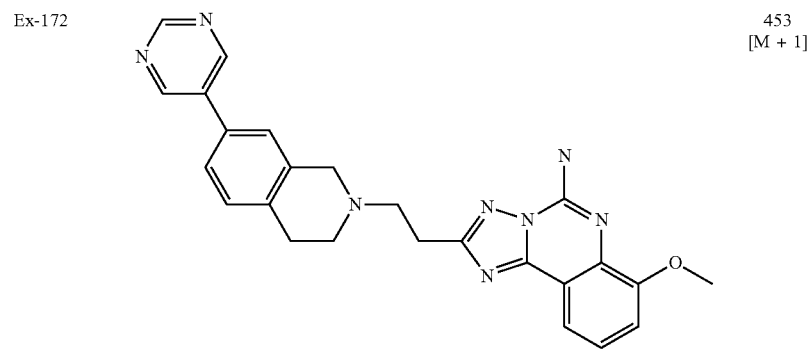<br>7-methoxy-2-(2-(7-(pyrimidin-5-yl)-3,4-dihydroisoquinolin-2(1H)-yl)ethyl)-[1,2,4]triazolo[1,5-c]quinazolin-5-amine | 453 [M + 1] |
| Ex-246 | 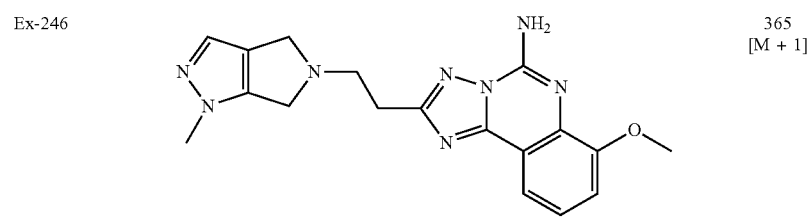<br>7-methoxy-2-(2-(1-methylpyrrolo[3,4-c]pyrazol-5(1H,4H,6H)-yl)ethyl)-[1,2,4]triazolo[1,5-c]quinazolin-5-amine | 365 [M + 1] |

Example 2: Preparation of 7-methoxy-2-(2-(2-(4-methylpiperazin-1-yl)-5H-pyrrolo[3,4-b]pyridin-6(7H)-yl)ethyl)-[1,2,4]triazolo[1,5-c]quinazolin-5-amine (Ex-63)

SCHEME 2

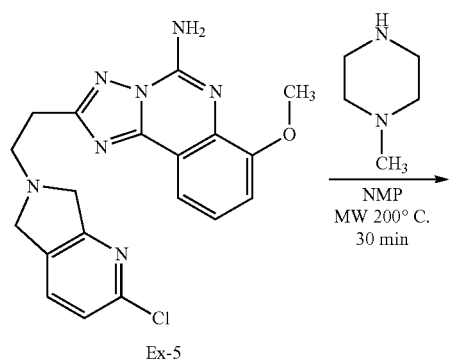

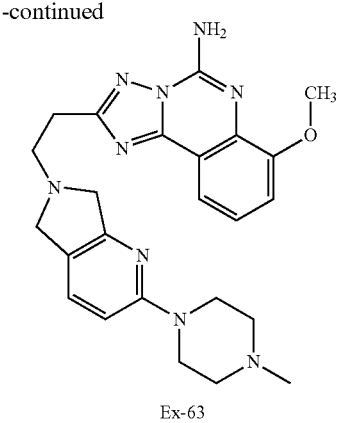

To a microwave tube was added 2-(2-(2-chloro-5H-pyrrolo[3,4-b]pyridin-6(7H)-yl)ethyl)-7-methoxy-[1,2,4]triazolo[1,5-c]quinazolin-5-amine (compound Ex-5, prepared in Example 1, (30 mg, 0.076 mmol), 1-methylpiperazine (1.5 mL, 13.53 mmol), and NMP (500 µL). The reaction mixture was microwaved at 200° C. for 1.5 hr. The crude reaction mixture was purified by reverse phase column (Water+0.1% TFA/ACN+0.1% TFA) to give the desired product, Ex-63, LC/MS=474 [M+1].

The compounds presented in Table VII were prepared by using methods described in Scheme 2 and Example 2. These compounds were characterized by LC/MS, which data is also presented in Table VII.

TABLE VII

| Compound No. | Structure | LC-MS |
|---|---|---|
| Ex-64 | 7-methoxy-2-(2-(2-morpholino-5H-pyrrolo[3,4-b]pyridin-6(7H)-yl)ethyl)-[1,2,4]triazolo[1,5-c]quinazolin-5-amine | 447 [M + 1] |
| Ex-65 | 7-methoxy-2-(2-(2-(pyrrolidin-1-yl)-5H-pyrrolo[3,4-b]pyridin-6(7H)-yl)ethyl)-[1,2,4]triazolo[1,5-c]quinazolin-5-amine | 431 [M + 1] |

TABLE VII-continued

| Compound No. | Structure | LC-MS |
|---|---|---|
| Ex-66 | 2-(2-(2-(4-ethylpiperazin-1-yl)-5H-pyrrolo[3,4-b]pyridin-6(7H)-yl)ethyl)-7-methoxy-[1,2,4]triazolo[1,5-c]quinazolin-5-amine | 474 [M + 1] |
| Ex-68 | 2-(2-(2-(2,2-dimethylmorpholino)-5H-pyrrolo[3,4-b]pyridin-6(7H)-yl)ethyl)-7-methoxy-[1,2,4]triazolo[1,5-c]quinazolin-5-amine | 475 [M + 1] |
| Ex-69 | 2-(2-(2-((2S,6R)-2,6-dimethylmorpholino)-5H-pyrrolo[3,4-b]pyridin-6(7H)-yl)ethyl)-7-methoxy-[1,2,4]triazolo[1,5-c]quinazolin-5-amine | 475 [M + 1] |
| Ex-70 | 2-(2-(2-(4-(cyclopropylmethyl)piperazin-1-yl)-5H-pyrrolo[3,4-b]pyridin-6(7H)-yl)ethyl)-7-methoxy-[1,2,4]triazolo[1,5-c]quinazolin-5-amine | 500 [M + 1] |
| Ex-71 | 2-(2-(2-(4-(4-fluorophenyl)piperazin-1-yl)-5H-pyrrolo[3,4-b]pyridin-6(7H)-yl)ethyl)-7-methoxy-[1,2,4]triazolo[1,5-c]quinazolin-5-amine | 540 [M + 1] |

TABLE VII-continued

| Compound No. | Structure | LC-MS |
|---|---|---|
| Ex-72 | 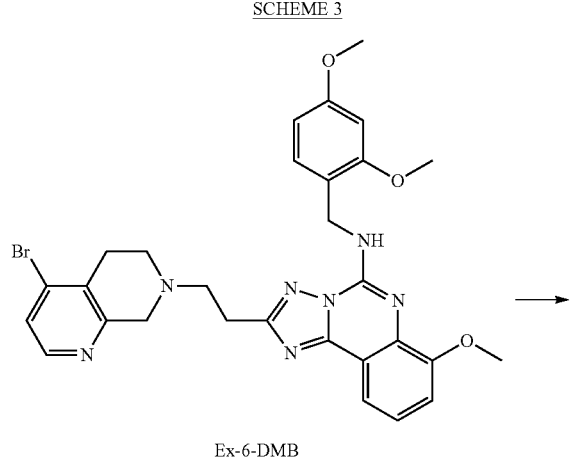<br>7-methoxy-2-(2-(2-(4-morpholinopiperidin-1-yl)-5H-pyrrolo[3,4-b]pyridin-6(7H)-yl)ethyl)-[1,2,4]triazolo[1,5-c]quinazolin-5-amine | 530 [M + 1] |

Example 3: Preparation of dimethoxybenzene-protected 2-(5-amino-7-methoxy-[1,2,4]triazolo[1,5-c]quinazolin-2-yl)ethyl methanesulfonates ("right-side" precursor compounds) and preparation of 2-(2-(4-(4-ethylpiperazin-1-yl)-5,6-dihydro-1,7-naphthyridin-7(8H)-yl)ethyl)-7-methoxy-[1,2,4]triazolo[1,5-c]quinazolin-5-amine (Ex-73)

SCHEME 3

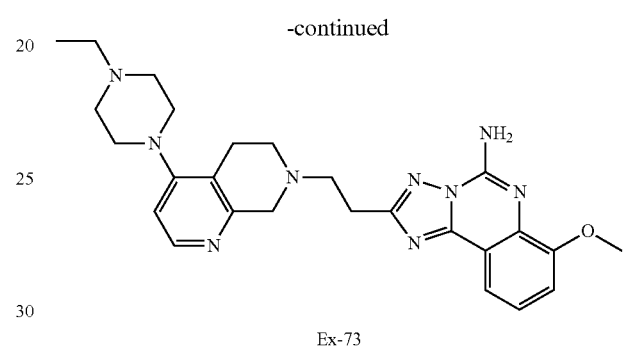

Ex-73

(Step A) To a stirred suspension of dimethylbenzene (DMB)-protected compound Ex-6 (prepared in Example 1, 45 mg, 0.074 mmol), 1-ethylpiperazine (19 μL, 0.15 mmol), potassium tert-butoxide (21 mg, 0.19 mmol) and 2-dicyclohexylphosphino-2',6'-di-i-propoxy-1,1'-biphenyl (7.0 mg, 0.015 mmol) in dioxane (573 μL) was added tris(dibenzylideneacetone)dipalladium(0) (6.8 mg, 7.4 μmol). The reaction mixture was heated at 100° C. overnight. The solvent was evaporated and the crude was diluted with EtOAc. The organic layer was washed with sat. NaCl (aq), dried over MgSO$_4$, filtered and concentrated. The crude product was purified by column chromatography (MeOH:DCM=1/1 to 50% MeOH) to give N-(2,4-dimethoxybenzyl)-2-{2-[4-(4-ethylpiperazin-1-yl)-5,8-dihydro-1,7-naphthyridin-7(6H)-yl]ethyl}-7-methoxy[1,2,4]triazolo[1,5-c]quinazolin-5-amine, LC/MS=638[M+1].

(Step B) To a round bottom flask of N-(2,4-dimethoxybenzyl)-2-{2-[4-(4-ethylpiperazin-1-yl)-5,8-dihydro-1,7-naphthyridin-7(6H)-yl]ethyl}-7-methoxy[1,2,4]triazolo[1,5-c]quinazolin-5-amine (25.1 mg, 0.039 mmol) was added TFA (400 μL). The reaction mixture was stirred at room temperature overnight. TFA was evaporated, diluted with MeOH, evaporated again. Rediluted with DCM and neutralized with 7N NH$_3$ in MeOH, and solvent was evaporated. The crude product was purified by prep-TLC (10% MeOH in DCM) to give compound Ex-73, which was characterized by LC/MS=488 [M+1].

The compounds presented in Table VIII were prepared by using methods described in Scheme 3 and Example 3. These compounds were characterized by LC/MS, which data is also presented in Table VIII.

TABLE VIII

| Compound No. | Structure | LC-MS |
|---|---|---|
| Ex-74 | 2-(2-(4-(diethylamino)-5,6-dihydro-1,7-naphthyridin-7(8H)-yl)ethyl)-7-methoxy-[1,2,4]triazolo[1,5-c]quinazolin-5-amine | 447 [M + 1] |
| Ex-76 | 2-(2-(4-(3,3-difluoropyrrolidin-1-yl)-5,6-dihydro-1,7-naphthyridin-7(8H)-yl)ethyl)-7-methoxy-[1,2,4]triazolo[1,5-c]quinazolin-5-amine | 481 [M + 1] |

Example 4: Preparation of 2-(5-amino-7-methoxy-[1,2,4]triazolo[1,5-c]quinazolin-2-yl)-1-(5H-pyrrolo[3,4-b]pyridin-6(7H)-yl) (Ex-77)

SCHEME 4

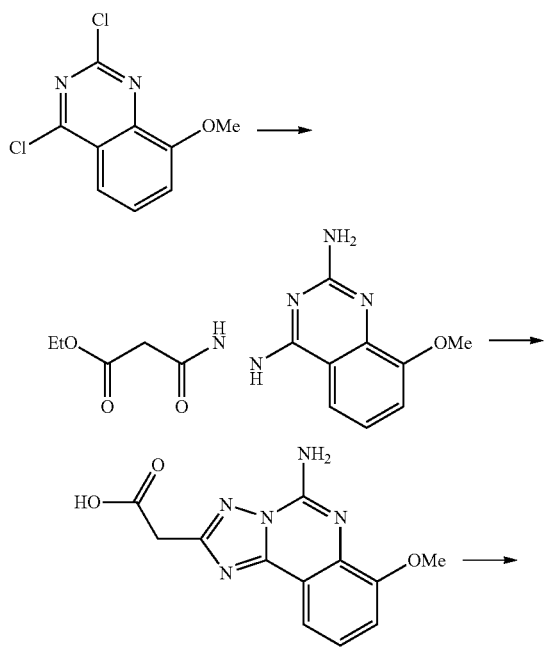

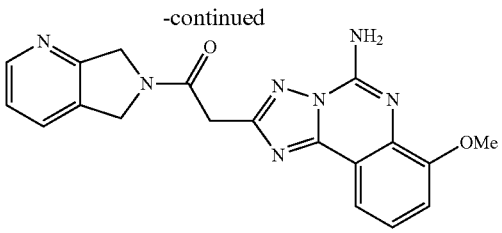

Ex-77

Step A: ethyl 3-[2-(2-amino-8-methoxyquinazolin-4-yl)hydrazinyl]-3-oxopropanoate 2,4-dichloro-8-methoxyquinazoline was treated sequentially with ethyl 3-hydrazino-3-oxopropionate (DIPEA, THF, 60° C., overnight) and NH₃ (2M in i-PrOH, 100° C. overnight in a sealed tube) to give the title compound and the corresponding isopropyl ester (~3:1).

Step B: (5-amino-7-methoxy[1,2,4]triazolo[1,5-c]quinazolin-2-yl)acetic acid

The mixture of ethyl and isopropyl esters was sequentially reacted with BSTA (120° C., 3 h) and LiOH (THF, water, room temperature, overnight) to provide the title compound, LCMS (M+H)=274.

Step C: 2-(5-amino-7-methoxy[1,2,4]triazolo[1,5-c]quinazolin-2-yl)-1-(5,7-dihydro-6H-pyrrolo[3,4-b]pyridin-6-yl)ethanone A mixture of (5-amino-7-methoxy[1,2,4]triazolo[1,5-c]quinazolin-2-yl)acetic acid (0.050 g, 0.161 mmol), 6,7- dihydro-5H-pyrrolo[3,4-b]pyridine dihydrochloride (0.047 g, 0.24 mmol), DIPEA (0.141 ml, 0.807 mmol), and 1-propanephosphonic acid cyclic anhydride (0.144 mL, 0.242 mmol) in DCM (5 mL) was stirred at room temperature overnight and then diluted with water and DCM. The organic layer was filtered and concentrated. The residue was purified by preparative reverse phase HPLC (eluting with 10-95% Acetonitrile/Water+0.1% TFA (2.0 mL/min) over 10 min.) to give compound, Ex-77 (a light yellow solid), which was characterized by LCMS (M+H)=376.

Compound Ex-78 presented in Table IX was prepared using methods described in Example 4 and Scheme 4:

Step A: 2-(2-(5H-pyrrolo[3,4-b]pyridin-6(7H)-yl) ethyl)-5-amino-[1,2,4]triazolo[1,5-c]quinazolin-7-ol To a solution of compound Ex-49 prepared in Example 1, above, (185 mg, 0.512 mmol) in DMF (4 mL) was added sodium methylthiolate (71.8 mg, 1.024 mmol). Reaction mixture was stirred in a sealed tube at 100° C. for 18 h. The reaction mixture was diluted with DCM, washed with H$_2$O. The organic layer was separated and dried over MgSO$_4$, filtered and concentrated in vacuo. Purification by preparative TLC (DCM: MeOH (7N NH$_3$) 1:20) to yield the title compound, LC/MS=348 [M+1].

TABLE IX

| Compound No. | Structure | LC-MS |
|---|---|---|
| Ex-78 | 2-(5-amino-7-methoxy-[1,2,4]triazolo[1,5-c]quinazolin-2-yl)-1-(4,5-dihydro-1H-benzo[d]azepin-3(2H)-yl)ethanone | 403 [M + 1] |

Example 5: Preparation of 2-(2-(5H-pyrrolo[3,4-b]pyridin-6(7H)-yl)ethyl)-7-(fluoromethoxy)-[1,2,4]triazolo[1,5-c]quinazolin-5-amine (Ex-79)

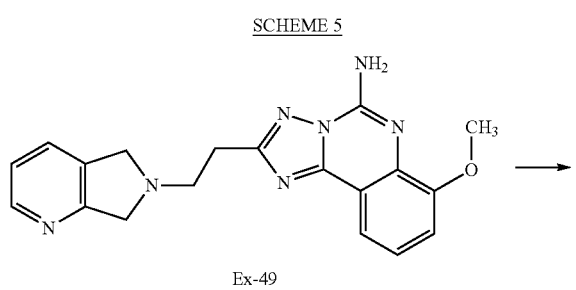

Step B: 2-(2-(5H-pyrrolo[3,4-b]pyridin-6(7H)-yl) ethyl)-7-(fluoromethoxy)-[1,2,4]triazolo[1,5-c]quinazolin-5-amine To a solution of 2-(2-(5H-pyrrolo[3,4-b]pyridin-6(7H)-yl)-5-amino-[1,2,4]triazolo[1,5-c]quinazolin-7-ol (20 mg, 0.058 mmol) in acetone (2 mL) was added fluoromethyl methanesulfonate (17.6 mg, 0.086 mmol) and Cs$_2$CO$_3$ (56.3 mg, 0.173 mmol). The reaction mixture was stirred in a sealed tube at 40° C. for 48 h, cooled to room temperature, filtered through diatomaceous earth, washing with DCM and MeOH. The filtrate was concentrated in vacuo. Purification by preparative TLC (DCM: MeOH (7N NH$_3$) 1:20) yielded compound, Ex-79 which was characterized by LC/MS=380 [M+1].

Example 6: Preparation of 2-(7-chloro-5-(2,4-dimethoxybenzylamino)-[1,2,4]triazolo[1,5-c]quinazolin-2-yl)acetaldehyde as "right-side" precursor and preparation of 7-chloro-2-(2-(5-fluoroisoindolin-2-yl)ethyl)-[1,2,4]triazolo[1,5-c]quinazolin-5-amine (Ex-80) therefrom

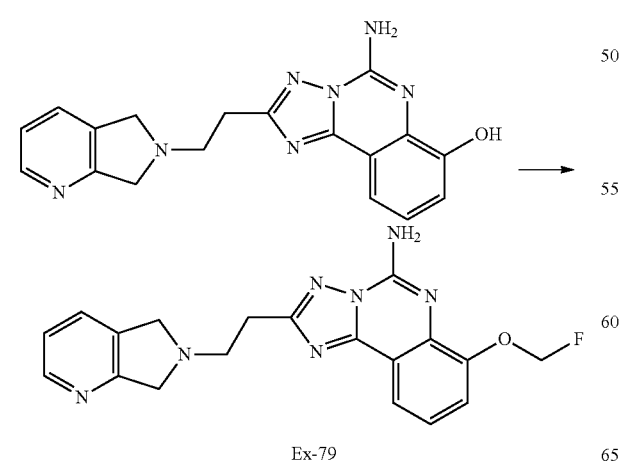

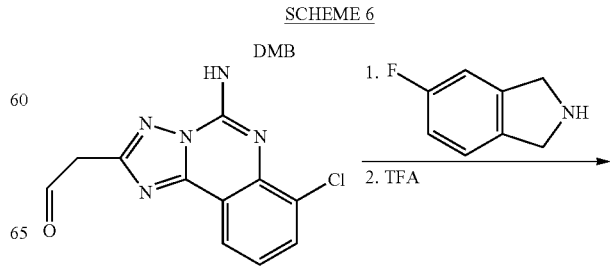

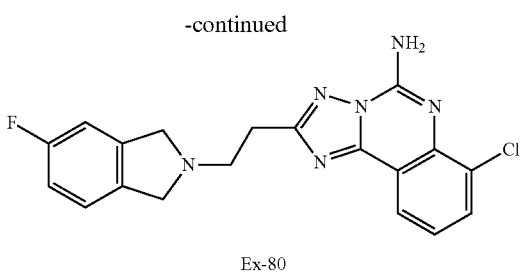

Ex-80

Step A: 3,3-dimethoxypropanehydrazide

The mixture of methyl 3,3-dimethoxypropanoate (6 g, 83.3 mmol) and 80% hydrazine hydrate (52 mL, 833 mmol, 10 equiv.) was heated at 120° C. for 6 hours. The excess of hydrazine was removed on a rotary evaporator. The residue was dissolved in DCM (30 mL). The remaining aqueous layer was extracted with DCM (30 mL). The organic layers were combined, ad concentrated to a volume of 30 mL. The title compound was precipitated by the addition of petroleum ether to afford a white solid. The product was characterized by proton NMR: $^1$H-NMR (DMSO-d6, 400 MHz) δ 9.02 (s, 1H), 4.70 (t, J=5.2 Hz, 1H), 4.2. (s, 2H), 3.22. (s, 6H), 2.33 (d, J=5.2 Hz, 2H).

Step B: 8-chloroquinazoline-2,4-diol

The mixture of 2-amino-3-chlorobenzoic acid (13 g, 75.8 mmol) and urea (27.3 g, 454 mmol, 6 equiv.) was stirred at 200° C. for 2 hours, cooled to 120° C. Water (500 mL) was added in small portions. The solid was filtered, washed with water and EtOAc, and dried in oven (100° C.) to afford the desired compound as a brown solid, which was characterized by LC/MS. LC-MS: m/z (M+1)–197.

Step C: 2,4,8-trichloroquinazoline

8-Chloroquinazoline-2,4-diol (step B, 15 g, 75.8 mmol) was added to POCl$_3$ (70 mL, 763 mmol, 10 equiv.) in small portions. Dimethylaniline (3.7 g, 30.5 mmol, 0.4 equiv.) was added. The reaction mixture was stirred in 140° C. for 16 hours. The mixture was cooled to room temperature, and added drop wise to ice-water (500 mL). The precipitate was collected and washed with ice-water. The solid was dissolved in DCM (500 mL), dried over MgSO$_4$, filtered, and concentrated to give the crude product, which was purified by silica column chromatography (petroleum ether: EtOAc=7:1) to afford the title compound as a yellow solid which was characterized by LC/MS. LC-MS: m/z (M+1) =233.

Step D: N'-(2,8-dichloroquinazolin-4-yl)-3,3-dimethoxypropanehydrazide

The mixture of 2,4,8-trichloroquinazoline (step C, 4.0 g, 17.2 mmol), DIPEA (15 mL, 86.1 mmol) and 3,3-dimethoxypropanehydrazide (step A, 3.1 g, 20.7 mmol) in 1,4-dioxane (50 mL) was stirred at 40° C. for 2 hours, and then concentrated. The residue was partitioned between DCM (50 mL) and aqueous NaHCO$_3$ (50 mL). The organic layer was washed with water and concentrated to get the title compound as a yellow solid which was characterized by LC/MS. LC-MS: m/z (M+1)=345.

Step E: N'-(8-chloro-2-(2,4-dimethoxybenzylamino) quinazolin-4-yl)-3,3-dimethoxypropanehydrazide The mixture of N'-(2,8-dichloroquinazolin-4-yl)-3,3-dimethoxypropanehydrazide (step D, 5.9 g, 17.2 mmol), DIPEA (6 mL, 34.3 mmol), and (2,4-dimethoxyphenyl) methanamine (3.1 mL, 20.6 mmol) in 1,4-dioxane (50 mL) was stirred at 80° C. overnight. After concentration, the residue was partitioned between DCM (100 mL) and aqueous NaHCO$_3$ (100 mL). The organic layer was washed with water and concentrated to get the title compound as a yellow solid which was characterized by LC/MS. LC-MS: m/z (M+1)=476.

Step F: 7-chloro-N-(2,4-dimethoxybenzyl)-2-(2,2-dimethoxyethyl)-[1,2,4]triazolo[1,5-c]quinazolin-5-amine The solution of N'-(8-chloro-2-(2,4-dimethoxybenzylamino)quinazolin-4-yl)-3,3-dimethoxypropanehydrazide (step E, 7.8 g, 16.4 mmol) in BSA (30 mL) was stirred at 140° C. overnight. The mixture was then concentrated by rotovap at 70° C. to remove all BSA. The residue was added methanol (50 mL), stirred in cold ice bath for a while. The resulting suspension was filtered, dried under vacuum to obtain the title compound as a yellow solid which was characterized by proton NMR and LC/MS. $^1$H-NMR (DMSO-d6, 400 MHz) δ 8.49 (d, J=6 Hz, 1H), 8.10 (d, J=7.6 Hz, 1H), 7.79 (t, J=8 Hz, 1H), 7.37-7.26 (m, 2H), 6.54 (d, J=1.6 Hz, 1H), 6.25 (t, J=8 Hz, 1H), 4.99 (t, J=12 Hz, 1H), 4.70 (d, J=5.6 Hz, 2H), 3,82 (s, 3H), 3.70 (s, 3H), 3.34 (s, 6H), 3.18 (d, J=6 Hz, 2H), LC-MS: m/z (M+1)=458.

Step G: 2-(7-chloro-5-(2,4-dimethoxybenzylamino)-[1,2,4]triazolo[1,5-c]quinazolin-2-yl)acetaldehyde The mixture of 7-chloro-N-(2,4-dimethoxybenzyl)-2-(2,2-dimethoxyethyl)-[1,2,4]triazolo[1,5-c]quinazolin-5-amine (step F, 2.5 g, 5.5 mmol) and TsOH (470 mg, 2.7 mmol) in acetone/H$_2$O (20 mL/2 mL) was stirred at 60° C. under argon overnight. The mixture was then cooled to room temperature, and concentrated under reduced pressure at room temperature. The residue was dried in vacuum to obtain the title compound as a crude product, which was used in next step without purification, LC-MS: m/z (M+1) =412.

Step H: 7-chloro-5-(2,4-dimethoxyphenyl)-2-(2-(5-fluoroisoindolin-2-yl)ethyl)-[1,2,4]triazolo[1,5-c] quinazoline To a THF (5 mL) mixture of 2-(7-chloro-5-(2,4-dimethoxybenzylamino)-[1,2,4]triazolo[1,5-c]quinazolin-2-yl) acetaldehyde (step G, 250 mg, 0.6 mmol) and 5-fluoroisoindoline (167 mg, 1.2 mmol) was added tetraethoxytitaniutn (0.1 mL). The reaction mixture was stirred at 20° C. for 1 hour. Sodium cyanoborohydride (192 mg, 3.0 mmol) was then added to the reaction mixture, which was stirred at 20° C. for 16 hours. The mixture was concentrated to afford the title compound as white solid which was characterized by LC/MS. LCMS: m/z (M+1)=530.

Step I: 7-chloro-2-(2-(5-fluoroisoindolin-2-yl)ethyl)-[1,2,4]triazolo[1,5-c]quinazolin-5-amine A trifluoracetic acid (5 mL) solution of 7-chloro-5-(2,4-dimethoxyphenyl)-2-(2-(5-fluoroisoindolin-2-yl)ethyl)-[1, 2,4]triazolo[1,5-c]quinazoline (step H, 320 mg, 0.6 mmol) was stirred at 50° for 16 hours. The solution was evaporated to dryness, then purified by silica chromatography using MeOH/CH$_2$Cl$_2$ (1:10) eluent to yield compound, Ex-80, as a white solid which was characterized by LC/MS. LCMS: m/z (M+1)=383.

The synthesis of Example 6 was employed with appropriate "left-side" reagents to prepare the compounds presented in Table X. These compounds were characterized by LC/MS, which data is also reported in Table X.

TABLE X

| Compound No. | Structure | LC-MS |
|---|---|---|
| Ex-82 | 7-chloro-2-(2-(3,4-dihydroquinolin-1(2H)-yl)ethyl)-[1,2,4]triazolo[1,5-c]quinazolin-5-amine | 379 [M + 1] |

Using the procedure of Scheme 6 and Example 6, Compound Ex-83, 2-[2-(5,7-dihydro-6H-pyrrolo[3,4-b]pyridin-6-yl)ethyl]-7-fluoro[1,2,4]triazolo[1,5-c]quinazolin-5-amine:

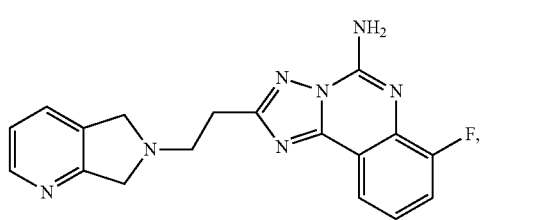

Ex-83 was prepared by substituting 2-amino-3-fluorobenzoic acid for 2-amino-3-chlorobenzoic acid in step B and 6,7-dihydro-5H-pyrrolo[3,4-b]pyridine for 5-fluoroisoindoline in step H. Compound Ex 83 was characterized by LC/MS: m/z (M+1)=350.

Additional compounds prepared using this same procedure are presented in Table XI, below, along with the characteristic LC/MS data.

TABLE XI

| Compound No. | Structure | LC-MS |
|---|---|---|
| Ex-84 | 2-(2-(3,4-dihydroquinolin-1(2H)-yl)ethyl)-7-fluoro-[1,2,4]triazolo[1,5-c]quinazolin-5-amine | 363 [M + 1] |
| Ex-85 | 7-fluoro-2-(2-(5-fluoroisoindolin-2-yl)ethyl)-[1,2,4]triazolo[1,5-c]quinazolin-5-amine | 367 [M + 1] |

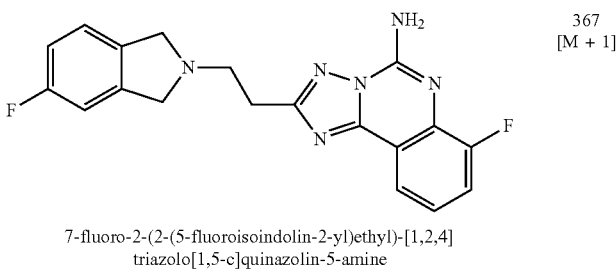

TABLE XI-continued

| Compound No. | Structure | LC-MS |
|---|---|---|
| Ex-86 | 2-(2-(3-ethyl-5,6-dihydro-[1,2,4]triazolo[4,3-a]pyrazin-7(8H)-yl)ethyl)-7-fluoro-[1,2,4]triazolo[1,5-c]quinazolin-5-amine | 382 [M + 1] |
| Ex-87 | 2-(2-(3,4-dihydroisoquinolin-2(1H)-yl)ethyl)-7-fluoro-[1,2,4]triazolo[1,5-c]quinazolin-5-amine | 363 [M + 1] |
| Ex-88 | 7-fluoro-2-(2-(2-(trifluoromethyl)-5H-pyrrolo[3,4-d]pyrimidin-6(7H)-yl)ethyl)-[1,2,4]triazolo[1,5-c]quinazolin-5-amine | 419 [M + 1] |
| Ex-89 | 7-fluoro-2-(2-(4-fluoroisoindolin-2-yl)ethyl)-[1,2,4]triazolo[1,5-c]quinazolin-5-amine | 467 [M + 1] |

Compound Ex-90, 2-(2-(3,4-dihydroisoquinolin-2(1H)-yl)ethyl)-7-methyl-[1,2,4]triazolo[1,5-c]quinazolin-5-amine

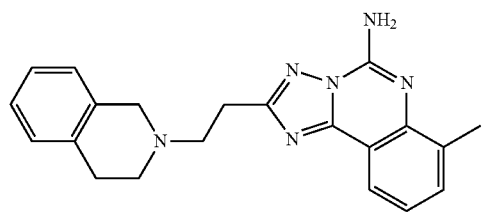

Ex-90 was prepared using the procedure of Example 6, Scheme 6, above, only substituting 2-amino-3-methylbenzoic acid for 2-amino-3-chlorobenzoic acid in step B and 1,2,3,4-tetrahydroisoquinoline for 5-fluoroisoindoline in step H. Compound Ex-90 was characterized by LC/MS: LCMS: m/z (M+1)=359.

Compound Ex-91, 8-fluoro-2-[2-(5-fluoro-1,3-dihydro-2H-isoindol-2-yl)ethyl][1,2,4]triazolo[1,5-c]quinazolin-5-amine

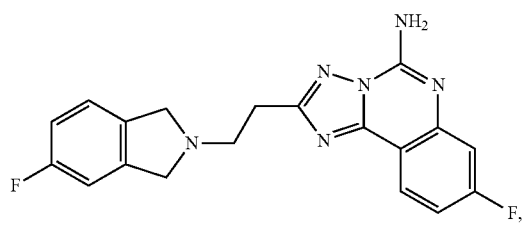

Ex-91 was prepared using the procedure of Example 6, Scheme 6, above, only substituting, substituting, substituting 2-amino-4-fluorobenzoic acid for 2-amino-3-chlorobenzoic acid in step B. Compound Ex-91 was characterized by LC/MS: m/z (M+1)=367.

Additional compounds prepared using this same procedure with appropriate reagent substitutions are presented in Table XII, below, along with the characteristic LC/MS data.

TABLE XII

| Compound No | Structure | LC-MS |
|---|---|---|
| Ex-92 | 2-(2-(5H-pyrrolo[3,4-b]pyridin-6(7H)-yl)ethyl)-8-fluoro-[1,2,4]triazolo[1,5-c]quinazolin-5-amine | 350 [M + 1] |
| Ex-93 | 2-(2-(3,4-dihydroisoquinolin-2(1H)-yl)ethyl)-8-fluoro-[1,2,4]triazolo[1,5-c]quinazolin-5-amine | 363 [M + 1] |
| Ex-94 | 2-(2-(3,4-dihydroquinolin-1(2H)-yl)ethyl)-8-fluoro-[1,2,4]triazolo[1,5-c]quinazolin-5-amine | 363 [M + 1] |
| Ex-95 | 2-(2-(3-ethyl-5,6-dihydro-[1,2,4]triazolo[4,3-a]pyrazin-7(8H)-yl)ethyl)-8-fluoro-[1,2,4]triazolo[1,5-c]quinazolin-5-amine | 382 [M + 1] |
| Ex-96 | 8-fluoro-2-(2-(4-fluoroisoindolin-2-yl)ethyl)-[1,2,4]triazolo[1,5-c]quinazolin-5-amine | 367 [M + 1] |

Compounds Ex-97 to Ex-100, presented along with characteristic LC/MS data in Table XIII, below, were prepared using the procedure detailed in Example 6, and in the preparation of compound Ex-83, above, by substituting the appropriate aminobenzoic acid for 2-amino-3-chlorobenzoic acid in step B thereof.

TABLE XIII

| Compound No. | Structure | LC-MS |
|---|---|---|
| Ex-97 | 2-(2-(5H-pyrrolo[3,4-b]pyridin-6(7H)-yl)ethyl)-7,8-dimethoxy-[1,2,4]triazolo[1,5-c]quinazolin-5-amine | 392 [M + 1] |
| Ex-98 | 2-(2-(5H-pyrrolo[3,4-b]pyridin-6(7H)-yl)ethyl)-9-fluoro-7-methoxy-[1,2,4]triazolo[1,5-c]quinazolin-5-amine | 380 [M + 1] |
| Ex-99 | 2-(2-(5H-pyrrolo[3,4-b]pyridin-6(7H)-yl)ethyl)-8,9-difluoro-[1,2,4]triazolo[1,5-c]quinazolin-5-amine | 368 [M + 1] |
| Ex-100 | 2-(2-(5H-pyrrolo[3,4-b]pyridin-6(7H)-yl)ethyl)-7,9-difluoro-[1,2,4]triazolo[1,5-c]quinazolin-5-amine | 368 [M + 1] |

Example 7: Preparation of racemic (±)-2-(3,3-difluoro-2-(5H-pyrrolo[3,4-b]pyridin-6(7H)-yl)propyl)-7-methoxy[1,2,4]triazolo[1,5-c]quinazolin-5-amine (Ex-100

SCHEME 8

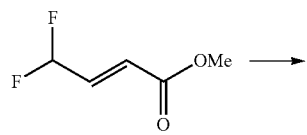

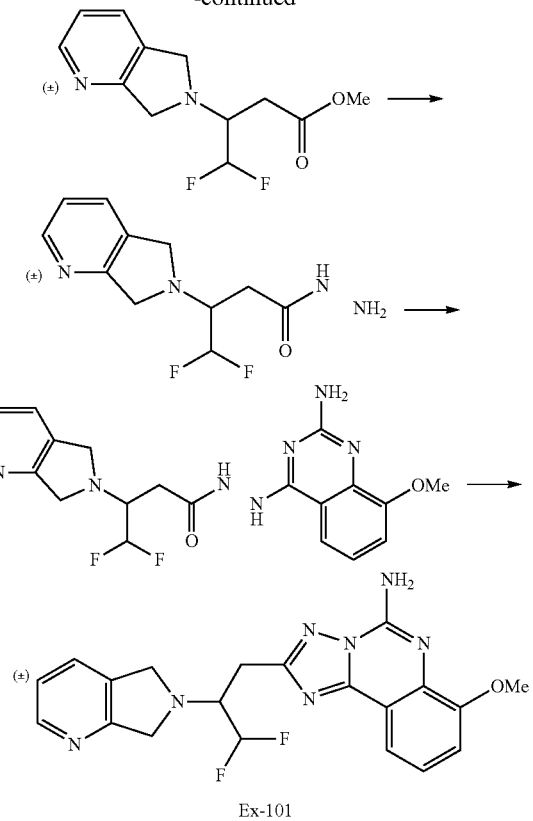

Ex-101

Step A: methyl 4,4-difluoro-3-(5H-pyrrolo[3,4-b]pyridin-6(7H)-yl)butanoate

To a solution of (E)-methyl 4,4-difluorobut-2-enoate (600 mg, 4.99 mmol) in acetonitrile (20 mL) was added 6,7-dihydro-5H-pyrrolo[3,4-b]pyridine (1.1 g, 7.49 mmol), followed by DBU (0.373 mL, 2.497 mmol). The reaction mixture was stirred at room temperature for 18 h and then concentrated in vacuo to afford the title compound.

Step B: (±)-4,4-difluoro-3-(5H-pyrrolo[3,4-b]pyridin-6(7H)-yl)butanehydrazide

To an ethanol (50 mL) solution of methyl 4,4-difluoro-3-(5H-pyrrolo[3,4-b]pyridin-6(7H)-yl)butanoate (step A, 1.35 g, 4.99 mmol) was added hydrazine hydrate (2.423 mL, 49.9 mmol). The reaction mixture was stirred in a sealed tube at 80° C. for 4 h and concentrated in vacuo. The crude product was purified by flash chromatography ($CH_2Cl_2$:MeOH 10:1 to $CH_2Cl_2$:MeOH 5:1) to yield the title compound which was characterized by LC/MS. LC/MS=257 [M+1].

Step C: (±)-N'-(2-amino-8-methoxyquinazolin-4-yl)-4,4-difluoro-3-(5H-pyrrolo[3,4-b]pyridin-6(7H)-yl)butanehydrazide To a THF (50 mL) suspension of N-(8-methoxy-4-(1H-1,2,4-triazol-1-yl)quinazolin-2-yl)acetamide (600 mg 2.111 mmol) was added (±)-4,4-difluoro-3-(5H-pyrrolo[3,4-b]pyridin-6(7H)-yl)butanehydrazide prepared in step B (595 mg, 2.322 mmol) and DIPEA (0.441 mL, 2.53 mmol). The reaction mixture was stirred at 60° C. for 3 hours, and then concentrated in vacuo. To a MeOH (50 mL) and water (50 mL) suspension of the residue was added potassium carbonate (2.2 g, 15.9 mmol). The mixture was stirred in a sealed tube at 80° C. until all the starting material was consumed. The reaction mixture was concentrated in vacuo and diluted with dichloromethane and methanol. The resulting precipitate was filtered off, and the filtrate was then concentrated in vacuo. The resulting residue was purified by flash chromatography (dichloromethane:methanol 10:1) to yield the title compound which was characterized by LC/MS, LC/MS=430 [M+1].

Step D: (±)-2-(3,3-difluoro-2-(5H-pyrrolo[3,4b]-pyridin-6(7H)-yl)propyl)-7-methoxy-[1,2,4]triazolo[1,5-c]quinazolin-5-amine To (±)-N"-(2-amino-8-methoxyquinazolin-4-yl)-4,4-difluoro-3-(5H-pyrrolo[3,4-b]pyridin-6(7H)-yl)butanehydrazide (step C, 1.1 g, 2.56 mmol) was added BSTA (6.35 mL, 25.6 mmol). The suspension was stirred at 120° C. for 2 hr. The reaction mixture was concentrated in vacuo with heating. The residue was purified by flash chromatography (dichloromethane:methanol 20:1) to afford compound Ex-101 which was characterized using, LC/MS=412 [M±1].

Using the procedure of Example 7 and Scheme 7, the compounds reported in Table XIV were prepared in the racemic form. The enantiomeric forms were separated through chiral HPLC.

TABLE XIV

| Compound No. | Structure | LC-MS |
|---|---|---|
| Ex-102 | (S)-2-(3,3-difluoro-2-(5H-pyrrolo[3,4-b]pyridin-6(7H)-yl)propyl)-7-methoxy-[1,2,4]triazolo[1,5-c]quinazolin-5-amine | 412 [M + 1] |
| Ex-103 | (R)-2-(3,3-difluoro-2-(5H-pyrrolo[3,4-b]pyridin-6(7H)-yl)propyl)-7-methoxy-[1,2,4]triazolo[1,5-c]quinazolin-5-amine | 412 [M + 1] |
| Ex-104 | 2-(3-fluoro-2-(5H-pyrrolo[3,4-b]pyridin-6(7H)-yl)propyl)-7-methoxy-[1,2,4]triazolo[1,5-c]quinazolin-5-amine | 394 [M + 1] |
| Ex-105 | 2-(2-(5H-pyrrolo[3,4-b]pyridin-6(7H)-yl)propyl)-7-methoxy-[1,2,4]triazolo[1,5-c]quinazolin-5-amine | 376 [M + 1] |
| Ex-106 | (S)-2-(2-(5H-pyrrolo[3,4-b]pyridin-6(7H)-yl)propyl)-7-methoxy-[1,2,4]triazolo[1,5-c]quinazolin-5-amine | 376 [M + 1] |
| Ex-107 | (R)-2-(2-(5H-pyrrolo[3,4-b]pyridin-6(7H)-yl)propyl)-7-methoxy-[1,2,4]triazolo[1,5-c]quinazolin-5-amine | 376 [M + 1] |
| Ex-108 | 7-methoxy-2-(3,3,3-trifluoro-2-(5H-pyrrolo[3,4-b]pyridin-6(7H)-yl)propyl)-[1,2,4]triazolo[1,5-c]quinazolin-5-amine | 430 [M + 1] |
| Ex-109 | (S)-7-methoxy-2-(3,3,3-trifluoro-2-(5H-pyrrolo[3,4-b]pyridin-6(7H)-yl)propyl)-[1,2,4]triazolo[1,5-c]quinazolin-5-amine | 430 [M + 1] |
| Ex-110 | (R)-7-methoxy-2-(3,3,3-trifluoro-2-(5H-pyrrolo[3,4-b]pyridin-6(7H)-yl)propyl)-[1,2,4]triazolo[1,5-c]quinazolin-5-amine | 430 [M + 1] |

TABLE XIV-continued

| Compound No. | Structure | LC-MS |
|---|---|---|
| Ex-111 | 2-(2-(5H-pyrrolo[3,4-b]pyridin-6(7H)-yl)butyl)-7-methoxy-[1,2,4]triazolo[1,5-c]quinazolin-5-amine | 390 [M + 1] |
| Ex-112 | (R)-2-(2-(5H-pyrrolo[3,4-b]pyridin-6(7H)-yl)butyl)-7-methoxy-[1,2,4]triazolo[1,5-c]quinazolin-5-amine | 390 [M + 1] |
| Ex-113 | (S)-2-(2-(5H-pyrrolo[3,4-b]pyridin-6(7H)-yl)butyl)-7-methoxy-[1,2,4]triazolo[1,5-c]quinazolin-5-amine | 390 [M + 1] |
| Ex-114 | 2-(2-(5-fluoroisoindolin-2-yl)propyl)-7-methoxy-[1,2,4]triazolo[1,5-c]quinazolin-5-amine | 393 [M + 1] |
| Ex-115 | 2-(2-(5H-pyrrolo[3,4-b]pyridin-6(7H)-yl)pentyl)-7-methoxy-[1,2,4]triazolo[1,5-c]quinazolin-5-amine | 404 [M + 1] |
| Ex-116 | 7-methoxy-2-(2-(2-methyl-6,7-dihydrooxazolo[5,4-c]pyridin-5(4H)-yl)propyl)-[1,2,4]triazolo[1,5-c]quinazolin-5-amine | 394 [M + 1] |

Example 8: Preparation of 2-((5-fluoroisoindolin-2-yl)methyl)-7-methoxy-[1,2,4]triazolo[1,5-c]quinazolin-5-amine (Ex-117)

SCHEME 8

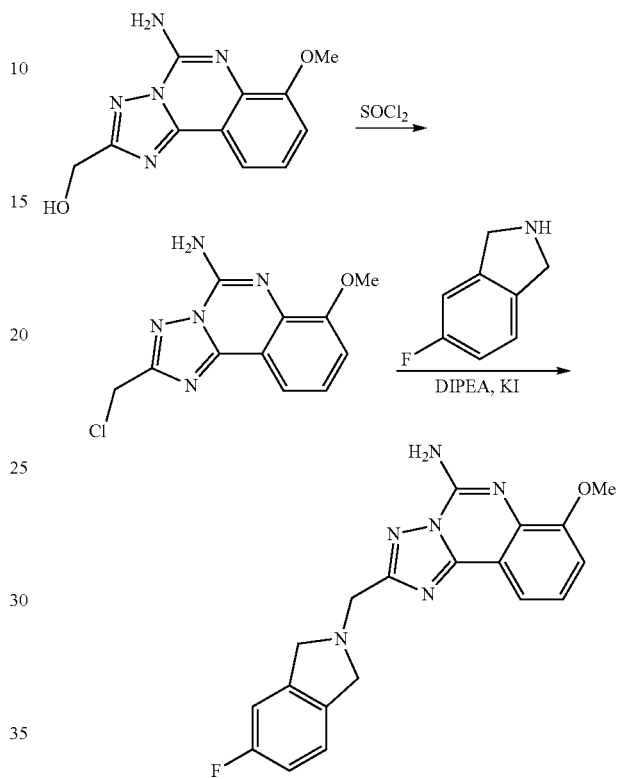

Ex-117

Step A: Preparation of 2-(chloromethyl)-7-methoxy-[1,2,4]triazolo[1,5-c]-quinazolin-5-amine (5-amino-7-methoxy-[1,2,4]triazolo[1,5-c]quinazolin-2-yl)methanol (4 g, 15.4 mmol, prepared in accordance with Example 10) was suspended in DCM (50 mL) and SOCl$_2$ (50 ml). The mixture was stirred at RT for 1 h, concentrated in vacuo to remove SOCl$_2$ completely. The residue was suspended in DCM/Hex (1:2), cooled to 0° C., filtered and dried to afford the titled compound. LC/MS=264 [M+1].

Step B: 2-((5-fluoroisoindolin-2-yl)methyl)-7-methoxy-[1,2,4]triazolo[1,5-c]-quinazolin-5-amine The "right-side" precursor 2-(chloromethyl)-7-methoxy-[1,2,4]triazolo[1,5-c]quinazolin-5-amine (150 mg, 0.54 mmol), and "left-side" precursor 5-fluoroisoindoline (92 mg, 1.1 mmol) were placed in a reaction vessel with DIPEA (105 mg, 0.81 mmol) and KI (269 mg, 1.62 mmol) in DMF (50 mL) and the mixture was stirred at 80° C. for 18 h. The mixture was cooled to RT, diluted with DCM, washed with H$_2$O (3×), dried and concentrated. Chromatography purification MeOH/DCM (1:30-1:20-1:10) afforded the compound Ex-117, which was characterized using LC/MS=365 [M+1].

The process of Scheme 8 was repeated with an appropriate "left-side" precursor to provide the compounds of Table XV.

TABLE XV

| Compound No. | Structure | LC-MS |
|---|---|---|
| Ex-118 | 2-((5H-pyrrolo[3,4-b]pyridin-6(7H)-yl)methyl)-7-methoxy-[1,2,4]triazolo[1,5-c]quinazolin-5-amine | 348 [M + 1]. |
| Ex-119 | 2-((3,4-dihydroquinolin-1(2H)-yl)methyl)-7-methoxy-[1,2,4]triazolo[1,5-c]quinazolin-5-amine | 361 [M + 1]. |
| Ex-120 | 2-((2H-benzo[b][1,4]oxazin-4(3H)-yl)methyl)-7-methoxy-[1,2,4]triazolo[1,5-c]quinazolin-5-amine | 363 [M + 1]. |
| Ex-121 | 2-((3,4-dihydroisoquinolin-2(1H)-yl)methyl)-7-methoxy-[1,2,4]triazolo[1,5-c]quinazolin-5-amine | 361 [M + 1]. |

TABLE XV-continued

| Compound No. | Structure | LC-MS |
|---|---|---|
| Ex-122 | 2-((5-amino-7-methoxy-[1,2,4]triazolo[1,5-c]quinazolin-2-yl)methyl)-1,2,3,4-tetrahydroisoquinoline-6-carbonitrile | 386 [M + 1]. |
| Ex-123 | 2-((5,6-dihydro-1,7-naphthyridin-7(8H)-yl)methyl)-7-methoxy-[1,2,4]triazolo[1,5-c]quinazolin-5-amine | 362 [M + 1]. |
| Ex-124 | 7-methoxy-2-((7-methoxy-4,5-dihydro-1H-benzo[d]azepin-3(2H)-yl)methyl)-[1,2,4]triazolo[1,5-c]quinazolin-5-amine | 405 [M + 1]. |
| Ex-125 | 2-((3,4-dihydro-2,7-naphthyridin-2(1H)-yl)methyl)-7-methoxy-[1,2,4]triazolo[1,5-c]quinazolin-5-amine | 362 [M + 1]. |

TABLE XV-continued

| Compound No. | Structure | LC-MS |
|---|---|---|
| Ex-126 | 7-methoxy-2-((8-((4-(pyridin-2-yl)piperazin-1-yl)methyl)-3,4-dihydroisoquinolin-2(1H)-yl)methyl)-[1,2,4]triazolo[1,5-c]quinazolin-5-amine | 537 [M + 1]. |
| Ex-127 | 7-methoxy-2-((2,3,4,5-(trifluoromethyl)isoindolin-2-yl)methyl)-[1,2,4]triazolo[1,5-c]quinazolin-5-amine | 415 [M + 1]. |
| Ex-128 | 7-methoxy-2-((2,3,4,5-tetrahydro-1H-benzo[b]azepin-1-yl)methyl)-[1,2,4]biazolo[1,5-c]quinazolin-5-amine | 375 [M + 1]. |
| Ex-129 | 7-methoxy-2-((3-(trifluoromethyl)-7,8-dihydro-1,6-naphthyridin-6(5H)-yl)methyl)-[1,2,4]tria.zolo[1,5-c]quinazolin-5-amine | 430 [M + 1]. |

TABLE XV-continued

| Compound No. | Structure | LC-MS |
|---|---|---|
| Ex-130 | 2-((6-fluoro-3,4-dihydroisoquinolin-2(1H)-yl)methyl)-7-methoxy-[1,2,4]triazolo[1,5-c]quinazolin-5-amine | 379 [M + 1]. |
| Ex-131 | 2-((4,5-dihydro-1H-benzo[d]azepin-3(2H)-yl)methyl)-7-methoxy-[1,2,4]triazolo[1,5-c]quinazolin-5-amine | 375 [M + 1]. |
| Ex-132 | 2-((4,5-dihydro-1H-benzo[c]azepin-2(3H)-yl)methyl)-7-methoxy-[1,2,4]triazolo[1,5-c]quinazolin-5-amine | 375 [M + 1]. |
| Ex-133 | 2-((3,4-dihydro-1,5-naphthyridin-1(2H)-yl)methyl)-7-methoxy-[1,2,4]triazolo[1,5-c]quinazolin-5-amine | 362 [M + 1]. |

TABLE XV-continued

| Compound No. | Structure | LC-MS |
|---|---|---|
| Ex-134 | 2-((3,4-dihydro-1,6-naphthyridin-1(2H)-yl)methyl)-7-methoxy-[1,2,4]triazolo[1,5-c]quinazolin-5-amine | 362 [M + 1]. |
| Ex-135 | 2-((3,4-dihydro-1,7-naphthyridin-1(2H)-yl)methyl)-7-methoxy-[1,2,4]triazolo[1,5-c]quinazolin-5-amine | 362 [M + 1]. |
| Ex-136 | 2-((7-chloro-4-methyl-2,3,4,5-tetrahydro-1H-benzo[e][1,4]diazepin-1-yl)methyl)-7-methoxy-[1,2,4]triazolo[1,5-c]quinazolin-5-amine | 425 [M + 1]. |
| Ex-137 | 2-((2-chloro-5H-pyrrolo[3,4-b]pyridin-6(7H)-yl)methyl-7-methoxy-[1,2,4]triazolo[1,5-c]quinazolin-5-amine | 382 [M + 1] |

TABLE XV-continued

| Compound No. | Structure | LC-MS |
|---|---|---|
| Ex-138 | 7-methoxy-2-((3-(methylthio)-5,6-dihydro-[1,2,4]triazolo[4,3-a]pyrazin-7(8H)-)4)methyl)[1,2,4]triazolo[1,5-c]quinazolin-5-amine | 398 [M + 1]. |
| Ex-139 | ethyl 7-((5-amino-7-methoxy-[1,2,4]triazolo[1,5-c]quinazolin-2-yl)methyl)-5,6,7,8-tetrahydro-[1,2,4]triazolo[4,3-a]pyrazine-3-carboxylate | 424 [M + 1]. |
| Ex-140 | 2-((3-bromo-5,6-dihydro-[1,2,4]triazolo[4,3-a]pyrazin-7(8H)-yl)methyl)-7-methoxy-[1,2,4]triazolo[1,5-c]quinazolin-5-amine | 431 [M + 1]. |
| Ex-141 | 2-((5-dihydro-[1,2,4]triazolo[4,3-a]pyrazin-7(8H)-yl)methyl)-7-methoxy-[1,2,4]triazolo[1,5-c]quinazolin-5-amine | 352 [M + 1]. |

TABLE XV-continued

| Compound No. | Structure | LC-MS |
|---|---|---|
| Ex-142 | 2-((3-ethyl-5,6-dihydro-[1,2,4]triazolo[4,3-a]pyrazin-7(8H)-yl)methyl)-7-methoxy-[1,2,4]triazolo[1,5-c]quinazolin-5-amine | 380 [M + 1]. |
| Ex-143 | 7-((5-amino-7-methoxy-[1,2,4]triazolo[1,5-c]quinazolin-2-yl)methyl)-N-tert-butyl-5,6,7,8-tetrahydro-[1,2,4]triazolo[4,3-a]pyrazine-3-carboxamide | 451 [M + 1]. |
| Ex-144 | 7-methoxy-2-((3-methoxy-5,6-dihydro[1,2,4]triazolo[4,3-a]pyrazin-7(8H)-yl)methyl)[1,2,4]triazolo[1,5-c]quinazolin-5-amine | 382 [M + 1]. |
| Ex-145 | 2-((5,5-dimethyl-3-(trifluoromethyl)-5,6-dihydro-[1,2,4]triazolo[4,3-a]pyrazin-7(8H)-yl)methyl)-7-methoxy-[1,2,4]triazolo[1,5-c]quinazolin-5-amine | 448 [M + 1]. |

TABLE XV-continued
| Compound No. | Structure | LC-MS |
|---|---|---|
| Ex-146 | 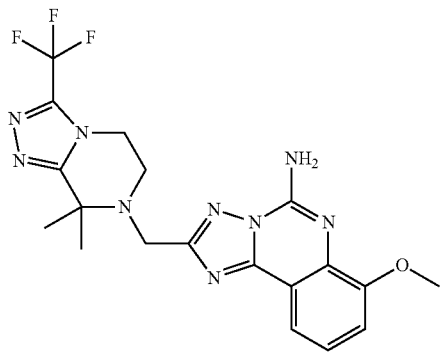 [SMILES: COc1cccc2c1nc(N)n1nc(CN3CCn4c(C(F)(F)F)nnc4C3(C)C)nc21]<br>2-((8,8-dimethyl-3-(trifluoromethyl)-5,6-dihydro-[1,2,4]triazolo[4,3-a]pyrazin-7(8H)-yl)methyl)-7-methoxy-[1,2,4]triazolo[1,5-c]quinazolin-5-amine | 448 [M + 1]. |
| Ex-148 | 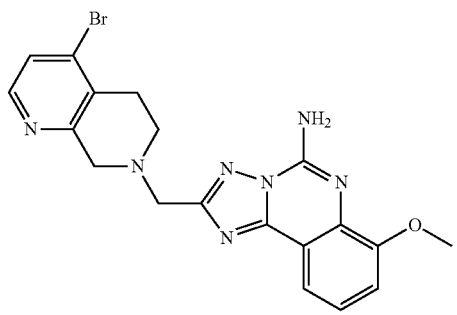 [SMILES: COc1cccc2c1nc(N)n1nc(CN3CCc4c(Br)ccnc4C3)nc21]<br>2((4-bromo-5,6-dihydro-1,7-naplithyridin-7(8H)-yl)methyl-7-methoxy-[1,2,4]triazolo[1,5-c]quinazol in-5-amine | 441 [M + 1] |
| Ex-149 | 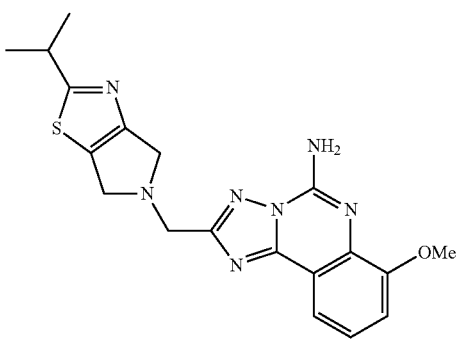 [SMILES: COc1cccc2c1nc(N)n1nc(CN3Cc4nc(C(C)C)sc4C3)nc21]<br>2-((2-isopropyl-4H-pyrrolo[3,4-d]thiazol-5(6H)-yl)methyl)-7-methoxy-[1,2,4]triazolo[1,5-c]quinazolin-5-amine | 396 [M + 1] |

TABLE XV-continued

| Compound No. | Structure | LC-MS |
|---|---|---|
| Ex-150 | 2-((7,8-dihydropyrido[4,3-b]pyrazin-6(5H)-yl)methyl)-7-methoxy-[1,2,4]triazolo[1,5-c]quinazolin-5-amine | 363 [M + 1]. |
| Ex-151 | 2-((5,6-dihydropyrido[3,4-d]pyrimidin-7(8H)-yl)methyl)-7-methoxy-[1,2,4]triazolo[1,5-c]quinazolin-5-amine | 363 [M + 1]. |
| Ex-152 | 7-methoxy-2-((2-(trifluoromethyl)-5H-pyrrolo[3,4-d]pyrimidin-6(7H)-yl)methyl)-[1,2,4]triazolo[1,5-c]quinazolin-5-amine | 417 [M + 1]. |
| Ex-153 | 7-methoxy-2-((3-(trifluoromethyl)-5,6-dihydro[1,2,4]triazolo[4,3-a]pyrazin-7(8H)-yl)methyl)-[1,2,4]triazolo[1,5-c]quinazolin-5-amine | 420 [M + 1] |

TABLE XV-continued

| Compound No. | Structure | LC-MS |
|---|---|---|
| Ex-154 | 2-((2,3-dihydro-1H-pyrrolo[2,3-b]pyridin-1-yl)methyl)-7-methoxy-[1,2,4]triazolo[1,5-c]quinazolin-5-amine | 348 [M + 1] |
| Ex-155 | 2-((5-bromo-2,3-dihydro-1H-pyrrolo[2,3-b]pyridin-1-yl)methyl)-7-methoxy-[1,2,4]triazolo[1,5-c]quinazolin-5-amine | 428 [M + 1] |
| Ex-156 | 7-methoxy-2((7-methyl-3,4-dihydro-1,8-naphthyridin-1(2H)-yl)methyl)-[1,2,4]triazolo[1,5-c]quinazolin-5-amine | 376 [M + 1] |
| Ex-157 | 2-((7,8-dihydro-5H-pyrido[2,3-b]azepin-9(6H)-yl)methyl)-7-methoxy-[1,2,4]triazolo[1,5-c]quinazolin-5-amine | 376 [M + 1] |
| Ex-158 | 2((2,3-dihydro-1H-pyrrolo[2,3-b]pyridin-1-yl)methyl-7-methoxy-[1,2,4]triazolo[1,5-c]quinazolin-5-amine | 348 [M + 1] |

TABLE XV-continued

| Compound No. | Structure | LC-MS |
|---|---|---|
| Ex-160 | 2-((2-chloro-7,8-dihydro-5H-pyrido[2,3-b]azepin-9(6H)-yl)methyl)-7-methoxy-[1,2,4]triazolo[1,5-c]quinazolin-5-amine | 410 [M + 1] |
| Ex-161 | 2-((3,4-dihydro-1,8-naphthyridin-1(2H)-yl)methyl)-7-methoxy-[1,2,4]triazolo[1,5-c]quinazolin-5-amine | 362 [M + 1] |
| Ex-162 | 7-methoxy-2-((2-(pyridin-2-yl)-7,8-dihydro-5H-pyrido[2,3-b]azepin-9(6H)-yl)methyl)-[1,2,4]triazolo[1,5-c]quinazolin-5-amine | 453 [M + 1] |
| Ex-163 | 2-((4,4-dimethyl-3,4-dihydroisoquinolin-2(1H)-yl)methyl)-7-methoxy-[1,2,4]triazolo[1,5-c]quinazolin-5-amine | 389 [M + 1] |

TABLE XV-continued

| Compound No. | Structure | LC-MS |
|---|---|---|
| Ex-164 | 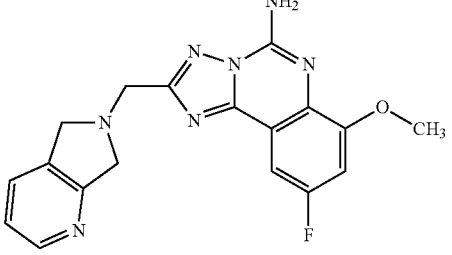 2-((5H-pyrrolo[3,4-b]pyridin-6(7H)-yl)methyl)-9-fluoro-7-methoxy-[1,2,4]triazolo[1,5-c]quinazolin-5-amine | 366 [M + 1] |
| Ex-165 | 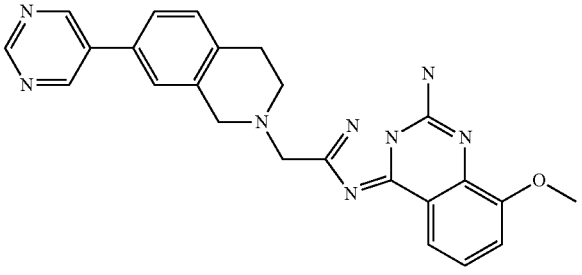 [SMILES: COc1cccc2/c(=N/C(=N)CN3CCc4ccc(-c5cncnc5)cc4C3)[nH]c(N)nc12] 7-methoxy-2-((7-(pyrimidin-5-yl)-3,4-dihydroisoquinolin-2(1H)-yl)methyl)-[1,2,4]triazolo[1,5-c]quinazolin-5-amine | 439 [M + 1] |
| Ex-166 | 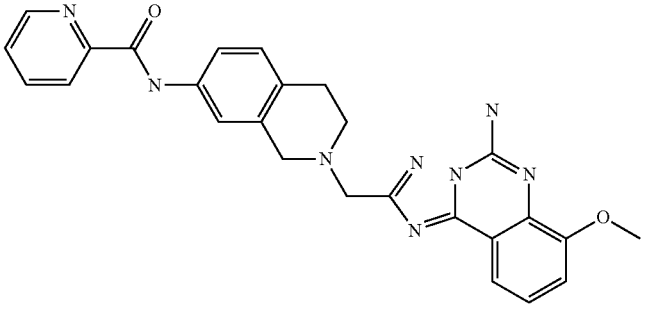 [SMILES: COc1cccc2/c(=N/C(=N)CN3CCc4ccc(NC(=O)c5ccccn5)cc4C3)[nH]c(N)nc12] N-(2-((5-amino-7-methoxy-[1,2,4]triazolo[1,5-c]quinazolin-2-yl)methyl)-1,2,3,4-tetrahydroisoquinolin-7-yl)picolinamide | 481 [M + 1] |
| Ex-167 | 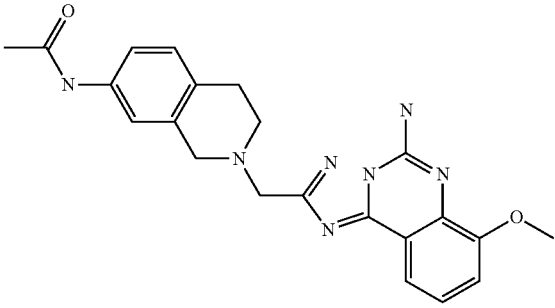 [SMILES: COc1cccc2/c(=N/C(=N)CN3CCc4ccc(NC(C)=O)cc4C3)[nH]c(N)nc12] N-(2-((5-amino-7-methoxy-[1,2,4]triazolo[1,5-c]quinazolin-2-yl)methyl)-1,2,3,4-tetrahydroisoquinolin-7-yl acetamide | 418 [M + 1] |

TABLE XV-continued

| Compound No. | Structure | LC-MS |
|---|---|---|
| Ex-168 | 2-((7-(3,4-difluorophenyl)-3,4-dihydroisoquinolin-2(1H-yl)methyl)-7-methoxy-[1,2,4]triazolo[1,5-c]quinazolin-5-amine | 473 [M + 1] |
| Ex-173 | 2-(2-((5-amino-7-methoxy-[1,2,4]triazolo[1,5-c]quinazolin-2-yl)methyl)-1,2,3,4-tetrahydroisoquinolin-7-yl)-N-(pyridine-3-yt )acetamide | 495 [M + 1] |
| Ex-175 | 7-methoxy-24(5-(pyrimidin-5-yl)isoindolin-2-yl)methyl)-[1,2,4]triazolo[1,5-c]quinazolin-5-amine | 425 [M + 1] |
| Ex-177 | 7-methoxy-2-((8-(pyrimidin-5-yl)-3,4-dihydroisoquinolin-2(1H)-yl)methyl)-[1,2,4]triazolo[l,5-c]quinazolin-5-amine | 439 [M + 1] |

TABLE XV-continued

| Compound No. | Structure | LC-MS |
|---|---|---|
| Ex-179 | 7-methoxy-2-((7-(2-(trifluoromethyl)pydmidin-5-yl)-3,4-dihydroisoquinolin-2(1H)-yl)methyl)-[1,2,4]triazolo[1,5-c]quinazolin-5-amine | 507 [M + 1] |
| Ex-180 | 7-methoxy-2-47-(1-methyl-1H-pyrazol-4-yl)-3,4-dihydroisoquinolin-2(1H)-yl)methyl)-[1,2,4]triazolo[1,5-c]quinazolin-5-amine | 441 [M + 1] |
| Ex-182 | 7-methoxy-2-((7-(1-methyl-5-(trifluoromethyl)-1H-pyrazol-4-yl)-3,4-dihydroisoquinolin-2(1H)-yl)methyl)-[1,2,4]triazolo[1,5-c]quinazolin-5-amine | 509 [M + 1] |
| Ex-184 | 7-methoxy-2-((7-(1-methyl-3-(trifluoromethyl)-1H-pyrazol-4-yl)-3,4-dihydroisoquinolin-2(1H)-yl)methyl)-[1,2,4]triazolo[1,5-c]quinazolin-5-amine | 509 [M + 1] |

TABLE XV-continued

| Compound No. | Structure | LC-MS |
|---|---|---|
| Ex-185 | 7-methoxy-2-((7-(2-(trifluoromethyl)phenyl)-3,4-dihydroisoquinolin-2(1H)-yl)methyl)-[1,2,4]triazolo[1,5-c]quinazolin-5-amine | 505 [M + 1] |
| Ex-186 | 2-((7-(2-amino-4-(trifluoromethyl)pyrimidin-5-yl)-3,4-dihydroisoquinolin-2(1H)-yl)methyl)-7-methoxy-[1,2,4]triazolo[1,5-c]-quinazolin-5-amine | 522 [M + 1] |
| Ex-187 | 7-methoxy-2-(2-(7-(2-(trifluoromethyl)pyrimidin-5-yl)-3,4-dihydroisoquinolin-2(1H)-yl)ethyl)-[1,2,4]triazolo[1,5-c]quinazolin-5-amine | 521 [M + 1] |

Example 9: Preparation of 7-Bromo-2-((5,6-di-hydro-1,7-naphthyridin-7(8H)yl)methyl))-[1,2,4]-triazolo[1,5-c]quinazolin-5-amine (Ex-194)

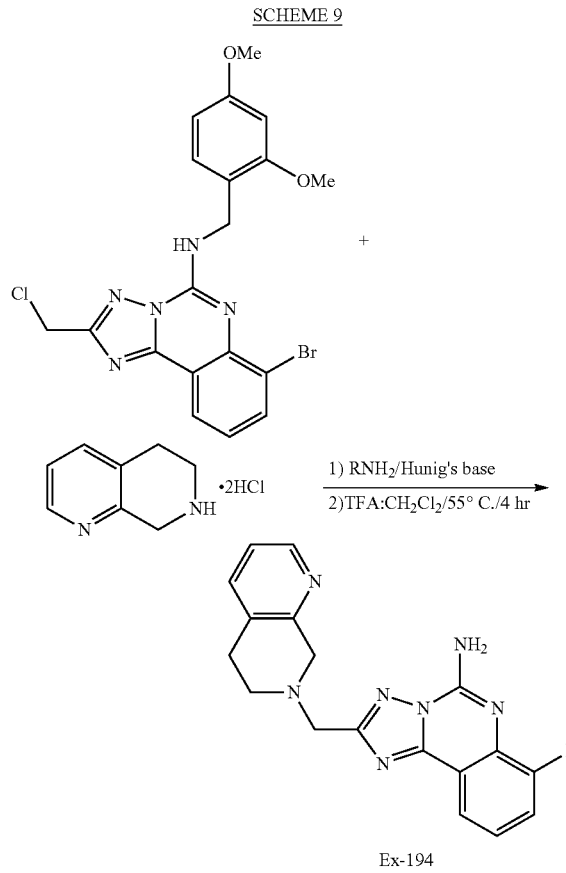

Ex-194

Diisopropylethyl amine (17 mg; 0.13 mmol) was added to an amber colored solution of 7-bromo-2-(chloromethyl)-N-(2,4-dimethoxybenzyl)-[1,2,4]triazolo[1,5-c]quinazolin-5-amine (20 mg; 0.043 mmol, prepared in accordance with Scheme 1, above, using 2-amino-3-bromo-benzoic acid in lieu of 2 amino-3-methoxy benzoic acid) and 5,6,7,8-tetra-hydro-[1,7]-naphthyridine (20 mg; 0.095 mmol) in dry DMF (1 mL) and the reaction mixture was stirred for 20 hr at room temperature. After verifying the absence of the tricyclic chloride by MS, the reaction mixture was diluted with EtOAc and washed with water, saturated NH$_4$Cl solution and brine. Concentration and purification by preparative TLC (5% CH$_3$OH in CH$_2$Cl$_2$) served to isolate compound Ex-194-DMB (DMB-protected analog of compound Ex-194) as a white solid which was characterized using LC-MS: 560 (M$^+$); R$_f$=2.52.

The DMB protected product from step-1 was dissolved in CH$_2$Cl$_2$-TFA (0.5 mL each), stirred and heated at 55° C. for 4 hr. After verifying absence of SM and presence of product (MH=410/412)), CH$_2$Cl$_2$ and TFA were removed on the rotovap. Toluene (2×5 mL) was added and removed in vacuo followed by 7% NH3 in CH3OH which was also removed in vacuo. The resulting residue was applied to a prep plate and developed with 7% NH$_3$-methanol-CH$_2$Cl$_2$ (5:95). The uv-active band of medium polarity was isolated and the product extracted with the same solvent system. Concentration of the extract in vacuo gave compound Ex-194 as white solid.

The process of Scheme 9 was repeated with an appropriate "left-side" precursor to provide the compound of Table XVI.

TABLE XVI

| Compound No. | Structure | M + 1 (R$_t$) |
|---|---|---|
| Ex-195 | 2-((5H-pyrrolo[3,4-b]pyridin-6(7H)-yl)methyl)-7-bromo-[1,2,4]triazolo[1,5-c]quinazolin-5-amine | 396 (1.81) |

Example 10: Preparation of "Right-Side" Precursors Having Various Substituents at 7-C from (7-bromo-5-(2,4-dimethoxybenzylamino)-[1,2,4]triazolo[1,5-c]quinazolin-2-yl)methanol and preparation of compounds of the invention therefrom The "right-side" precursor 2-Chloromethyl-5-(2,4-dimethoxybenzyl amino)-7-cyano-[1,2,4]-triazolo[1,5-c]quinazoline (Intermediate-12) was prepared in accordance with Scheme 10:

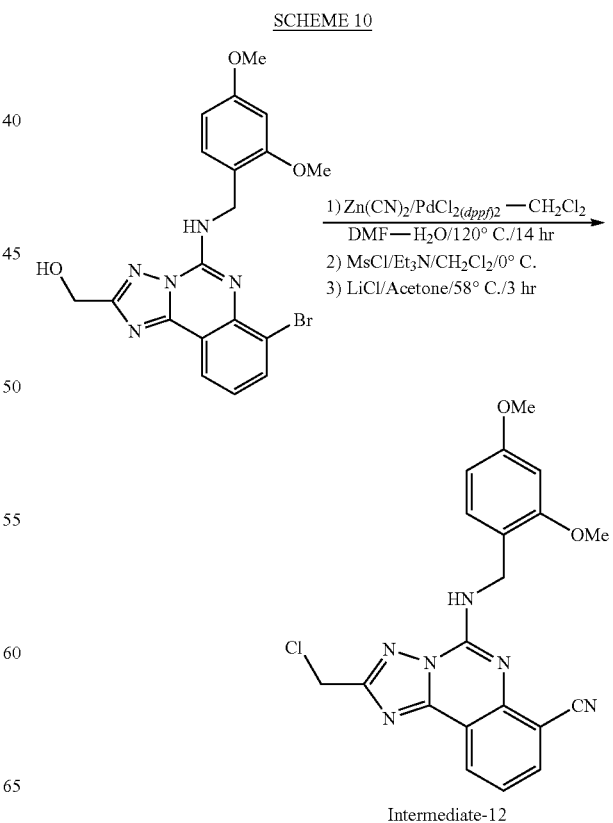

Intermediate-12

Step-1: A mixture of 7-Bromo-5-(2,4-dimethoxybenzyl amino)-2-hydroxymethyl-[1,2,4]-triazolo[1,5-c]quinazoline (200 mg; 0.45 mmol, prepared in accordance with Schemes 1 and 7, above, using 2-amino-3-bromo-benzoic acid starting material in lieu of 2 amino-3-methoxy benzoic acid), zinc cyanide (31.7 mg; 0.27 mmol) and $PdCl_2(dppf)_2$:$CH_2Cl_2$ were dissolved in DMF (1 mL) and water (0.1 mL,). The resulting clear red solution was degassed with nitrogen, stirred and heated at 120° C. for 14 hr. MS analysis of the reaction mixture showed absence of the starting bromo tricyclic alcohol and presence of the product nitrile ($MH^+$ =391). The reaction mixture was quenched with water and organics were extracted with EtOAc. The organic extract was further washed with water, brine and dried over solid anhydrous $Na_2SO_4$. The crude product was purified by preparative TLC, developing the plate with $EtOAc/CH_2Cl_2$ (1:1). The 7-cyano tricyclic alcohol was isolated as beige solid.

Step-2: A solution of compound (140 mg; 0.36 mmol) in $CH_2Cl_2$ (2 mL) and $CDCl_3$ (2 mL) was cooled in an ice bath and treated sequentially with $Et_3N$ (40 mg; 55 uL; 0.395 mmol) and MsCl (49 mg; 0.43 mmol), taking care not to use even a slight excess of $Et_3N$ to avoid quaternary salt formation. The ice bath was removed after 5 minutes and the reaction mixture was stirred at RT for 45 minutes when the analysis (TLC, MS) showed absence of alcohol. The reaction mixture was diluted with EtOAc and washed with water, brine, dried and concentrated to obtain the crude mesylate.

Step-3: The crude mesylate was redissolved in acetone (3 mL), treated with solid LiCl (76 mg; 1.79 mmol) and was stirred with heating at 58° C. for 3 hr. After confirming the complete formation of the tricyclic chloride ($MH^+$=408/410), the reaction mixture was cooled to RT and acetone was removed under house vacuum. The residue was dissolved in $CH_2Cl_2$:$CHCl_3$ (4:1) and washed with water, brine and concentrated to obtain 140 mg of a beige solid. The crude product thus obtained was purified by preparative TLC (30% EtOAc—$CH_2Cl_2$) to furnish Intermediate-12 as off-white solid.

Intermediate-12, prepared above, was used to prepare compounds of the invention in accordance with Scheme 10a:

SCHEME 10a

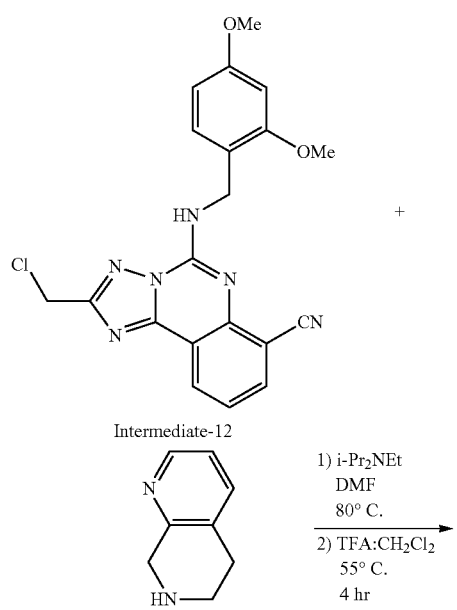

1) i-$Pr_2NEt$
DMF
80° C.
2) TFA:$CH_2Cl_2$
55° C.
4 hr

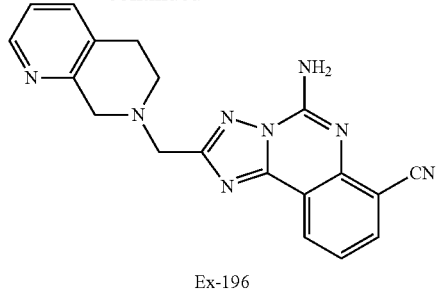

Ex-196

Step-1: A clear amber solution of 7-cyano tricyclic chloride 12 previously prepared (110 mg, 0.27 mmol), 5,6,7,8-tetrahydro-1,7-naphthyridine (85 mg; 0.37 mmol) and Hunig's base (0.14 mL; 104 mg; 0.807 mmol) in anhydrous DMF (1 mL) was stirred and heated at 80° C. for 18 hr. The reaction mixture was cooled to RT, diluted with water and extracted with EtOAc. The organic extract was washed with water and brine. Combined aqueous layers were back extracted with $CH_2Cl_2$. Both organic extracts were combined, dried over solid anhydrous $Na_2SO_4$ and concentrated to get 140 mg of beige solid. The crude product was purified by preparative TLC (5% $CH_3OH$—$CH_2Cl_2$) and the major fluorescent band, which was the 2,4-dimethoxybenzyl protected form of compound Ex-196, was isolated as an off-white solid, MS=507 ($MH^+$).

Step-2: The DMB-protected form of compound Ex-196, prepared above, was dissolved in $CH_2Cl_2$:TFA (1 mL each) and stirred at 57° C. for 4 hr. The clear reaction mixture had become deep purple and MS showed complete deprotection of the DMB group to give the compound. Ex-196, 5-amino-2-((5,6-dihydro-1,7-naphthyridin-7(8H)-yl)methyl)[1,2,4]triazolo[1,5-c]quinazoline-7-carbonitrile. The solvents were removed on a rotary evaporator and the residual TFA was removed by azeotrope formation with toluene to give a yellow sticky semi-solid. This material was treated with 7% $NH_3$ in methanol, stirred for 10 minutes and concentrated to obtain a beige solid. The crude product was purified by preparative TLC ($CH_2Cl_2$ with 7% $NH_3$ in methanol, 96:4) to afford compound Ex-196 as an off-white solid (77 mg; 87%). LC-MS: 357 ($MH^+$); $R_t$=2.02.

As shown in Table XVII, compound Ex-197 was prepared using this same procedure.

TABLE XVII

| Compound No. | Structure | M + 1 ($R_t$) |
| --- | --- | --- |
| Ex-197 | 2-((5H-pyrrolo[3,4-b]pyridin-6(7H)-yl)methyl)-5-amino-[1,2,4]triazolo[1,5-c]quinazoline-7-carbonitrile | 343 (1.72) |

The "right-side" precursor 2-(chloromethyl)-7-(methoxymethyl)-[1,2,4]triazolo[1,5-c]quinazolin-5-amine (Intermediate-13) was prepared in accordance with Scheme 10:

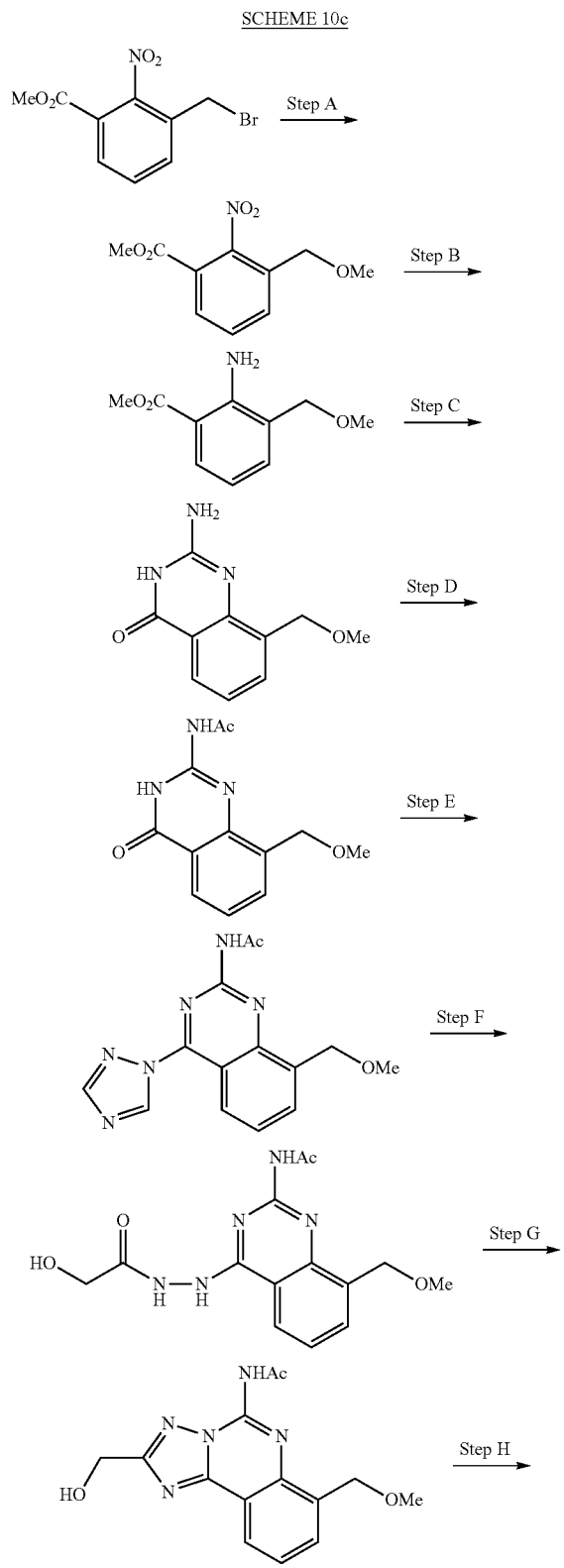

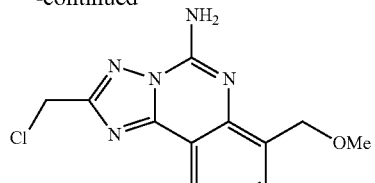

Intermediate-13

Step A: Methyl 3-(methoxymethyl)-2-nitrobenzoate

A mixture of methyl 3-(bromomethyl)-2-nitrobenzoate (2.00 g, 7.30 mmol) and K$_2$CO$_3$ (1.01 g, 7.30 mmol) in 100 mL of MeOH was heated at 80° C. for 2 h. The solvent was removed under vacuum. To the residue was added 150 mL of EtOAc. The mixture was washed with 150 mL of water, and the organic phase was dried over anhydrous Na$_2$SO$_4$. It was then concentrated. The residue was purified by flash chromatography eluting with 40% EtOAc/hexanes to give the title compound. $^1$H NMR (400 MHz, CDCl$_3$) δ 7.90-7.92 (m, 1H), 7.76-7.78 (m, 1H), 7.56-7.59 (m, 1H), 4.49 (s, 2H), 3.90 (s, 3H), 3.39 (s, 3H).

Step B: Methyl 2-amino-3-(methoxymethyl)benzoate

A solution of methyl 3-(methoxymethyl)-2-nitrobenzoate (850 mg, 3.77 mmol), diisopropylethylamine (0.125 ml, 0.755 mmol.) and Pd/C (402 mg, 0.377 mmol) in 20 mL: of MeOH was stirred at RT under a balloon of H$_2$ for 50 min. it was filtered through celite. The solvent was removed under vacuum. The residue was purified by column with 20% EtOAc/hexanes to give the title compound. $^1$H NMR (400 MHz, CDCl$_3$) δ 7.85-7.87 (m, 1H), 7.18-7.20 (m, 1H), 6.57-6.61 (m, 1H), 6.00-6.55 (brs, 2H), 4.49 (s, 2H), 3.86 (s, 3H), 3.32 (s, 3H).

Step C: 2-Amino-8-(methoxymethyl)quinazolin-4(3H)-one

To a solution of methyl 2-amino-3-(methoxymethyl)benzoate (388 mg, 1.99 mmol) in 7 mL of ether, was added 4 N HCl in ether (1.49 ml, 5.96 mmol). It was stirred at RT for 5 min and then treated with 10 mL: of hexanes. The resulting solid was collected by filtration to give 420 mg of its HCl salt form as a white solid. A mixture of this material (382 mg, 1.649 mmol) and cyanamide (416 mg, 9.89 mmol) was stirred in 3 mL ether for 5 min. Ether was removed under vacuum. The residue was stirred at 85° C. for 3 h. It was cooled to RT and diluted with 5 mL of ether. The solid was collected by filtration and washed with water. It was dried under vacuum to give the title compound. $^1$H NMR (400 MHz, DMSO) δ 10.80-11.05 (brs, 1H), 7.75-7.80 (m, 1H), 7.53-7.55 (m, 1H), 7.02-7.05 (m, 1H), 6.28-6.42 (brs, 2H), 4.62 (s, 2H), 3.30 (s, 3H).

Step D: N-(8-(Methoxymethyl)-4-oxo-3,4-dihydroquinazolin-2-yl)acetamide

A mixture of 2-amino-8-(methoxymethyl)quinazolin-4 (3H)-one (680 mg, 3.31 mmol) in 7 mL of Ac$_2$O was heated at 140° C. for 30 min. The solid was collected by filtration.

The filtrate was concentrated under vacuum. To the residue was added 5 mL of toluene. It was again concentrated under vacuum to remove the residual Ac$_2$O. The solid residue was combined with the solid from filtration to give the title compound. $^1$H NMR (400 MHz, CDCl$_3$) δ 8.18-8.20 (m, 1H), 7.69-7.75 (m, 1H), 7.36-7.40 (m, 1H), 4.76 (s, 2H), 3.49 (s, 3H), 2.33 (s, 3H).

Step E: N-(8-(Methoxymethyl)-4-(4H-1,2,4-triazol-4-yl)quinazolin-2-yl)acetamide

To a mixture of N-(8-(methoxymethyl)-4-oxo-3,4-dihydroquinazolin-2-yl)acetamide (320 mg, 1.29 mmol), and 4H-1,2,4-triazole (894 mg, 12.94 mmol) in 11 mL of acetonitrile, was added diisopropylethylamine (0.642 ml, 3.88 mmol) followed by phosphoryl trichloride (0.354 ml, 3.88 mmol). The reaction was stirred at RT for 3 h. The solid was collected by filtration and washed with acetonitrile and EtOH to give the crude title compound contaminated with some 4H-1,2,4-triazole. This material was used in future reactions without further purification. MS=299 [M+1].

Step F: N-(4-(2-(2-Hydroxyacetyl)hydrazinyl)-8-(methoxymethyl)quinazolin-2-yl)acetamide To a mixture of the crude N-(8-(methoxymethyl)-4-(4H-1,2,4-triazol-4-yl)quinazolin-2-yl)acetamide (306 mg, 1.026 mmol), 2-hydroxyacetohydrazide (110 mg, 1.22 mmol) in THF, was added diisopropylethylamine (0.203 ml, 1.231 mmol). The reaction was stirred at 60° C. overnight. The solid was filtered off. The filtrate was concentrated. The residue was purified by silica gel chromatography eluting with 10% MeOH/CH$_2$Cl$_2$ to give the title compound. LC/MS=320 [M+1].

Step G: (5-Amino-7-(methoxymethyl)-[1,2,4]triazolo[1,5-c]quinazolin-2-yl)methanol To a solution of N-(4-(2-(2-hydroxyacetyl)hydrazinyl)-8-(methoxymethyl)quinazolin-2-yl)acetamide (115 mg, 0.360 mmol) in MeOH was added 2 N aqueous NaOH (0.6 ml, 1.200 mmol). The reaction was stirred at RT for 1 h. It was neutralized by 2 N HCl. The solvent was removed under vacuum. To the residue was added trimethylsilyl N-(trimethylsilyl)acetimidate (1500 mg, 7.37 mmol). The reaction mixture was heated at 120° C. for 1.5 h. Trimethylsilyl N-(trimethylsilyl)acetimidate was removed under vacuum. To the residue were added 2 mL of MeOH and 1 drop of 12 N HCl. It was concentrated and the residue was purified by silica gel chromatography eluting with 10% MeOH/CH$_2$Cl$_2$ to give the title compound. LC/MS=360 [M+1].

Step H: 2-(Chloromethyl)-7-(methoxymethyl)-[1,2,4]triazolo[1,5-c]quinazolin-5-amine A solution of (5-amino-7-(methoxymethyl)-[1,2,4]triazolo[1,5-c]quinazolin-2-yl)methanol (40 mg, 0.15 mmol) in 3 mL of thionyl chloride was stirred at RT for 40 min. The solvent was removed under vacuum. The residue was purified by silica gel chromatography eluting with 8% MeOH/CH$_2$Cl$_2$ to give the title compound. $^1$H NMR (400 MHz, CDCl$_3$) δ 8.29-8.31 (m, 1H), 7.79-7.81 (m, 1H), 7.42-7.45 (m, 1H), 5.72-5.85 (brs 2H), 4.92 (s, 2H), 4.82 (s, 2H), 3.51 (s, 3H).

The compound Intermediate-13 was used to prepare compound Ex-198 in accordance with Scheme 10d:

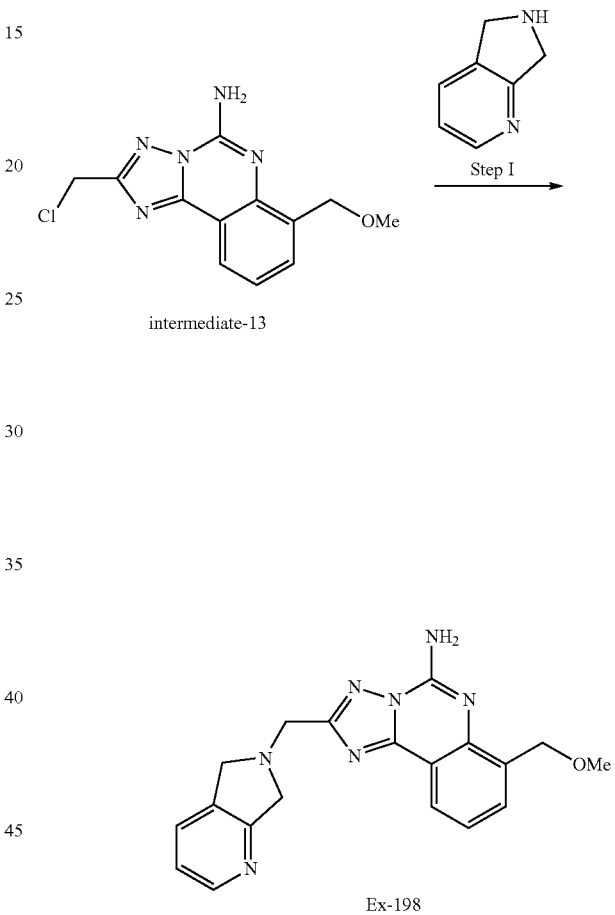

Preparation of 2-((5H-Pyrrolo[3,4-b]pyridin-6(7H)-yl)methyl)-7-(methoxymethyl)-[1,2,4]triazolo[1,5-c]quinazolin-5-amine (Ex-198)

To a solution of 2-(chloromethyl)-7-(methoxymethyl)-[1,2,4]triazolo[1,5-c]quinazolin-5-amine (6 mg, 0.022 mmol) and 6,7-dihydro-5H-pyrrolo[3,4-b]pyridine (8.34 mg, 0.043 mmol) in DMF, was added diisopropylethylamine (11.17 mg, 0.086 mmol). The reaction was stirred at 80° C. overnight. It was purified by a Gilson HPLC (eluant: H$_2$O: CH$_3$CN) to give a crude product, which was further purified by a prep-TLC plate eluting with 8% MeOH/CH$_2$Cl$_2$ to give the title compound. HPLC-MS t$_R$=1.76 min UV$_{254\ nm}$). Molecular weight calculated for formula C$_{19}$H$_{19}$N$_7$O: 361.4; observed: MH$^-$ (LCMS) 362.2.

The same method was used to prepare the following compound in Table XVIII.

TABLE XVIII

| Cmpd No. | Structure | ES-MS (M + 1) | LC-Mass ret. time |
|---|---|---|---|
| Ex-199 | 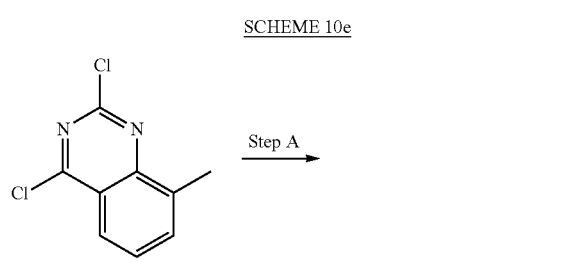 2-((5,6-dihydro-1,7-naphthyridin-7(8H)-yl)methyl)-7-(methoxymethyl)-[1,2,4]triazolo[1,5-c]quinazolin-5-amine | 376.2 | 0.81 |

The compound Intermediate-14 was used in synthesis of compound Ex-200 in accordance with Scheme 10e:

SCHEME 10e

Intermediate-14

-continued

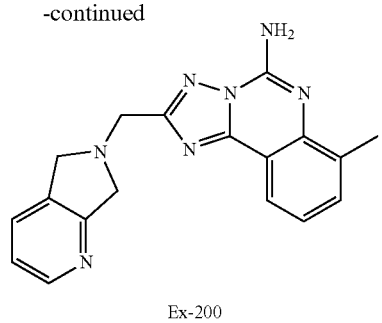

Ex-200

Step A: N'-(2-Chloro-8-methylquinazolin-4-yl)-2-hydroxyacetohydrazide

To a mixture of 2,4-dichloro-8-methylquinazoline (640 mg, 3.00 mmol) and 2-hydroxyacetohydrazide (284 mg, 3.15 mmol), was added 10 mL of THF, followed by diisopropylethylamine (0.745 ml, 4.51 mmol). The reaction was then heated at 65° C. for 3 h. It was cooled to RT and was diluted with 10 mL of $CH_2Cl_2$. The resulting mixture was stirred at RT for 30 min. The solid was collected by filtration and washed with $CH_2Cl_2$ to give the title compound. $^1H$ NMR (400 MHz, DMSO) δ 10.41 (brs, 1H), 10.09 (s, 1H), 8.08-8.12 (m, 1H), 7.68-7.72 (m, 1H), 7.41-7.47 (m, 1H), 5.60-5.66 (m, 1H), 4.02 (d, 2H), 2.50 (s, 3H).

Step B: N'-(2-((2,4-Dimethoxybenzyl)amino)-8-methylquinazolin-4-yl)-2-hydroxyacetohydrazide To a solution of N'-(2-chloro-8-methylquinazolin-4-yl)-2-hydroxyacetohydrazide (720 mg, 2.70 mmol) in 7 mL of DMSO, was added (2,4-dimethoxyphenyl)methanamine (655 mg, 3.91 mmol) and diisopropylethylamine (0.892 ml, 5.40 mmol). The reaction was stirred at 100° C. for 45 min. It was cooled to RT. To the reaction mixture was slowly added 50 mL of water. The solid was collected by filtration and dried under vacuum to give the title compound. $^1H$ NMR (400 MHz, DMSO) δ 10.76 (brs, 1H), 9.18 (brs, 1H), 7.59-7.62 (m, 1H), 7.11-7.30 (m, 2H), 6.82-6.88 (m, 2H), 6.38-6.51 (m, 2H), 5.80 (brs, 1H), 4.35 (brs, 2H), 3.65-3.88 (m, 8H), 2.14 (s, 3H).

Step C: 5-((2,4-Dimethoxybenzyl)amino)-7-methyl-[1,2,4]triazolo[1,5-c]quinazolin-2-yl)methanol A mixture of N'-(2-((2,4-dimethoxybenzyl)amino)-8-methylquinazolin-4-yl)-2-hydroxyacetohydrazide (1.05 g, 2.64 mmol) in 10 mL of trimethylsilyl N-(trimethylsilyl)acetimidate was heated at 110° C. for 1.5 h. Trimethylsilyl N-(trimethylsilyl)acetimidate was removed under vacuum. To the residue were added 2 mL of MeOH and 1 drop of 12 N HCl. It was concentrated and the residue was purified by flash chromatography eluting with 10% MeOH/CH$_2$Cl$_2$ to give the title compound. $^1$H NMR (400 MHz, DMSO) δ 8.23-8.27 (m, 1H), 7.95-8.02 (m, 1H), 7.52-7.57 (m, 1H), 7.20-7.25 (m, 2H), 6.53 (s, 1H), 6.39-6.41 (m, 1H), 5.54-5.62 (m, 1H), 4.57-4.71 (m, 4H), 3.81 (s, 3H), 3.68 (s, 3H), 2.47 (s, 3H).

Step D: 2-(Chloromethyl)-N-(2,4-dimethoxybenzyl)-7-methyl-[1,2,4]triazolo[1,5-c]quinazolin-5-amine To a solution of (5-((2,4-dimethoxybenzyl)amino)-7-methyl-[1,2,4]triazolo[1,5-c]quinazolin-2-yl)methanol (900 mg, 2.372 mmol) in 50 mL of CH$_2$Cl$_2$ was added triethylamine (1.091 ml, 7.83 mmol). It was cooled to 0° C. and then methanesulfonyl chloride (0.739 ml, 9.49 mmol) was added. The reaction was stirred at 0° C. for 40 min. It was diluted with 50 mL of CH$_2$Cl$_2$ and washed with water. The organic phase was dried over Na$_2$SO$_4$. It was then filtered and concentrated. The residue was dissolved in 50 mL of acetone. Lithium chloride (704 mg, 16.60 mmol) was added. The reaction was stirred at 65° C. for 2 h. Most of the solvent was removed under vacuum. The leftover was dissolved in 100 mL of CH$_2$Cl$_2$ and 50 mL of water. The organic was isolated and purified by flash chromatography eluting with 70% EtOAc/hexanes to give the title compound. LC/MS=398 [M+1].

Step E: 2-((5H-Pyrrolo[3,4-]pyridine-6(7H)-yl)methyl)-N-(2,4-dimethoxybenzyl)-7-methyl-[1,2,4]triazolo[1,5-c]quinazolin-5-amine To a solution of 2-(chloromethyl)-N-(2,4-dimethoxybenzyl)-7-methyl-[1,2,4]triazolo[1,5-c]quinazolin-5-amine (20 mg, 0.050 mmol) and 6,7-dihydro-5H-pyrrolo[3,4-b]pyridine (19.41 mg, 0.101 mmol) in 1 mL of DMF, was added diisopropylethylamine (26.0 mg, 0.201 mmol). The reaction was stirred at 80° C. overnight. It was purified by a Gilson HPLC (eluant: H$_2$O: CH$_3$CN) to give the title compound. $^1$H NMR (400 MHz, CDCl$_3$) δ 8.48 (d, 1H), 7.99 (d, 1H), 7.67 (d, 1H), 7.52 (d, 1H), 7.39 (d, 1H), 7.20-7.24 (m, 2H), 6.58-6.69 (brs, 1H), 6.40-6.47 (m, 2H), 4.94 (s, 4H), 4.72-4.78 (m, 4H), 3.87 (s, 3H), 3.76 (s, 3H), 2.66 (s, 3H).

Step F: 2-((5H-pyrrolo[3,4-b]pyridine-6(7H)-yl)methyl)-7-methyl-[1,2,4]triazolo[1,5-c]quinazolin-5-amine (Ex-200)

A solution of 2-((5H-pyrrolo[3,4-b]pyridine-6(7H)-yl)methyl)-N-(2,4-dimethoxybenzyl)-7-methyl-[1,2,4]triazolo[1,5-c]quinazolin-5-amine (32 mg, 0.066 mmol) in 1 mL of TFA was stirred at 45° C.' for 5 h in a sealed vial. The solvent was removed under vacuum. To the residue was added 0.5 mL of MeOH. To the mixture was added 15 mL of Et$_2$O/hexanes (1:1). The solid was collected by filtration to give crude product. This was further purified by a Gilson HPLC (eluant: H$_2$O:CH$_3$CN) to give the title compound. HPLC-MS t$_R$=1.82. min (UV$_{254\ nm}$). Molecular weight calculated for formula C$_{18}$H$_{17}$N$_7$: 331.2; observed MH$^+$ (LCMS) 332.2

Compound Ex-201 shown in Table XIX was prepared from Intermediate 14 and an appropriate "left-side" precursor in accordance with Scheme 10e.

TABLE XIX

| Compound No. | Structure | ES-MS (M +1) | LC-Mass retention time |
|---|---|---|---|
| Ex-201 | 2-((5,6-dihydro-1,7-naphthyridin-7(8H)-yl)methyl)-7-methyl-[1,2,4]triazolo[1,5-c]quinazolin-5-amine | 346.2 | 1.85 |

Example 11: 2-((5,6-dihydro-1,7-naphthyridin-7(8H)-yl)methyl-7-(2-fluoroethoxy)-[1,2,4]triazolo[1,5-c]quinazolin-5-amine (Ex-202)

Compound Ex-202 was prepared from the previously exemplified compound Ex-135 (see above).

SCHEME 11

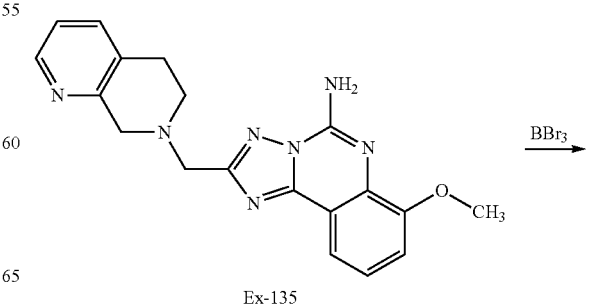

Ex-135

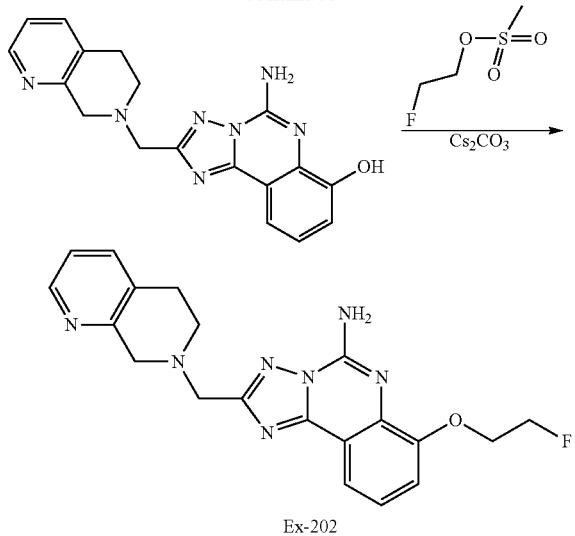

Step A: 5-amino-2-((5,6-dihydro-1,7-naphthyridin-7(8H)-yl)methyl)-[1,2,4]triazolo[1,5-c]quinazolin-7-ol To a suspension of compound Ex-135(2-((5,6-dihydro-1,7-naphthyridin-7(8H)-yl)methyl)-7-methoxy-[1,2,4]triazolo[1,5-c]quinazolin-5-amine, prepared above, 350 mg, 0.968 mmol) in DCE (4 ml) was added $BBr_3$ (4.84 ml, 9.68 mmol). The reaction mixture was stirred in a sealed tube at 90° C. for 18 h. The mixture was cooled down and concentrated in vacuo to yield the corresponding 7-alcohol. LC/MS=348 [M+1].

Step B: 2-((5,6-dihydro-1,7-naphthyridin-7(8H)-yl)methyl)-7-(2-fluoroethoxy)-[1,2,4]triazolo[1,5-c]quinazolin-5-amine To a solution of 5-amino-2-((5,6-dihydro-1,7-naphthyridin-7(8H)-yl)methyl)-[1,2,4]triazolo[1,5-c]quinazolin-7-ol (the 7-alcohol prepared in Step A, 30 mg, 0.086 mmol) in DMF (2 ml) was added $Cs_2CO_3$ (84 mg, 0.259 mmol) and 2-fluoroethyl tosylate (22.62 mg, 0.104 mmol). Reaction mixture was stirred at room temperature for 18 h, diluted with DCM. The organic layer was washed with $H_2O$, dried over $MgSO_4$, filtered and concentrated in vacuo. Purification by Preparative TLC (DCM: MeOH (7N $NH_3$) 1:20) to yield compound. Ex-202 LC/MS=394 [M+1]. HPLC Retention time 1.53 min.

Additional compounds of the invention were prepared in accordance with Scheme 11 from the corresponding 7-methoxy compound and are presented in Table XX.

TABLE XX

| Compound No. | Structure | LC-MS | Retention Time (min) |
|---|---|---|---|
| Ex-203 | 2-((5H-pyrrolo[3,4-b]pyridin-6(7H)-yl)methyl)-7-ethoxy-[1,2,4]triazolo[1,5-c]quinazolin-5-amine | 362 [M + 1]. | .58 |
| Ex-204 | 2-((5,6-dihydro-1,7-naphthyridin-7(8H)-yl)methyl)-7-ethoxy-[1,2,4]triazolo[1,5-c]quinazolin-5-amine | 376 [M + 1]. | .60 |

TABLE XX-continued

| Compound No. | Structure | LC-MS | Retention Time (min) |
|---|---|---|---|
| Ex-205 | 2-((5,6-dihydro-1,7-naphthyridin-7(8H)-yl)methyl)-7-(fluoromethoxy)-[1,2,4]triazolo[1,5-c]quinazolin-5-amine | 380 [M + 1]. | .58 |

Example 12: Preparation of Compounds of the Invention with Alkyl-Substituted Linker

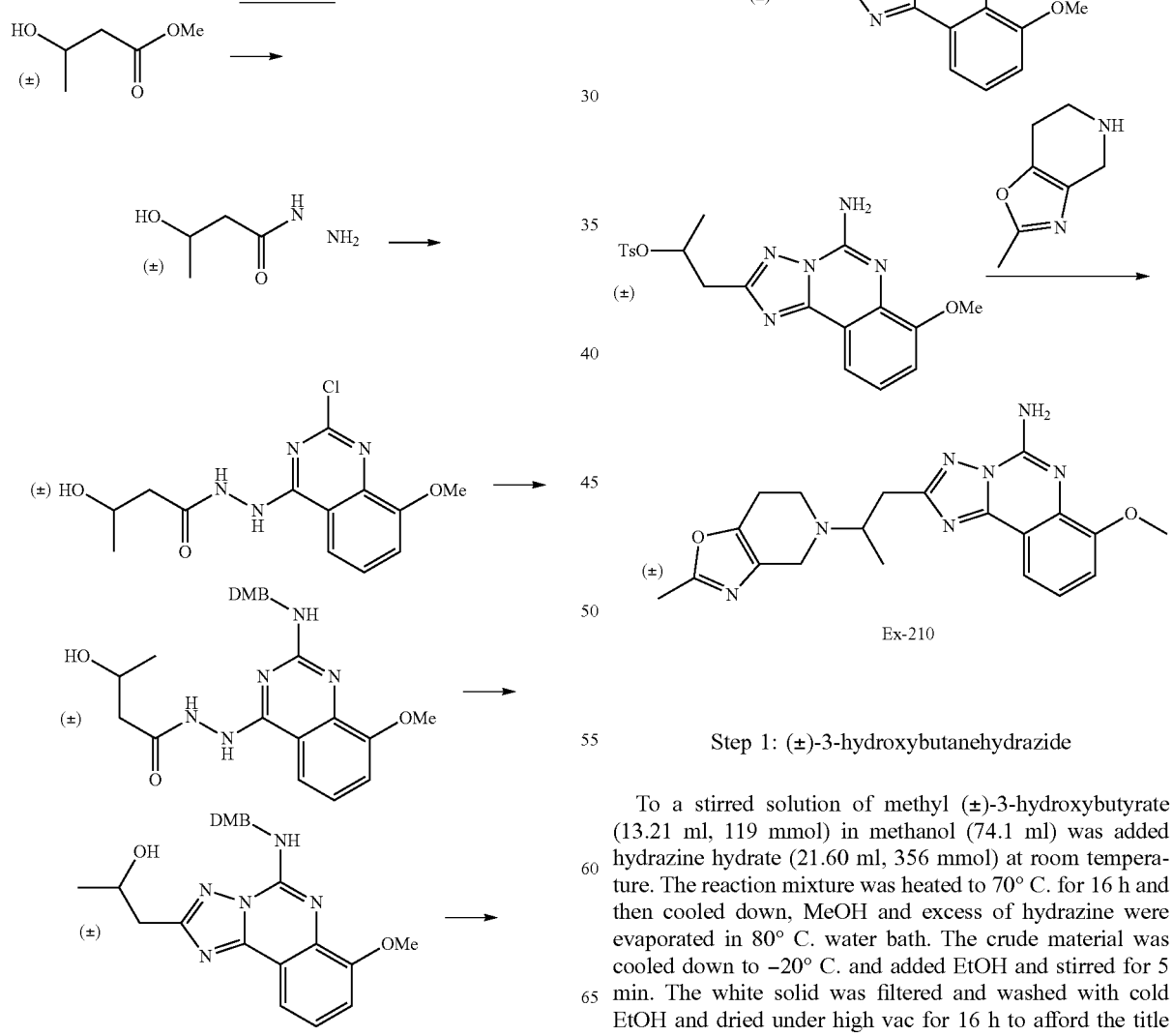

SCHEME 12

Step 1: (±)-3-hydroxybutanehydrazide

To a stirred solution of methyl (±)-3-hydroxybutyrate (13.21 ml, 119 mmol) in methanol (74.1 ml) was added hydrazine hydrate (21.60 ml, 356 mmol) at room temperature. The reaction mixture was heated to 70° C. for 16 h and then cooled down, MeOH and excess of hydrazine were evaporated in 80° C. water bath. The crude material was cooled down to −20° C. and added EtOH and stirred for 5 min. The white solid was filtered and washed with cold EtOH and dried under high vac for 16 h to afford the title compound which was characterized by H NMR.

Step 2: (±)-N'-(2-chloro-8-methoxyquinazolin-4-yl)-3-hydroxybutanehydrazide

To a stirred suspension of 2,4-dichloro-8-methoxyquinazoline (25 g, 109 mmol) in 1,4-dioxane (404 ml) was added DIPEA (42.9 ml, 246 mmol) and (±)-3-hydroxybutane-hydrazide (14.18 g, 120 mmol) at room temperature. The reaction mixture was heated to 60° C.' for 16 h. After cooling, the reaction mixture was used for the next step without aqueous work-up and purification. LC/MS=311 [M+1].

Step 3: (±)-N'-(2-((2,4-dimethoxybenzyl)amino)-8-methoxyquinazolin-4-yl)-3-hydroxybutanehydrazide To a reaction mixture vessel of step B (33.9 g, 109 mmol) was added DIPEA (32.4 ml, 185 mmol) and (2,4-dimethoxyphenyl)methanamine (24.58 ml, 164 mmol) at room temperature. The reaction mixture was heated to 100° C. for 16 h. cooled to room temperature, and the solvent was evaporated. The crude product was used for the next step without aqueous work-up and any further purification. LC/MS=442 [M+1].

Step 4: (±)-1-((2,4-dimethoxybenzyl)amino)-7-methoxy-[1,2,4]triazolo[1,5-c]quinazolin-2-yl)propan-2-ol To a pressure tube of the reaction mixture of step C (48.2 g, 109 mmol) was added (E)-trimethylsilyl N-(trimethylsilyl)acetimidate (BSTA, 320 ml, 1310 mmol) at room temperature. The pressure tube was capped and heated to 120° C. for 16 h. After cooling, the reaction mixture was concentrated in vacuo with heating. The residue was dissolved in MeOH (500 ml) and added 4N HCl in dioxane (40.9 ml, 164 mmol) at 0° C.

The reaction mixture was stirred at RT for 40 min and cold aq. saturated NaHCO₃ (1 L) was added. White precipitates were generated, filtered, washed with water. The wet white solid was redissolved in 10% MeOH/DCM (2 L). The organic layer was dried over MgSO₄, filtered and concentrated to afford the title compound which was characterized by using LC/MS=424 [M+1] and H NMR.

Step 5: (±)-1-(5-((2,4-dimethoxybenzyl)amino)-7-methoxy-[1,2,4]triazolo[1,5-c]quinazolin-2-yl)propan-2-yl 4-methylbenzenesulfonate To a stirred suspension of (±)-1-(5-((2,4-dimethoxybenzyl)amino)-7-methoxy-[1,2,4]triazolo[1,5-c]quinazolin-2-yl)propan-2-ol (47.7 g, 113 mmol) in DCM (1126 ml) was added DMAP (20.64 g, 169 mmol), triethylamine (39.3 ml, 282 mmol) at room temperature. The reaction mixture was cooled down to 0° C. and then p-toluenesulfonyl chloride (32.2 g, 169 mmol) was added slowly. The reaction mixture was stirred at room temperature for 6 h. The reaction mixture was diluted with DCM. The organic layer was washed with 1N HCl (aq, 2 L), water (1 L), sat. NaHCO₃ (1 L) and brine solution (1 L), dried over MgSO4, filtered and concentrated. The crude product was purified by flash chromatography (EtOAc:Hexanes 5:1) to afford the title compound which was characterized using, LC/MS=578 [M+1].

Step 6: (±)-1-(5-amino-7-methoxy-[1,2,4]triazolo[1,5-c]quinazolin-2-yl)propan-2-yl 4-methylbenzenesulfonate To a (±)-1-(5-((2,4-dimethoxybenzyl)amino)-7-methoxy-[1,2,4]triazolo[1,5-c]quinazolin-2-yl)propan-2-yl 4-methylbenzenesulfonate (57 g, 99 mmol) was added TFA (658 ml) at room temperature. The reaction mixture was heated to 55° C. for 4 h and cooled down to room temperature. TFA was evaporated and aq. saturated NaHCO₃ was added. The purple precipitates were generated and diluted with 10% MeOH/DCM. The heterogeneous mixture was stirred at for 4 h and filtered insoluble purple solid. The organic layer was dried over MgSO₄, filtered and concentrated. The crude product was purified by flash chromatography (from EtOAc:Hexanes 1:1 to 10% MeOH/DCM) to afford the title compound which was characterized using, LC/MS=428 [M+1].

Step 7: (±)-7-methoxy-2-(2-(2-methyl-6,7-dihydrooxazolo[4,5-c]pyridin-5(4H)-yl)propyl)-[1,2,4]triazolo[1,5-c]quinazolin-5-amine (Ex-210) [

To (±)-1-(5-amino-7-methoxy-[1,2,4]triazolo[1,5-c]quinazolin-2-yl)propan-2-yl 4-methylbenzenesulfonate (200 mg, 0.468 mmol) in 1,4-dioxane (3200 µL) was added DIPEA (163 µL, 0.936 mmol), and 2-methyl-4,5,6,7-tetrahydrooxazolo[4,5-c]pyridine (129 mg, 0.936 mmol) at room temperature. The reaction mixture was stirred at 100° C. for 16 h. After cooling, the solvent was evaporated and the crude product was purified by flash chromatography (from EtOAc:Hexanes 1:1 to 10% MeOH/DCM) to afford the compound Ex-210 which was characterized using, LC/MS=394 [M+1] and H NMR.

The compounds shown in Table XXI were prepared by using methods described in Examples 12. Enantiomeric forms were obtained from the racemate by separation through chiral HPLC.

TABLE XXI

| Compound No. | Structure | LC-MS |
| --- | --- | --- |
| Ex-211 | (R)-7-methoxy-2-(2-(2-methyl-6,7-dihydrooxazolo[5,4-c]pyridin-5(4H)-yl)propyl)-[1,2,4]triazolo[1,5-c]quinazolin-5-amine | 394 [M + 1] |

TABLE XXI-continued

| Compound No. | Structure | LC-MS |
|---|---|---|
| Ex-212 | (S)-7-methoxy-2-(2-(2-methyl-6,7-dihydrooxazolo[5,4-c]pyridin-5(4H)-yl)propyl)-[1,2,4]triazolo[1,5-c]quinazolin-5-amine | 394 [M + 1] |
| Ex-214 | (R)-7-methoxy-2-(2-(2-methyl-6,7-dihydrooxazolo[4,5-c]pyridin-5(4H)-yl)propyl)-[1,2,4]triazolo[1,5-c]quinazolin-5-amine | 394 [M + 1] |
| Ex-215 | (S)-7-methoxy-2-(2-(2-methyl-6,7-dihydrooxazolo[4,5-c]pyridin-5(4H)-yl)propyl)-[1,2,4]triazolo[1,5-c]quinazolin-5-amine | 394 [M + 1] |
| Ex-216 | (R)-7-methoxy-2-(2-(2-methyl-6,7-dihydrothiazolo[5,4-c]pyridin-5(4H)-yl)propyl)-(1,2,4]triazolo[1,5-c]quinazolin-5-amine | 410 [M + 1] |
| Ex-217 | (S)-7-methoxy-2-(2-(2-methyl-6,7-dihydrothiazolo[5,4-c]pyridin-5(4H)-yl)propyl)-[1,2,4]triazolo[1,5-c]quinazolin-5-amine | 410 [M + 1] |

TABLE XXI-continued

| Compound No. | Structure | LC-MS |
|---|---|---|
| Ex-218 | (R)-7-methoxy-2-(2-(2-methyl-6,7-dihydrothiazolo[4,5-c]pyridin-5(4H)-yl)propyl)-[1,2,4]triazolo[1,5-c]quinazolin-5-amine | 410 [M + 1] |
| Ex-219 | (S)-7-methoxy-2-(2-(2-methyl-6,7-dihydrothiazolo[4,5-c]pyridin-5(4H)-yl)propyl)-[1,2,4]triazolo[1,5-c]quinazolin-5-amine | 410 [M + 1] |
| Ex-220 | (R)-7-methoxy-2-(2-(2-methyl-4H-pyrrolo[3,4-d]thiazol-5(6H)-yl)propyl)-[1,2,4]triazolo[1,5-c]quinazolin-5-amine | 396 [M + 1] |
| Ex-221 | (R)-7-methoxy-2-(2-(2-methyl-6,7-dihydropyrazolo[1,5-a]pyrazin-5(4H)-yl)propyl)-[1,2,4]triazolo[1,5-c]quinazolin-5-amine | 393 [M + 1] |
| Ex-222 | (S)-7-methoxy-2-(2-(2-methyl-6,7-dihydropyrazolo[1,5-a]pyrazin-5(4H)-yl)propyl)-[1,2,4]triazolo[1,5-c]quinazolin-5-amine | 393 [M + 1] |

TABLE XXI-continued

| Compound No. | Structure | LC-MS |
|---|---|---|
| Ex-223 | (R)-2-(2-(2-difluoromethyl)-6,7-dihydropyrazolo[1,5-a]pyrazin-5(4H)-yl(propyl)-7-methoxy-[1,2,4]triazolo[1,5-c]quinazolin-5-amine | 429 [M + 1] |
| Ex-224 | (S)-2-(2-(2-(difluoromethyl)-6,7-dihydropyrazolo[1,5-a]pyrazin-5(4H)-yl)propyl)-7-methoxy-[1,2,4]triazolo[1,5-c]quinazolin-5-amine | 429 [M + 1] |
| Ex-225 | (R)-2-(2-(2-(difluoromethyl)-6,7-dihydrothiazolo[5,4-c]pyridin-5(4H)-yl)propyl)-7-methoxy-[1,2,4]triazolo[1,5-c]quinazolin-5-amine | 446 [M + 1] |
| Ex-226 | (S)-7-methoxy-2-(2-(2-(trifluoromethyl)-6,7-dihydrothiazolo[4,5-c]pyridin-5(4H)-yl)propyl)-[1,2,4]triazolo[1,5-c]quinazolin-5-amine | 464 [M + 1] |

TABLE XXI-continued

| Compound No. | Structure | LC-MS |
|---|---|---|
| Ex-247 | (R)-7-methoxy-2-(2-(2-methyl-4H-pyrrolo[3,4-d]oxazol-5(6H)-yl)propyl)-[1,2,4]triazolo[1,5-c]quinazolin-5-amine | 380 [M + 1] |
| Ex-248 | (R)-7-methoxy-2-(2-(2-methyl-4H-pyrrolo[3,4-d]oxazol-5(6H)-yl)butyl)-[1,2,4]triazolo[1,5-c]quinazolin-5-amine | 394 [M + 1] |

Example 13: Preparation of 2-(3-(5H-pyrrolo[3,4-b]pyridin-6(7H)-yl)propyl)-7-methoxy-[1,2,4]triazolo[1,5-c]quinazolin-5-amine (EX-227)

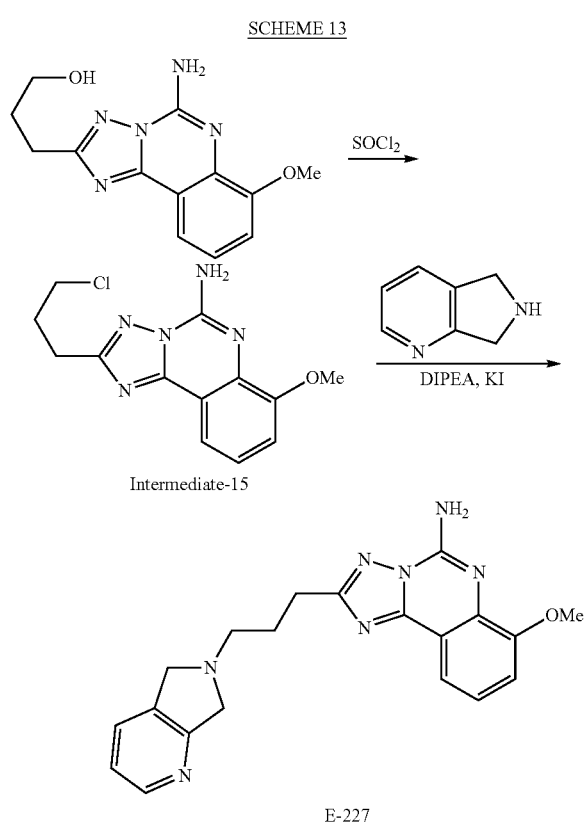

Step A: Preparation of 2-(3-chloropropyl)-7-methoxy-[1,2,4]triazolo[1,5-c]quinazolin-5-amine (Intermediate-15)

Into SOCl$_2$ (25 ml) was suspended 3-(5-amino-7-methoxy-[1,2,4]triazolo[1,5-c]quinazolin-2-yl)propan-1-ol (240 mg, 0.878 mmol). The mixture was stirred at RT for 1 h and concentrated in vacuo to remove SOCl$_2$ completely providing to afford compound Intermediate-15, LC/MS=293 [M+1].

Step B: Preparation of 2-(3-(5H-pyrrolo[3,4-b]pyridin-6(7H)-yl)propyl)-7-methoxy-[1,2,4]triazolo[1,5-c]quinazolin-5-amine (Ex-227)

2-(3-chloropropyl)-7-methoxy-[1,2,4]triazolo[1,5-c]quinazolin-5-amine (80 mg, 0.286 mmol), 6,7-dihydro-5H-pyrrolo[3,4-b]pyridine (75 mg, 0.86 mmol), and KI (142 mg, 0.858 mmol) in DMF (2 mL) was stirred at 80° C. for 18 h. The mixture was cooled down to RT, diluted with DCM, washed with H$_2$O (3 X), dried and concentrated. Chromatography purification MeOH/DCM (1:30-1:20-1:10) afforded compound Ex-227. LC/MS=379 [M+1].

Additional compounds of the invention, presented in Table XXII, below, were prepared using Intermediate-15 and an appropriate left-side intermediate.

TABLE XXII

| Compound No. | Structure | LC-MS |
|---|---|---|
| Ex-228 | 2-(3-(4-fluoroisoindolin-2-yl)propyl)-7-methoxy-[1,2,4]triazolo[1,5-c]quinazolin-5-amine | 393 [M + 1]. |
| Ex-229 | 2-(3-(5-fluoroisoindolin-2-yl(propyl)-7-methoxy-[1,2,4]triazolo[1,5-c]quinazolin-5-amine | 393 [M + 1]. |
| Ex-230 | 7-methoxy-2-(3-(5-(trifluoromethyl)isoindolin-2-yl)propyl)-[1,2,4]triazolo[1,5-c]quinazolin-5-amine | 443 [M + 1]. |

Example 14: Preparation of 7-Methoxy-2-(2-(2,7,7-trimethyl-6,7-dihydro-oxazolo[5,4-c]pyridin-5(4H)-yl)ethyl)-[1,2,4]triazolo[1,5-c]quinazolin-5-amine, TFA (Ex-235)

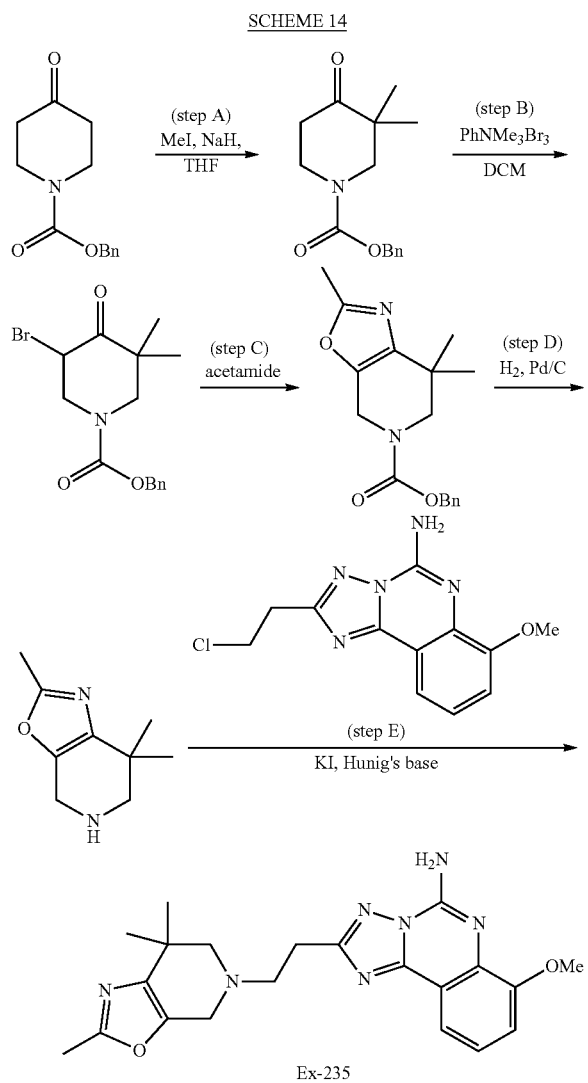

Step A: Benzyl 3,3-dimethyl-4-oxopiperidine-1-carboxylate

Benzyl 4-oxopiperidine-1-carboxylate (5 g, 21 mmol) in THF (50 ml) was cooled to 0° C. Sodium hydride (1.1 g, 43 mmol), then iodomethane (3.0 ml, 47 mmol) was added slowly. Mixture was stirred at 0° C. for 2 hours, then slowly warm up to room temperature and stirred overnight. Saturated aq. NH$_4$Cl solution was added and the product was extracted with EtOAc. The extract was washed with brine, dried over anhydrous sodium sulfate, and concentrated. The crude product thus obtained was purified by column chromatography on a 100 gram-size silica gel column, eluting with gradient EtOAc/hexane to afford the titled product as colorless oil.

Step B: Benzyl 5-bromo-3,3-dimethyl-4-oxopiperidine-1-carboxylate

Benzyl 3,3-dimethyl-4-oxopiperidine-1-carboxylate (0.7 g, 2.7 mmol) in DCM (10 ml) was mixed with phenyltrimethylammonium tribromide (1.1 g, 3.0 mmol) and stirred at room temperature for 4 hours. Mixture was diluted with DCM, and washed with water and dried over anhydrous sodium sulfate. The crude mixture was concentrated, diethyl ether added, and the resulting precipitate filtered off. The solution was concentrated to afford the titled compound, and used in the next step without further purification.

Step C: Benzyl 2,7,7-trimethyl-6,7-dihydrooxazolo[5,4-c]pyridine-5(4H)-carboxylate Benzyl 5-bromo-3,3-dimethyl-4-oxopiperidine-1-carboxylate (0.85 g, 2.5 mmol) from step B was mixed with acetamide (0.74 g, 12.5 mmol), and heated to 120° C. and stirred for an additional 1.5 hours. After cooling to room temperature, mixture was diluted with DCM, washed with water, dried over anhydrous sodium sulfate, and the solution was concentrated. The concentrate was purified by silica gel flash chromatography, eluting with gradient (1:2 ether/DCM-hexane). UV wavelength for collection was set to 210 nm. The titled product was obtained as colorless oil.

Step D: 2,7,7-Trimethyl-4,5,7-tetrahydrooxazolo[5,4-c]pyridine

Benzyl 2,7,7-trimethyl-6,7-dihydrooxazolo[5,4-c]pyridine-5(4H)-carboxylate (0.17 g, 0.57 mmol) in MeOH (8 ml) was mixed with 10% palladium on carbon (0.050 g) and stirred under balloon hydrogen for 2 hours. The mixture was filtered, and solution was concentrated to give the titled product as oil.

Step E: 7-Methoxy-2-(2-(2,7,7-trimethyl-6,7-dihydrooxazolo[5,4-c]pyridin-5(4H)-yl)ethyl)-[1,2,4]triazolo[1,5-c]quinazolin-5-amine, TFA 2-(2-Chloroethyl)-7-methoxy-[1,2,4]triazolo[1,5-c]quinazolin-5-amine (0.12 g, 0.43 mmol) was mixed with 2,7,7-trimethyl-4,5,6,7-tetrahydrooxazolo[5,4-c]pyridine (0.072 g, 0.43 mmol), KI (0.22 g, 1.3 mmol), and Hunig's base (0.075 ml, 0.43 mmol) in DMF (1.5 ml), then heated to 80° C. for 15 hours. The mixture was diluted with DMF, and filtered. The solution was purified by preparative reverse phase HPLC (C-18), eluting with acetonitrile/water+0.1% TFA, to afford Ex-235 which was characterized by LC/MS. LC/MS=408 [M+1].

Scheme 14a illustrates a variation on the preparation shown in Scheme 14.

SCHEME 14a

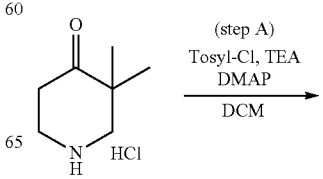

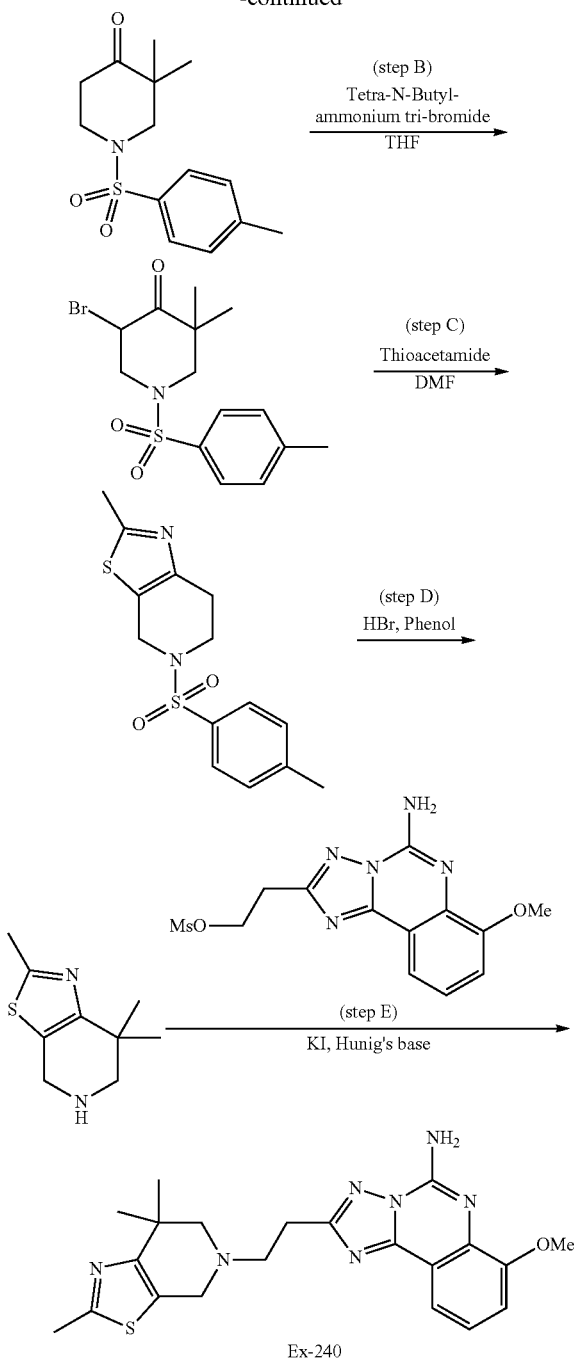

dried over anhydrous sodium sulfate, and concentrated to afford the titled product that was used in the next step without further purification Step B: 5-Bromo-3,3-dimethyl-1-tosylpiperidin-4-one To a stirred solution of 3,3-dimethyl-1-tosylpiperidin-4-one (4.4 g, 16.0 mmol) in THF (32 ml) at room temperature, under an atmosphere of nitrogen, was added tetrabutylammonium tribromide (8.3 g, 17.2 mmol) and the mixture was stirred overnight. The reaction mixture was diluted with ethyl acetate (100 ml) and washed with 1 N HCl (47 ml), water (50 ml), and brine (50 ml), then dried over anhydrous sodium sulfate, and concentrated. The crude was chromatographed on silica, eluting with hexane/ethyl acetate (0-100%, 30 min) to give the titled product as a white solid.

Step C: 2,7,7-Trimethyl-5-tosyl-4,5,6,7-tetrahydrothiazolo[5,4-c]pyridine

To a stirred solution of 5-bromo-3, 3-dimethyl-1-tosylpiperidin-4-one (2.5 g, 7.0 mmol) in DMF (15 ml) under an atmosphere of nitrogen was added thioacetamide (0.63 g, 8.3 mmol). The mixture was stirred at 70° C. for 2 hours. The reaction mixture was cooled to room temperature, diluted with ethyl acetate (100 ml), washed with water (50 ml), brine (50 ml), then dried over anhydrous sodium sulfate. The solvent was evaporated, and the crude was chromatographed on silica, eluting with hexane/ethyl acetate (0-100%, 25 minute) to afford the titled product as a white solid.

Step D: 2,7,7-Trimethyl-4,5,6,7-tetrahydrothiazolo[5,4-c]pyridine

Into a round bottle flask containing 2,7,7-trimethyl-5-tosyl-4,5,6,7-tetrahydrothiazolo[5,4-c]pyridine (1.42 g, 4.22 mmol) was added HBr (25 ml, 244 mmol), and phenol (0.4 g, 4.22 mmol). The reaction was stirred at 90° C. for 1 hour and then cooled to room temperature. The reaction mixture was diluted with water (30 ml) and extracted with diethyl ether (2×50 ml). The aqueous layer was made basic (pH=14) with sodium hydroxide and the product was extracted into $CH_2Cl_2$/MeOH(10%) (3×100 ml)). After drying over anhydrous sodium sulfate, and the solvent was evaporated to afford the titled product that was used in the next step without further purification.

Step E: Preparation of 7-Methoxy-2-(2-(2,7,7-trimethyl-6,7-dihydrothiazolo[5,4-c]pyridin-5(4H)-yl)ethyl)-[1,2,4]triazolo[1,5-c]quinazolin-5-amine (Ex-240)

Into a stirred solution of 2-(5-amino-7-methoxy-[1,2,4]triazolo[1,5-c]quinazolin-2-yl)ethyl methanesulfonate (1.39 g, 4.1 mmol) in dioxane/water (4:1, 20 ml) was added 2,7,7-trimethyl-4,5,6,7-tetrahydrothiazo [5,4-c]pyridine (0.50 g, 2.7 mmol), KI (0.46 g, 2.7 mmol), and Hunig's base (0.50 ml, 2.7 mmol). The reaction mixture was stirred at 70° C. for 15 hours. The reaction mixture was loaded on to a 100 gram C18-reverse phase Biotage column eluting with water/acetonitrile+0.1% TFA (0-30%, 30 min). The product was collected and acetonitrile was evaporated. The water layer was extracted with ethyl acetate (3×30 ml), and the ethyl acetate layer was washed with saturated $NaHCO_3$ (50 ml), water (50 ml), and brine (50 ml). After drying over $MgSO_4$, Step A: 3,3-Dimethyl-1-tosylpiperidin-4-one 3,3-Dimethylpiperidin-4-one hydrochloride (4 g, 24.4 mmol) in DCM (50 ml) under an atmosphere of nitrogen was stirred and cooled to 0° C. Tosyl chloride (4.7 g, 24.4 mmol), DMAP (3.0 g, 24.4 mmol) and TEA (6.82 ml, 49 mmol) were added. The reaction mixture was stirred at 0° C. for 2 hours, and then with continued stirring, warmed to room temperature overnight. Water was added to the reaction mixture (100 ml). The product was extracted into $CH_2Cl_2$ (3×50 ml). The organic layer was washed with brine (50 ml), the mixture was filtered and the solvent was evaporated to afford Ex-240 as a white solid, which was characterized by LC/MS. LC/MS=424 [M+1].

Example 15: Preparation of 2-(2-(2,4-dimethyl-6,7-dihydrooxazolo[5,4-c]pyridin-5(4H)-yl)ethyl)-7-methoxy-[1,2,4]triazolo[1,5-c]quinazolin-5-amine (Ex-236) and Preparation of 2-(2-(2,6-dimethyl-6,7-dihydrooxazolo[5,4-c]pyridin-5(4H)-yl)ethyl)-7-methoxy-[1,2,4]triazolo[1,5-c]quinazolin-5-amine (Ex-237)

SCHEME 15

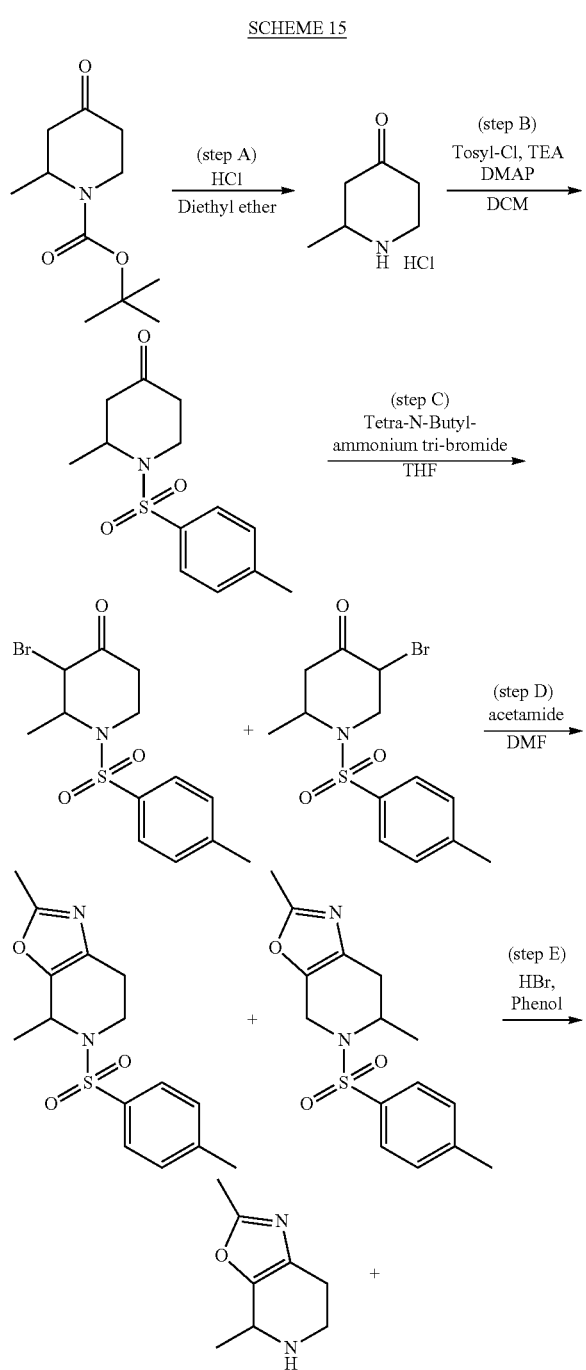

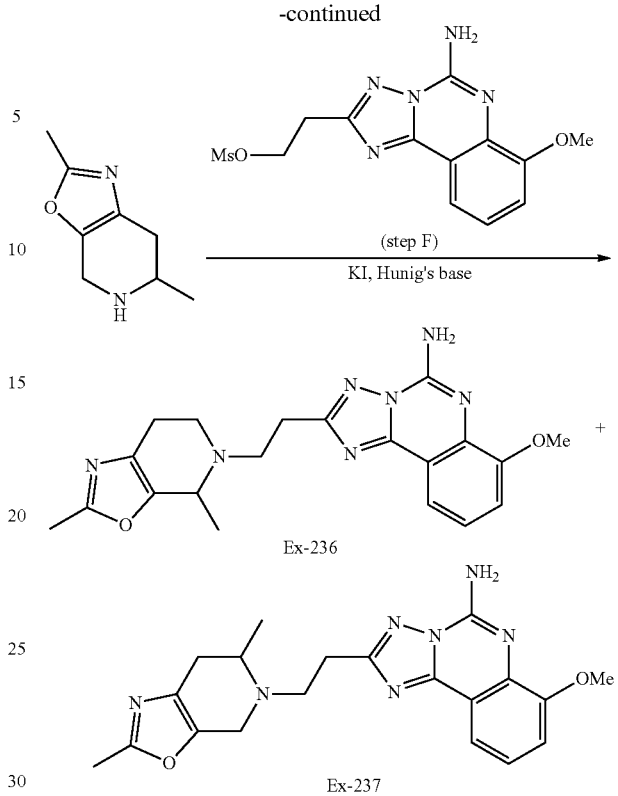

Step A: 2-Methylpiperidin-4-one hydrochloride

To a round bottle flask containing tert-butyl-2-methyl-4-oxopiperidine-1-carboxylate (5 g, 23 mmol) under an atmosphere of nitrogen at 0° C. was added hydrochloric acid in diethyl ether (24 ml, 47 mmol). The reaction mixture was stirred at 0° C. for 2 hours, and then slowly stirred to room temperature overnight. The solvent was evaporated to afford a white solid as the titled product, which was further dried on high vacuum for 3 hours, before using in the next step.

Step B: 2-Methyl-1-tosylpiperidin-4-one

2-Methylpiperidin-4-one hydrochloride (3.51 g, 23 mmol) in DCM (50 ml) under an atmosphere of nitrogen was stirred and cooled to 0° C. Tosyl chloride (5 g, 26 mmol), and TEA (11 ml, 77 mmol) were added. The reaction mixture was stirred at 0° C. for 2 hours, then with continued stirring, warmed to room temperature overnight. 1 N HCl (94 ml) was added to the reaction mixture. The product was extracted into $CH_2Cl_2$ (3×50 ml). The organic layer was washed with brine (50 ml), dried over anhydrous sodium sulfate, and concentrated. The crude was chromatographed on silica, eluting with hexane/ethyl acetate (0-100%) to afford the titled product.

Step C: 3-Bromo-2-methyl-1-tosylpiperidin-4-one and 5-bromo-2-methyl-1-tosylpiperidin-4-one To a stirred solution of 2-methyl-1-tosylpiperidin-4-one (6.0 g, 23.0 mmol) in THF (32 ml) at room temperature, under an atmosphere of nitrogen, was added tetrabutylammonium tribromide (10.0 g, 23. mmol) and the mixture was stirred overnight. The reaction mixture was diluted with ethyl acetate (100 ml) and washed with 1 N HCl (47 ml), water (50 ml), and brine (50 ml), dried over anhydrous sodium sulfate, and concentrated. The titled products were obtained as a mixture of regioisomers that were used in the next step without purification.

Step D: 2,4,Dimethyl-5-tosyl-4,5,6,7-tetrahydroox-azolo[5,4-c]pyridine and 2,6,dimethyl-5-tosyl-4,5,6,7-tetrahydrooxazolo[5,4-c]pyridine To a round bottom flask containing compounds 3-bromo-2-methyl-1-tosylpiperidin-4-one and 5-bromo-2-methyl-1-tosylpiperidin-4-one (3.2 g, 9.2 mmol) was added acetamide (2.73 g, 46.2 mmol) and the mixture was stirred to 120° C. for 2 hours. The reaction mixture was cooled to room temperature and diluted with ethyl acetate (100 ml), then washed with water (50 ml), and brine (50 ml). After drying over anhydrous sodium sulfate, the solvent was evaporated. The crude was chromatographed on silica, eluting with hexane/ethyl acetate (0-50%) to afford the titled products as a white solid.

Step E: 2,4-Dimethyl-4,5,6,7-tetrahydrooxazolo[5,4-c]pyridine and 2,6-dimethyl-4,5,6,7-tetrahydrooxazolo[5,4-c]pyridine To a round bottom flask containing compounds 2,4,dimethyl-5-tosyl-4,5,6,7-tetrahydrooxazolo[5,4-c]pyridine and 2,6,dimethyl-5-tosyl-4,5,6,7-tetrahydrooxazolo[5,4-c]pyridine (0.60 g, 2.0 mmol) was added HBr (11.5 ml, 102 mmol), and phenol (0.2 g, 2.0 mmol). The reaction mixture was stirred at 90° C. for 1 hour and then cooled to room temperature. The reaction mixture was diluted with water (30 ml) and extracted with diethyl ether (2×50 ml). The aqueous layer was made basic (pH=14) with sodium hydroxide and the product was extracted into $CH_2Cl_2$/MeOH(10%) (3×100 ml)). After drying over anhydrous sodium sulfate, and filtered, the solvent was evaporated to afford the titled products, which were used in the next step without further purification.

Step F: Preparation of 2-(2-(2,4-dimethyl-6,7-dihydrooxazolo[5,4-c]pyridin-5(4H)-yl)ethyl)-7-methoxy-[1,2,4]triazolo[1,5-c]quinazolin-5-amine (Ex-236) and Preparation of 2-(2-(2,6-dimethyl-6,7-dihydrooxazolo[5,4-c]pyridin-5(4H)-yl)ethyl)-7-methoxy-[1,2,4]triazolo[1,5-c]quinazolin-5-amine (Ex-237)

To a stirred solution of 2-(5-amino-7-methoxy-[1,2,4]triazolo[1,5-c]quinazolin-2-yl)ethyl methanesulfonate (0.435 g, 1.05 mmol) in dioxane/water (4:1, 15 ml) was added a mixture of 2,4-dimethyl-4,5,6,7-tetrahydrooxazolo [5,4-c]pyridine and 2,6-dimethyl-4,5,6,7-tetrahydrooxazolo [5,4-c]pyridine (0.16 g, 1.05 mmol), KI (0.175 g, 1.05 mmol), and Hunig's base (0.2 ml, 2.10 mmol). The reaction mixture was stirred at 70° C. for 15 hours. The reaction mixture was loaded on to a 100 grams C18-reverse phase Biotage column eluting with water/acetonitrile+0.1% TFA (0-30%, 30 min) to afford the product mixture. The enantiomeric forms of titled products Ex-236 and Ex-237 were separated through chiral HPLC using an AD-H column, which were characterized by LC/MS. LC/MS=394 [M+1].

Example 16: Preparation of 7-methoxy-2-(2-(2-methyl-4H-pyrrolo[3,4-d]thiazol-5(6H)-yl)ethyl)-[1,2,4]triazolo[1,5-c]quinazolin-5-amine (Ex-14)

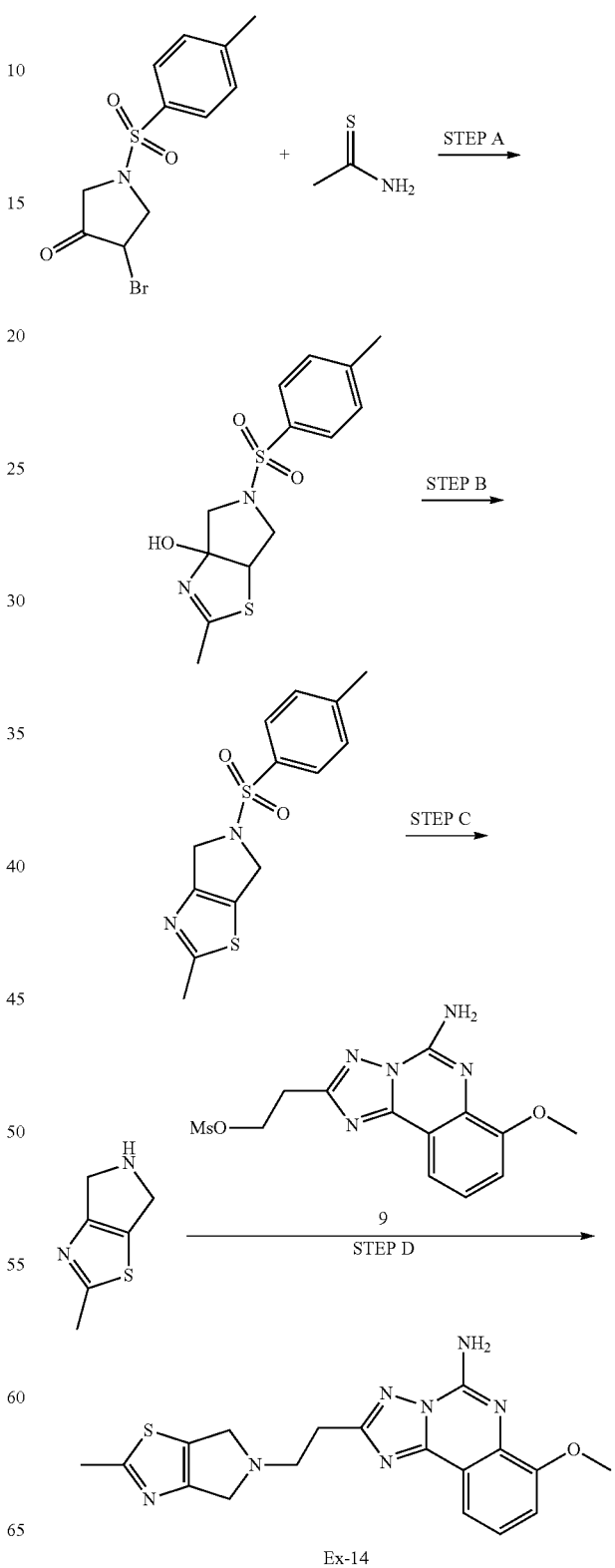

(Step A) 2-methyl-5-tosyl-4,5,6,6a-tetrahydro-3aH-pyrrolo[3,4-d]thiazol-3a-ol To a stirred solution of 4-bromo-1-tosylpyrrolidin-3-one (1 g, 3.14 mmol) in DMF (12.57 ml) was added ethanethioamide (0.236 g, 3.14 mmol) at RT. The reaction mixture was heated to 60° C. for 2 hrs.

After being cooled down to room temperature, sat. $NaHCO_3$ (aq) was added. The aqueous layer was extracted with EtOAc (250 mL). The organic layer was washed with sat. $NaHCO_3$ (aq) and brine, dried over $MgSO_4$, filtered and then concentrated. The crude bright brown solid was used for the next step without further purification.

(Step B) 2-methyl-5-tosyl-5,6-dihydro-4H-pyrrolo[3,4-d]thiazole

To a stirred solution of 2-methyl-5-tosyl-4,5,6,6a-tetrahydro-3aH-pyrrolo[3,4-d]thiazol-3a-ol (982 mg, 3.14 mmol) in CH2Cl2 (13 mL) was added triethylamine (4381 µl, 31.4 mmol) and drop wise Ms-Cl (490 µl, 6.29 mmol) at 0° C. The reaction mixture was stirred at 0° C. for 30 min and warmed to RT. After stirring at RT for 1 hr, the reaction mixture was diluted with DCM and water was added. The organic layer was washed with water and brine solution, dried over $MgSO_4$, filtered and concentrated. The crude product was purified by silica-gel column chromatography (24 g, 10% EtOAc/DCM) to provide the desired product.

(Step C) 2-methyl-5,6-dihydro-4H-pyrrolo[3,4-d]thiazole

To a stirred solution of 2-methyl-5-tosyl-5,6-dihydro-4H-pyrrolo[3,4-d]thiazole (835 mg, 2.84 mmol) in HBr (17 mL, 148 mmol) in water (48%) was added Phenol (267 mg, 2.84 mmol) at room temperature. The reaction mixture was refluxed at 90° C. for 1.2 hrs. After cooled down to room temp, 16 mL water was added and extracted with Et2O (40 mL×2). The organic layer was dried over $MgSO_4$, filtered and concentrated. The aqueous layer was basified by solid NaOH and extracted with DCM. The DCM layer was dried over MgSO4, filtered and concentrated to afford the desired product (oil).

The crude oil was used for the next step without further purification.

(Step D) 7-methoxy-2-(2-(2-methyl-4H-pyrrolo[3,4-d]thiazol-5(6H)-yl)ethyl)-[1,2,4]triazolo[1,5-c]quinazolin-5-amine To a stirred suspension of 2-(5-amino-7-methoxy-[1,2,4]triazolo[1,5-c]quinazolin-2-yl)ethyl methanesulfonate (9) (500 mg, 1.48 mmol) in Dioxane (9.5 mL) and water (2.5 mL) was added 2-methyl-5,6-dihydro-4H-pyrrolo[3,4-d]thiazole (393 mg, 2.22.3 mmol), KI (246 mg, 1.482 mmol) and DIPEA (0.518 mL, 2.96 mmol). The reaction mixture was capped and stirred at 70° C. overnight. After being cooled down to room temperature, sat. aq. NH4Cl was added to reaction mixture and extracted with DCM. The organic layer was dried over $MgSO_4$, filtered and concentrated. The crude product was purified by flash silica gel column chromatography (10% MeOH/DCM) to provide the desired product.

Additional compounds of the invention, presented in Table XXIII, below, were prepared using methods described in Scheme 16 using the appropriate amide in Step A.

TABLE XXIII

| Compound No. | Structure | LC-MS |
|---|---|---|
| Ex-241 | 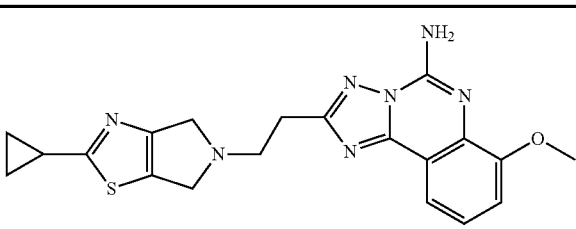<br>2-(2-(2-cyclopropyl-4H-pyrrolo[3,4-d]thiazol-5(6H)-yl)ethyl)-7-methoxy-[1,2,4]triazolo[1,5-c]quinazolin-5-amine | 408 [M + 1] |
| Ex-242 | 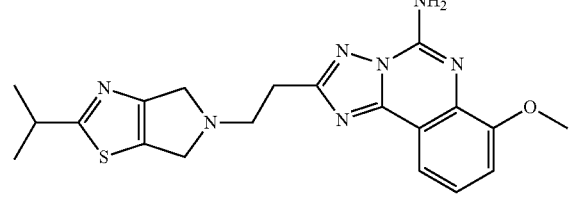<br>2-(2-(2-isopropyl-4H-pyrrolo[3,4-d]thiazol-5(6H)-yl)ethyl)-7-methoxy-[1,2,4]triazolo[1,5-c]quinazolin-5-amine | 410 [M + 1] |

TABLE XXIII-continued

| Compound No. | Structure | LC-MS |
|---|---|---|
| Ex-243 | 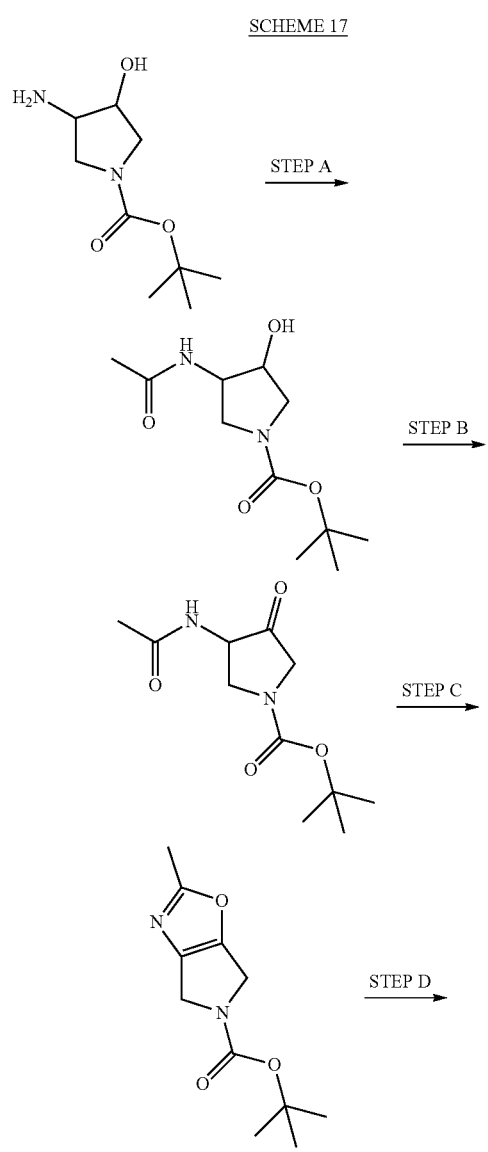  2-(2-(2-ethyl-4H-pyrrolo[3,4-d]thiazol-5(6H)-yl)ethyl)-7-methoxy-[1,2,4]triazolo[1,5-c]quinazolin-5-amine | 396 [M + 1] |

Example 17: Preparation of 7-methoxy-2-(2-(2-methyl-4H-pyrrolo[3,4-d]oxazol-5(6H)-yl)ethyl)-[1,2,4]triazolo[1,5-c]quinazolin-5-amine (Ex-244)

SCHEME 17

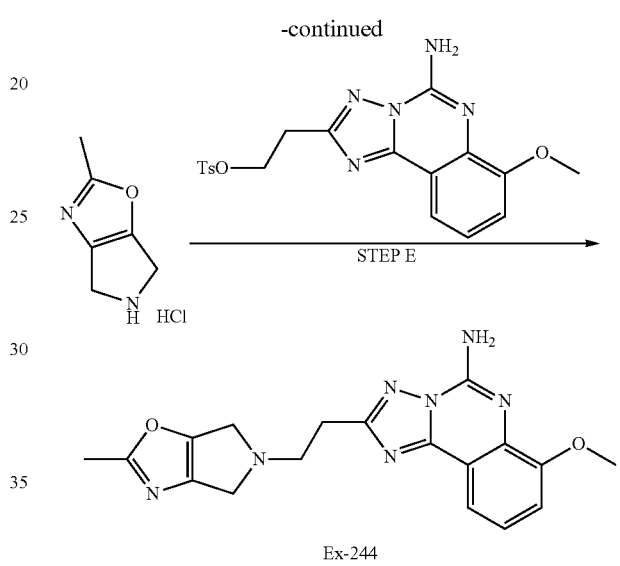

Ex-244

(Step A) tert-butyl 3-acetamido-4-hydroxypyrrolidine-1-carboxylate

To a stirred solution of tert-butyl 3-amino-4-hydroxypyrrolidine-1-carboxylate (5.6 g, 27.7 mmol) in DCM (277 ml) was added TEA (3.86 ml, 27.7 mmol) and acetyl chloride (1.969 ml, 27.7 mmol) drop wise at −20° C. The reaction mixture was stirred at −20° C. for 1.5 hr. The reaction was quenched by addition of 20 mL of MeOH. The reaction mixture was stirred vigorously for 10 min. Sat. $NaHCO_3$ (aq, 400 mL) was added and extracted with 10% MeOH/DCM (×3) and organic layer was dried over $MgSO_4$, filtered and concentrated to give tert-butyl 3-acetamido-4-hydroxypyrrolidine-1-carboxylate. The crude product was used for the next step without further purification.

(Step B) tert-butyl 3-acetamido-4-oxopyrrolidine-1-carboxylate

To a stirred solution of 3-acetamido-4-hydroxypyrrolidine-1-carboxylate (4.5 g, 18.42 mmol) in DCM (184 ml) was added Dess-Martin Periodinane (11.72 g, 27.6 mmol) at RT. The reaction mixture was stirred at RT overnight. The reaction mixture was diluted with DCM and washed with sat. aq. Sodium thiosulfate (×2), and aq. $NaHCO_3$ (×2) and brine. The organic layer was dried over $MgSO_4$, filtered and concentrated. The crude product was purified by silica gel flash column chromatography (100% DCM to 50% EtOAc/DCM) to provide tert-butyl 3-acetamido-4-oxopyrrolidine-1-carboxylate.

(Step C) tert-butyl 2-methyl-4H-pyrrolo[3,4-d]oxazole-5(6H)-carboxylate

To a stirred solution of hexachloroethane (2.57 ml, 22.70 mmol) and triphenylphosphine (7.15 g, 27.2 mmol) in DCM (100 mL) was added triethylamine (10.13 ml, 72.6 mmol) at room temperature. A solution of tert-butyl 3-acetamido-4-oxopyrrolidine-1-carboxylate (2.2 g, 9.08 mmol) in DCM (80 mL) was added drop wise. The reaction mixture was stirred at room temperature for 2 days. Sat. aq. NaHCO$_3$ was added. The reaction mixture was extracted with DCM. The organic layer was dried over MgSO$_4$, filtered and concentrated. The crude product was purified by silica-gel flash column chromatography (40 g, 100% Hex to 1/1 EtOAc/Hex to 100% EtOAc) to provide tert-butyl 2-methyl-4H-pyrrolo[3,4-d]oxazole-5(6H)-carboxylate.

(Step D) 2-methyl-5,6-dihydro-4H-pyrrolo[3,4-d]oxazole

To a round bottom flask of tert-butyl 2-methyl-4H-pyrrolo[3,4-d]oxazole-5(6H)-carboxylate (675 mg, 3.0 mmol) was added 4N HCl (13 mL, 45 mmol) in dioxane at room temperature. The reaction mixture was stirred at room temperature overnight. The solvent was evaporated and the crude product was used for the next step without further purification.

(Step E) 7-methoxy-2-(2-(2-methyl-4H-pyrrolo[3,4-]oxazol-5(6H)-yl)ethyl-[1,2,4]triazolo[1,5-c]quinazolin-5-amine To a stirred suspension of 2-(5-amino-7-methoxy-[1,2,4]triazolo[1,5-c]quinazolin-2-yl)ethyl 4-methylbenzenesulfonate (450 mg, 1.1 mm), which can be prepared using a synthesis scheme similar to Scheme 1, in dioxane (7 mL) and water (0.8 mL) was added DIPEA (0.57 mL, 3.8 mmol) and 2-methyl-5,6-dihydro-4H-pyrrolo[3,4-d]oxazole (262 mg, 1.6 mmol). The reaction mixture was capped and heated to 75° C. overnight. After being cooled down to room temperature, the reaction mixture was diluted with DCM and washed with aq. saturated NaHCO$_3$. The organic layer was dried over MgSO$_4$, filtered and concentrated. The crude product was purified by silica-gel flash column chromatography (40 g, 10% MeOH/DCM) to provide 7-methoxy-2-(2-(2-methyl-4H-pyrrolo[3,4-d]oxazol-5(6H)-yl)ethyl)-[1,2,4]triazolo[1,5-c]quinazolin-5-amine (Ex-244), which was characterized by LC-MS=366 [M+1].

Additional compounds of the invention, presented in Table XXIV, below, were prepared using similar methods to that described in Scheme 17.

TABLE XXIV

| Compound No. | Structure | LCMS |
|---|---|---|
| Ex-245 | 2-(2-(2-cyclopropyl-4H-pyrrolo[3,4-d]oxazol-5(6H)-yl)ethyl)-7-methoxy-[1,2,4]triazolo[1,5-c]quinazolin-5-amine | 392 [M + 1] |

A2a Activity of Compounds of the Invention

Binding affinities of compounds of the invention for the human A2a receptor were determined in a competition binding assay using Scintillation Proximity technology. Thus, 0.3 μg of membranes from HEK293 cells expressing the human A2a receptor were incubated with a compound of the invention at concentrations ranging from 3000 nM to 0.15 nM in a reaction mixture containing also 0.5 nM of a tritiated form of 5-amino-7-[2-phenethyl]-2-(furan-2-yl)-7H-pyrazolo[4,3-e][1,2,4]triazolo[1,5-c]pyrimidine (the tritiated compound) and 100 μg of wheat germ agglutin-coated yttrium silicate SPA beads for one hour at room temperature with agitation. The beads were then allowed to settle to the bottom of the wells for 1 hr, after which the membrane-associated radioactivity was determined by scintillation counting in a TopCount microplate reader. Ki values were determined using the Cheng-Prusoff equation.

Summary of Materials and Methods Used in A2a Activity Determination:

Materials

HEK293 cells expressing the human, rat, dog or monkey adenosine 2a receptor (Purchased from Perkin-Elmer # RBHA2AM400UA).

The Tritiated compound was prepared in-house by MRL Radiochemistry according to published methods.

Wheat germ agglutinin-coated yttrium silicate SPA beads (GE Healthcare#RPNQ0023). Dilute to 25 mg/ml in assay buffer.

Assay Buffer was prepared in house: Dulbecco's calcium and magnesium free phosphate buffered saline+10 mM MgCl$_2$ Adenosine deaminase from calf intestine, 10 mg/2 ml (Roche) 10 102 105 001).

DMSO

A2a antagonist standard (9-chloro-1-(2-furanyl)-[1,2,4]triazolo1,5-c]quinazolin-5-amine from Tocris Bioscience)

Compound Dilution

Make eight 1:3 serial dilutions in 100% DMSO from a 3 mM compound stock

Transfer 50 nl of compound into a 384-well OptiPlate (Perkin Elmer).

Typically, final concentrations of compound used in the assay ranged from 3000 nM to 0.152 nM.

Radioisotope

Dilute a solution of the Tritiated compound to 1.25 nM in assay buffer. This is a 2.5× solution. The final concentration in the assay is 0.5 nM. Calculate the concentration by counting two 5 µl aliquots.

Membrane Preparation

Use 0.25 ug of membrane/well. Dilute membranes to 9.7 µg/ml in assay buffer. Treat with 20 ug/ml adenosine deaminase (ADA) for 15 minutes at room temperature to degrade endogenous adenosine.

Membrane-Bead Mixture

Use 100 µg/well wheat germ agglutinin-coated yttrium silicate SPA beads.

Mix ADA-treated membranes and SPA beads together for 30 min prior to assay.

Assay Assembly

To the Perkin-Elmer Optiplate-384 containing the compound titration add 20 µl of 2.5× solution of the Tritiated compound and 30 µl of the membrane-bead mixture. Incubate for one hour at room temperature with agitation.

Include total binding (assay buffer+1% DMSO) and non-specific binding (CGS15943, 1 µM) wells.

Counting

Allow the beads to settle for one hour.

Count in TopCount.

Calculations

A curve fitting program (i.e., Prism, Activity Base, Chemcart) is used to determine the EC50. The Ki value is calculated using the Cheng-Prusoff equation:

$$K i=EC50/(1+(\text{radioligand concentration}/Kd)).$$

Using the foregoing assay method, the following results were obtained using various of the compounds of the invention described herein. Each example compound tested is reported in the following format: Example number: A2a EC50 reported in nM. Thus, for example, the compound Ex-1 was determined to have an EC50 using the above-described assay, of 4.0 nM, and is accordingly reported as "Ex-1: A2a=4.0":

Ex-1: A2a=4.0; Ex-2: A2a=2.9; Ex-3: A2a=3.4; Ex-4: A2a=4.6; Ex-5: A2a=4.7; Ex-6: A2a=5.9; Ex-7: A2a=1.4; Ex-8: A2a=2.2; Ex-9: A2a=2.1; Ex-10: A2a=1.2; Ex-11: A2a=2.7; Ex-12: A2a=2.0; Ex-13: A2a=2.2; Ex-14: A2a=1.5; Ex-15: A2a=2.2; Ex-16: A2a=2.3; Ex-17: A2a=9.6; Ex-18: A2a=13.3; Ex-19: A2a=7.6; Ex-20: A2a=12.8; Ex-21: A2a=31.2; Ex-22: A2a=6.7; Ex-23: A2a=4.4; Ex-23: A2a=6.6; Ex-24: A2a=11.1; Ex-25: A2a=0.9; Ex-26: A2a=0.5; Ex-27: A2a=1.6; Ex-28: A2a=2.2; Ex-29: A2a=1.7; Ex-30: A2a=1.1; Ex-31: A2a=1.3; Ex-32: A2a=1.4; Ex-33: A2a=4.2; Ex-34: A2a=1.7; Ex-35: A2a=2,3; Ex-36: A2a=6.7; Ex-37: A2a=6.4; Ex-38: A2a=2.0; Ex-39: A2a=1.8; Ex-40: A2a=1.1; Ex-41: A2a=2.6; Ex-42: A2a=1.4; Ex-43: A2a=8.4; Ex-44: A2a=4.2; Ex-45: A2a=4.3; Ex-46: A2a=18.0; Ex-48: A2a=4.6; Ex-49: A2a=5.4; Ex-50: A2a=1.5; Ex-51: A2a=2.9; Ex-52: A2a=8.8; Ex-53: A2a=2.4; Ex-54: A2a=4.0; Ex-55: A2a=1.8; Ex-56: A2a=3.4; Ex-57: A2a=1.7; Ex-58: A2a=0.9; Ex-59: A2a=9.6; Ex-60: A2a=2.3; Ex-61: A2a=2.5; Ex-62: A2a=6.2; Ex-63: A2a=5.8; Ex-64: A2a=6.9; Ex-65: A2a=13.6; Ex-66: A2a=16.6; Ex-68: A2a=7.0; Ex-69: A2a=5.2; Ex-70: A2a=6.8; Ex-71: A2a=2.9; Ex-72: A2a=5.0; Ex-73: A2a=3.0; Ex-74: A2a=4.3; Ex-76: A2a=3.7; Ex-77: A2a=36.2; Ex-78: A2a=13.8; Ex-79: A2a=22.3; Ex-80: A2a=12.0; Ex-82: A2a=24.7; Ex-83: A2a=15.9; Ex-84: A2a=6.3; Ex-85: A2a=22.2; Ex-86: A2a=6.7; Ex-87: A2a=19.1; Ex-88: A2a=42.3; Ex-89: A2a=47.7; Ex-90: A2a=27.9; Ex-91: A2a=26.1; Ex-92: A2a=73.7; Ex-93: A2a=37.5; Ex-94: A2a=27.3; Ex-95: A2a=16.5; Ex-96: A2a=56.2; Ex-97: A2a=238.4; Ex-98: A2a=19.0; Ex-99: A2a=111.7; Ex-100: A2a=31.2; Ex-102: A2a=55.2; Ex-103: A2a=8.3; Ex-104: A2a=10.1; Ex-104: A2a=14.3; Ex-106: A2a=19.5; Ex-107: A2a=6.9; Ex-108: A2a=17.9; Ex-109: A2a=12.2; Ex-110: A2a=39.9; Ex-111: A2a=11.9; Ex-112: A2a=4.9; Ex-113: A2a=22.8; Ex-114: A2a=4.3; Ex-115: A2a=21.6; Ex-117: A2a=5.9; Ex-118: A2a.=5.4; Ex-119: A2a=2.1; Ex-120: A2a=1.5; Ex-121: A2a=0.8; Ex-122: A2a=6.0; Ex-123: A2a=5.6; Ex-125: A2a=27.3; Ex-126: A2a=31.6; Ex-127: A2a=8.5; Ex-128: A2a=2.0; Ex-129: A2a=40.8; Ex-130: A2a=20.5; Ex-131: A2a=16.0; Ex-132: A2a=7.9; Ex-133: A2a=27.8; Ex-134: A2a=6.7; Ex-135: A2a=11.8; Ex-136: A2a=191.4; Ex-137: A2a=16.1; Ex-138: A2a=145.6; Ex-139: A2a=109.5; Ex-140: A2a=103.8; Ex-141: A2a=149.4; Ex-142: A2a=350.5; Ex-143: A2a=74.4; Ex-144: A2a=149.0; Ex-145: A2a=47.8; Ex-146: A2a=29.9; Ex-148: A2a=7.2; Ex-149: A2a=17.5; Ex-150: A2a=27.6; Ex-151: A2a=48.2; Ex-152: A2a=27.8; Ex-153: A2a=283.6; Ex-154: A2a=2.3; Ex-155: A2a=2.2; Ex-156: A2a=6.0; Ex-157: A2a=1.6; Ex-158: A2a=11.0; Ex-160: A2a=1.5; Ex-161: A2a=2.1; Ex-162: A2a=2.7; Ex-163: A2a=2.7; Ex-164: A2a=8.6; Ex-165: A2a=4.4; Ex-166: A2a=4.5; Ex-167: A2a=7.6; Ex-168: A2a=4.3; Ex-172: A2a=6.1; Ex-173: A2a=9.1; Ex-175: A2a=4.6; Ex-177: A2a=17.0; Ex-179: A2a=6.1; Ex-180: A2a=9; Ex-182: A2a=2.8; Ex-184: A2a=2.9; Ex-185: A2a=11.2; Ex-186: A2a=3.9; Ex-187: A2a=2.9; Ex-194: A2a=8.8; Ex-195: A2a=16.6; Ex-196: A2a=274.0; Ex-197: A2a=611.5; Ex-198: A2a=207.3; Ex-199: A2a=199.4; Ex-200: A2a=35.5; Ex-201: A2a=21.7; Ex-202: A2a=147.4; Lx-203: A2a=88.3; Ex-204: A2a=40.7; Ex-205: A2a=10.9; Ex-211: A2a=3.0; Ex-212: A2a=6.1; Ex-214: A2a=29; Ex-215: A2a=5.7; Ex-216: A2a=3.0; Ex-221: A2a=3.9; Ex-227: A2a=7.7; Ex-228: A2a=7.8; Ex-229: A2a=14.8; Ex-230: A2a=5.7; Ex-235: A2a=2.8; Ex-236: A2a=1.4; Ex-237: A2a=3.5; Ex-241: A2a=7.3; Ex-242: A2a=0.1; Ex-243: A2a=1.3; Ex-244: A2a=0.3; Ex-245: A2a=1.0; Ex-246: A2a=5.4; Ex-247: A2a=0.2; Ex-248: A2a=1.0.

What is claimed is:

1. A compound of Formula GI:

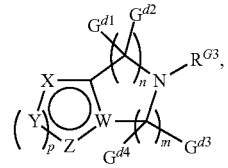

Formula GI or a pharmaceutically acceptable salt thereof, wherein:

W is nitrogen or carbon;

m is 1, 2, 3, or 4; n is an integer of from 0 to 4, wherein the sum of n+m is at least 2 up to 4, and wherein, when W is N, m is at least 2;

$G^{d1}$ through $G^{d4}$ are independently hydrogen or a $C_{1-6}$-alkyl;

p is 1 or 2, wherein, p is not elected to be 1 when the values of m+n=2;

X, Y, and Z together with W and the carbon to which X and W are bonded form a 5 to 6 member aromatic or heteroaromatic moiety, and are independently:

(a) $(R^{G1})C=$, wherein $R^{G1}$ is:
  (i) hydrogen;
  (ii) $C_{1-8}$-alkyl, optionally substituted with one or more halogen atoms;
  (iii) —C(O)—$C_{1-8}$-alkyl;
  (iv) —CN;
  (v) —S—$C_{1-8}$-alkyl;
  (vi) —O—$C_{1-6}$-alkyl;
  (vii) —$(CH_2)_{q1}$—$(C=O)_{q2}$—$N(R^2)_2$, where $R^2$ is independently for each occurrence hydrogen, $C_{1-6}$-alkyl or heteroaryl, and wherein q1 is 0 or 1 and q2 is 0 or 1;
  (viii) —C(O)O—$C_{1-8}$-alkyl;
  (ix) halogen;
  (x) a mono- or polycyclic heterocyclic moiety comprising up to 10 carbon atoms and one or more heteroatoms selected from N, S, or O, optionally substituted with one or more $C_{1-6}$-alkyl, morpholino, phenyl (optionally substituted with halogen), heteroaryl or halogen;
  (xi) aryl, which is optionally substituted with one or more substituents which are: (1) halogen; or (2) $C_{1-6}$-alkyl which is optionally substituted with one or more halogen atoms;
  (xii) —NH—C(O)—$R^3$, wherein $R^3$ is $C_{1-6}$-alkyl or heteroaryl; or,
  (xiii) heteroaryl, which is optionally substituted with: (ai) a $C_{1-6}$-alkyl moiety, which alkyl moiety is optionally substituted with one or more halogen atoms; or (bi) amino; or (b) >$NR^{G2}$, wherein $R^{G2}$ is: (i) hydrogen; (ii) $C_{1-8}$-alkyl; or (iii) an aromatic moiety of up to 10 carbon atoms;

(c) N=;
(d) —O—; or,
(e) —S—; and, $R^{G3}$ is a moiety of the structure:

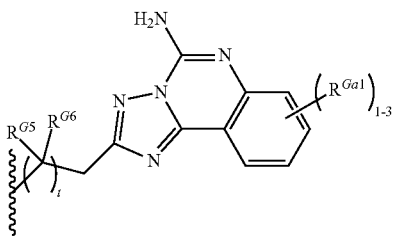

wherein:

t is 0, 1 or 2;

$R^{G5}$ and $R^{G6}$ are independently for each occurrence:
(a) H;
(b) $C_{1-10}$-alkyl, optionally substituted with one or more fluorine atoms; or, (c) $R^{G5}$ and $R^{G6}$ taken together form a carbonyl moiety (C=O), with the proviso that if t=2, $R^{G5}$ and $R^{G6}$ are not selected to provide two adjacent carbonyl moieties; and $R^{Ga1}$ is 1 to 3 substituents replacing an H on a ring carbon atom that are independently for each occurrence:
(a) $C_{1-4}$-alkoxy, wherein the alkyl portion of the alkoxy moiety is optionally substituted with one or more halogen;
(b) $C_{1-8}$-alkyl, optionally substituted with one or more halogen atoms;
(c) halogen;
(d) —CN; or
(e) —$N(R^{G4})_2$, wherein at least one of $R^{G4}$ is $C_{1-6}$alkyl and the other is H or $C_{1-6}$-alkyl.

2. A compound of claim 1 or a pharmaceutically acceptable salt thereof wherein $R^{G3}$ is a moiety of the structure:

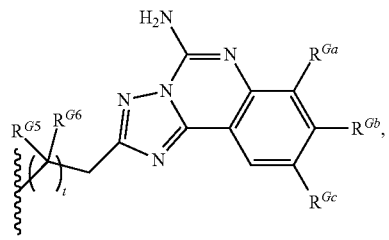

wherein:

t is 0, 1 or 2;

$R^{G5}$ and $R^{G6}$ are independently for each occurrence:
(a) H;
(b) $C_{1-10}$-alkyl, optionally substituted with one or more fluorine atoms; or
(c) $R^{G5}$ and $R^{G6}$ taken together form a carbonyl moiety (C=O), with the proviso that if t=2, $R^{G5}$ and $R^{G6}$ are not selected to provide two adjacent carbonyl moieties; and, $R^{Ga}$, $R^{Gb}$, and $R^{Gc}$ are independently:
(a) H;
(b) $C_{1-4}$-alkoxy, wherein the alkyl portion of the alkoxy moiety is optionally substituted with one or more halogen;
(c) $C_{1-8}$alkyl, optionally substituted with one or more halogen atoms;
(d) a halogen which is: F; or Cl;
(e) —$N(R^{G4})_2$, wherein at least one of $R^{G4}$ is $C_{1-6}$-alkyl and the other is H or $C_{1-6}$-alkyl; or,
(f) —CN;

with the proviso that at least one of $R^{Ga}$, $R^{Gb}$, or $R^{Gc}$ is H, and at least one of $R^{Ga}$, $R^{Gb}$, or $R^{Gc}$ is not H.

3. A compound of claim 1 or a pharmaceutically acceptable salt thereof wherein, when X, Y, or Z is —$C(R^{G1})=$, and $R^{G1}$ is selected to be a halogen substituted $C_{1-6}$-alkyl moiety, the halogen is F or Cl.

4. A compound of claim 1 or a pharmaceutically acceptable salt thereof wherein at least one of X, Y, or Z is —N=, and at least one of X, Y, or Z is —O— or —S—.

5. A compound of claim 1 or a pharmaceutically acceptable salt thereof having the structure of Formula GII:

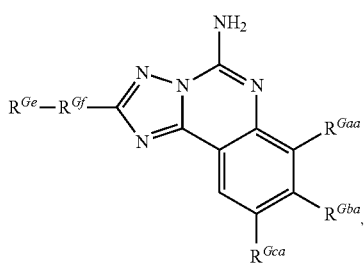

Formula GII or a pharmaceutically acceptable salt thereof, wherein:
$R^{Gaa}$, $R^{Gba}$, and $R^{Gca}$ are independently for each occurrence:
- (a) H;
- (b) $C_{1-6}$-alkyl;
- (c) $C_{1-4}$-alkoxy, optionally substituted with one or more fluorine atoms;
- (d) F;
- (e) Cl;
- (f) Br;
- (g) —CN; or,
- (h) —N($R^{G9}$)$_2$, wherein $R^{G9}$ is independently for each occurrence $C_{1-6}$-alkyl or H; and wherein $R^{Gaa}$, $R^{Gba}$, and $R^{Gca}$ are selected such that at least one of $R^{Gaa}$, $R^{Gba}$, and $R^{Gca}$ is H, and at least one of $R^{Gaa}$, $G^{Gba}$, and $R^{Gca}$ is not H;

$R^{Gf}$ is:
- (a) —CH$_2$—;
- (b) -ethyl-, which is optionally substituted with one or more: $C_{1-6}$-alkyl, which substituent is optionally substituted with one or more fluorine atoms;
- (c) -propyl-; or,
- (d) —C(O)—CH$_2$—; and, $R^{Ge}$ is a heteroaryl bicyclic moiety comprising up to 12 ring atoms, of the structure:

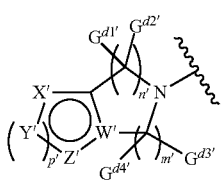

wherein:
W' is nitrogen or carbon;
m' is 1, 2, 3, or 4;
n' is an integer of from 0 to 4, wherein the sum of n'+m' is at least 2 up to 4, and wherein, when W' is N, m' is at least 2;
p' is 1 or 2; wherein, p' is not elected to be 1 when the values of m'+n'=2;
$G^{d1'}$ through $G^{d4'}$ are independently H or $C_{1-6}$-alkyl;
X', Y', and Z' together with W' and the carbon to which X' and W' are bonded form a 5 to 6 member aromatic or heteroaromatic moiety, and are independently:
- (a) —($R^{G1'}$)C=, wherein $R^{G1'}$ is:
  - (i) H;
  - (ii) $C_{1-8}$-alkyl, optionally substituted with one or more halogen atoms;
  - (iii) —C(O)—$C_{1-8}$-alkyl;
  - (iv) —CN;
  - (v) —S—$C_{1-8}$-alkyl;
  - (vi) —O—$C_{1-6}$-alkyl;
  - (vii) —(CH$_2$)$_q$—C(O)—N($R^{2'}$)$_2$, wherein $R^{2'}$ is independently for each occurrence H, $C_{1-4}$-alkyl or pyridyl, and wherein q is 0 or 1;
  - (viii) —C(O)O—$C_{1-8}$-alkyl;
  - (ix) halogen;
  - (x) morpholine, optionally substituted on any carbon atom thereof by one or more $C_{1-6}$-alkyl moieties;
  - (xi) piperazine, wherein the 4-N nitrogen is bonded to a substituent which is: (ai) H; (aii) $C_{1-6}$-alkyl; (aiii) morpholino; (aiv) phenyl, optionally substituted with a halogen; (av) halogen; or (avi) heteroaryl;
  - (xii) piperidinyl, optionally substituted by $C_{1-6}$-alkyl or a morpholine moiety;
  - (xiii) pyrrolidine, optionally substituted with one or more halogen atoms;
  - (xiv) phenyl, which is optionally substituted with one or more halogen atoms or $C_{1-6}$-alkyl; or
  - (xv) —NH—C(O)—$R^{3'}$, wherein $R^{3'}$ is $C_{1-4}$-alkyl or pyridinyl;
  - (xvi) heteroaryl, which is optionally substituted with CF$_3$, $C_{1-6}$-alkyl or amino; or
  - (xvii) —N($R^{4'}$)$_2$, wherein $R^{4'}$ is independently for each occurrence H or $C_{1-6}$-alkyl;
- (b) >N$R^{G2'}$, wherein $R^{G2'}$ is: (i) H; (ii) $C_{1-8}$alkyl; or (iii) an aromatic moiety of up to 10 carbon atoms;
- (c) —N=;
- (d) —O—; or
- (e) —S—.

6. A compound of claim 5, or a pharmaceutically acceptable salt thereof, wherein $R^{Ge}$ is a moiety of Formula $R^{GeA}$:

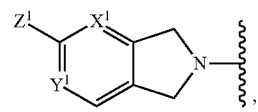

Formula $R^{GeA}$ and wherein the compound is selected from a group of compounds where $X^1$, $Y^1$ and $Z^1$ are as defined in Table CA:

TABLE CA

| $X^1$ | $Y^1$ | $Z^1$ |
|---|---|---|
| N | C(H) | Cl |
| N | N | CF$_3$ |
| N | N | H |
| N | N | CH$_3$ |
| C(H) | C(H) | H |
| C(H) | C(H) | CF$_3$ |
| C(H) | C(H) | F |
| N | C(H) | H |
| C(F) | C(H) | H |
| C(F) | C(F) | H |

7. A compound of claim 5, or a pharmaceutically acceptable salt thereof, wherein $R^{Ge}$ is a moiety of Formula $R^{GeB}$:

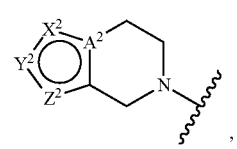

Formula $R^{GeB}$ and wherein the compound is selected from a group of compounds where A², X², Y² and Z² are as defined in Table CB:

TABLE CB

| X² | Y² | Z² | A² |
|---|---|---|---|
| —C(—S—CH₃)= | —N= | —N= | —N< |
| —C(—C(O)—NH—Propyl)= | —N= | —N= | —N< |
| —C(Br)= | —N= | —N= | —N< |
| —C(C(O)—O-ethyl)= | —N= | —N= | —N< |
| >N(cyclopropyl) | —C(H)= | —N= | >C= |
| —C(isopropyl)= | —C(H)= | —N= | —N< |
| —C(—C(O)-cyclopropyl)= | —N= | —C(H)= | —N< |
| —N= | —N= | —C(—CF₃)= | —N< |
| —N= | —N= | —C(cyclopropyl)= | —N< |
| —C(ethyl)= | —C(H)= | —N= | —N< |
| —N= | —N(H)— | —C(—CF₃)= | >C= |
| —C(—CF₃)= | —N= | —N= | —N< |
| —C(ethyl)= | —N= | —N= | —N< |
| —N(CH₃)— | —C(—CF₃)= | —N= | >C= |
| —N(H)— | —C(H)= | —N= | >C= |
| —N(H)— | —C(CH₃)= | —N= | >C= |
| —N(H)— | —C(CF₃)= | —N= | >C= |
| —C(isopropyl)= | —N(H)— | —N= | >C= |
| —N= | —C(H)= | —C(CH₃)= | —N< |
| —C(—CF₃)= | —N(H)— | —N= | >C= |
| —C(H)= | —N= | —C(CF₃)= | —N< |
| —C(ethyl)= | —N= | —N= | —N< |

8. A compound of claim 5, or a pharmaceutically acceptable salt thereof, wherein $R^{Ge}$ is a moiety of Formula $R^{GeC}$:

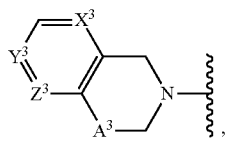

Formula $R^{GeC}$ and wherein the compound is selected from a group of compounds where X³, Y³, Z³ and A³ are as defined in Table CC:

TABLE CC

| X³ | Y³ | Z³ | A³ |
|---|---|---|---|
| N | C(Br) | C(H) | CH₂ |
| C(H) | C(F) | C(H) | CH₂ |
| N | C(H) | C(H) | CH₂ |
| C(H) | C(—OCH₃) | C(H) | CH₂ |
| N | N | C(H) | CH₂ |
| N | C(H) | N | CH₂ |
| C(H) | C(H) | C(H) | C(CH₃)₂ |
| N | C(H) | C(—Br) | CH₂ |
| N | C(H) | C—N(CH₃)(CH₃) | CH₂ |
| N | C(H) | C—N(piperazine-N-CH₃) | CH₂ |
| N | C(H) | C—N(3,3-difluoropyrrolidine) | CH₂ |

9. A compound of claim 5, or a pharmaceutically acceptable salt thereof, wherein $R^{Ge}$ is a moiety of Formula $R^{GeD}$:

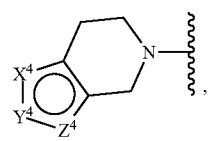

Formula $R^{GeD}$ and wherein the compound is selected from a group of compounds where X⁴, Y⁴ and Z⁴ are as defined in Table CD:

TABLE CD

| X⁴ | Y⁴ | Z⁴ |
|---|---|---|
| —N= | —O— | —C(CF₃)= |
| —C(—CN)= | —C(-cyclopropyl)= | —S— |
| —S— | —C(CH₃)= | —N= |
| —S— | —C(CF₃)= | —N= |
| —O— | —C(CH₃)= | —N= |
| —N= | —C(CH₃)= | —O— |
| —N= | —C(CH₃)= | —S— |
| —N= | —C(-isopropyl)= | —S— |
| —N= | —C(-isopropyl)= | —O— |
| —O— | —N= | —C(H)= |
| —S— | —C(H)= | —C(H)= |
| —N= | —C(H)= | —S— |
| —S— | —C(H)= | —N= |
| —N= | —C(H)= | —O— |
| —N= | —C(CHF₂)= | —O— |
| —N= | —C(CH₂OCH₃)= | —O— |

10. A compound of claim 5, or a pharmaceutically acceptable salt thereof, wherein $R^{Ge}$ is the following moiety:

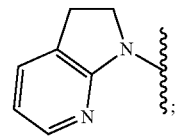

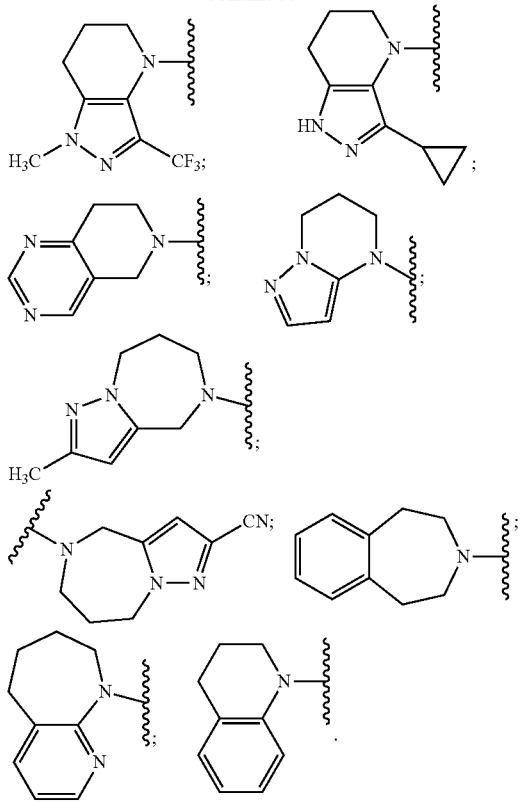

11. A compound, or a pharmaceutically acceptable salt thereof, claim 5 wherein $R^{Gf}$ is —CH(CH$_3$)—CH$_2$—; —CH$_2$—CH$_2$—; or —CH$_2$—.

12. A compound which is:

7-methoxy-2-(2-(3-(methylthio)-5,6-dihydro-[1,2,4]triazolo[4,3-a]pyrazin-7(8H)-yl)ethyl)-[1,2,4]triazolo[1,5-c]quinazolin-5-amine;

7-(2-(5-amino-7-methoxy-[1,2,4]triazolo[1,5-c]quinazolin-2-yl)ethyl)-N-tert-butyl-5,6,7,8-tetrahydro-[1,2,4]triazolo[4,3-a]pyrazine-3-carboxamide;

2-(2-(3-bromo-5,6-dihydro-[1,2,4]triazolo[4,3-a]pyrazin-7(8H)-yl)ethyl)-7-methoxy-[1,2,4]triazolo[1,5-c]quinazolin-5-amine;

ethyl 7-(2-(5-amino-7-methoxy-[1,2,4]triazolo[1,5-c]quinazolin-2-yl)ethyl)-5,6,7,8-tetrahydro-[1,2,4]triazolo[4,3-a]pyrazine-3-carboxylate;

2-(2-(2-chloro-5H-pyrrolo[3,4-b]pyridin-6(7H)-yl)ethyl)-7-methoxy-[1,2,4]triazolo[1,5-c]quinazolin-5-amine;

2-(2-(4-bromo-5,6-dihydro-1,7-naphthyridin-7(8H)-yl)ethyl)-7-methoxy-[1,2,4]triazolo[1,5-c]quinazolin-5-amine;

2-(2-(1-cyclopropyl-6,7-dihydro-1H-pyrazolo[4,3-c]pyridin-5(4H)-yl)ethyl)-7-methoxy-[1,2,4]triazolo[1,5-c]quinazolin-5-amine;

2-(2-(3-isopropyl-5,6-dihydroimidazo[1,5-a]pyrazin-7(8H)-yl)ethyl)-7-methoxy-[1,2,4]triazolo[1,5-c]quinazolin-5-amine;

7-methoxy-2-(2-(3-(trifluoromethyl)-6,7-dihydroisoxazolo[4,3-c]pyridin-5(4H)-yl)ethyl)-[1,2,4]triazolo[1,5-c]quinazolin-5-amine;

(7-(2-(5-amino-7-methoxy-[1,2,4]triazolo[1,5-c]quinazolin-2-yl)ethyl)-5,6,7,8-tetrahydroimidazo[1,2-a]pyrazin-2-yl)(cyclopropyl)methanone;

7-methoxy-2-(2-(2-(trifluoromethyl)-5,6-dihydro-[1,2,4]triazolo[1,5-a]pyrazin-7(8H)-yl)ethyl)-[1,2,4]triazolo[1,5-c]quinazolin-5-amine;

2-(2-(2-cyclopropyl-5,6-dihydro-[1,2,4]triazolo[1,5-a]pyrazin-7(8H)-yl)ethyl)-7-methoxy-[1,2,4]triazolo[1,5-c]quinazolin-5-amine;

2-(2-(3-ethyl-5,6-dihydroimidazo[1,5-a]pyrazin-7(8H)-yl)ethyl)-7-methoxy-[1,2,4]triazolo[1,5-c]quinazolin-5-amine;

6-(2-(5-amino-7-methoxy-[1,2,4]triazolo[1,5-c]quinazolin-2-yl)ethyl)-2-cyclopropyl-4,5,6,7-tetrahydrothieno[2,3-c]pyridine-3-carbonitrile;

7-methoxy-2-(2-(2-(trifluoromethyl)-6,7-dihydro-3H-imidazo[4,5-c]pyridin-5(4H)-yl)ethyl)-[1,2,4]triazolo[1,5-c]quinazolin-5-amine;

7-methoxy-2-(2-(3-(trifluoromethyl)-5,6-dihydro-[1,2,4]triazolo[4,3-a]pyrazin-7(8H)-yl)ethyl)-[1,2,4]triazolo[1,5-c]quinazolin-5-amine;

7-methoxy-2-(2-(2-(trifluoromethyl)-5H-pyrrolo[3,4-d]pyrimidin-6(7H)-yl)ethyl)-[1,2,4]triazolo[1,5-c]quinazolin-5-amine;

2-(2-(5H-pyrrolo[3,4-d]pyrimidin-6(7H)-yl)ethyl)-7-methoxy-[1,2,4]triazolo[1,5-c]quinazolin-5-amine;

2-(2-(7,8-dihydro-5H-pyrido[2,3-b]azepin-9(6H)-yl)ethyl)-7-methoxy-[1,2,4]triazolo[1,5-c]quinazolin-5-amine;

2-(2-(2,3-dihydro-1H-pyrrolo[2,3-b]pyridin-1-yl)ethyl)-7-methoxy-[1,2,4]triazolo[1,5-c]quinazolin-5-amine;

2-(2-(3-ethyl-5,6-dihydro-[1,2,4]triazolo[4,3-a]pyrazin-7(8H)-yl)ethyl)-7-methoxy-[1,2,4]triazolo[1,5-c]quinazolin-5-amine;

7-methoxy-2-(2-(2-methyl-5H-pyrrolo[3,4-d]pyrimidin-6(7H)-yl)ethyl)-[1,2,4]triazolo[1,5-c]quinazolin-5-amine;

2-(2-(isoindolin-2-yl)ethyl)-7-methoxy-[1,2,4]triazolo[1,5-c]quinazolin-5-amine;

7-methoxy-2-(2-(2-methyl-6,7-dihydrothiazolo[4,5-c]pyridin-5(4H)-yl)ethyl)-[1,2,4]triazolo[1,5-c]quinazolin-5-amine;

7-methoxy-2-(2-(2-(trifluoromethyl)-6,7-dihydrothiazolo[4,5-c]pyridin-5(4H)-yl)ethyl)-[1,2,4]triazolo[1,5-c]quinazolin-5-amine;

7-methoxy-2-(2-(2-methyl-6,7-dihydrooxazolo[4,5-c]pyridin-5(4H)-yl)ethyl)-[1,2,4]triazolo[1,5-c]quinazolin-5-amine;

7-methoxy-2-(2-(2-methyl-6,7-dihydrooxazolo[5,4-c]pyridin-5(4H)-yl)ethyl)-[1,2,4]triazolo[1,5-c]quinazolin-5-amine;

7-methoxy-2-(2-(2-methyl-6,7-dihydrothiazolo[5,4-c]pyridin-5(4H)-yl)ethyl)-[1,2,4]triazolo[1,5-c]quinazolin-5-amine;

2-(2-(2-cyclopropyl-6,7-dihydrothiazolo[5,4-c]pyridin-5(4H)-yl)ethyl)-7-methoxy-[1,2,4]triazolo[1,5-c]quinazolin-5-amine;

2-(2-(2-cyclopropyl-6,7-dihydrooxazolo[5,4-c]pyridin-5(4H)-yl)ethyl)-7-methoxy-[1,2,4]triazolo[1,5-c]quinazolin-5-amine;

7-methoxy-2-(2-(1-methyl-3-(trifluoromethyl)-6,7-dihydro-1H-pyrazolo[4,3-c]pyridin-5(4H)-yl)ethyl)-[1,2,4]triazolo[1,5-c]quinazolin-5-amine;

2-(2-(6,7-dihydroisoxazolo[4,5-c]pyridin-5(4H)-yl)ethyl)-7-methoxy-[1,2,4]triazolo[1,5-c]quinazolin-5-amine;

2-(2-(6,7-dihydro-1H-pyrazolo[4,3-c]pyridin-5(4H)-yl)ethyl)-7-methoxy-[1,2,4]triazolo[1,5-c]quinazolin-5-amine;

7-methoxy-2-(2-(3-methyl-6,7-dihydro-1H-pyrazolo[4,3-c]pyridin-5(4H)-yl)ethyl)-[1,2,4]triazolo[1,5-c]quinazolin-5-amine;

7-methoxy-2-(2-(3-(trifluoromethyl)-6,7-dihydro-1H-pyrazolo[4,3-c]pyridin-5(4H)-yl)ethyl)-[1,2,4]triazolo[1,5-c]quinazolin-5-amine;

2-(2-(6,7-dihydrothieno[3,2-c]pyridin-5(4H)-yl)ethyl)-7-methoxy-[1,2,4]triazolo[1,5-c]quinazolin-5-amine;

2-(2-(3-cyclopropyl-4,5-dihydro-1H-pyrazolo[3,4-c]pyridin-6(7H)-yl)ethyl)-7-methoxy-[1,2,4]triazolo[1,5-c]quinazolin-5-amine;

7-methoxy-2-(2-(2-methyl-6,7-dihydropyrazolo[1,5-a]pyrazin-5(4H)-yl)ethyl)-[1,2,4]triazolo[1,5-c]quinazolin-5-amine;

7-methoxy-2-(2-(3-(trifluoromethyl)-4,5-dihydro-1H-pyrazolo[3,4-c]pyridin-6(7H)-yl)ethyl)-[1,2,4]triazolo[1,5-c]quinazolin-5-amine;

7-methoxy-2-(2-(1-methyl-3-(trifluoromethyl)-6,7-dihydro-1H-pyrazolo[4,3-b]pyridin-4(5H)-yl)ethyl)-[1,2,4]triazolo[1,5-c]quinazolin-5-amine;

2-(2-(6-fluoro-3,4-dihydroisoquinolin-2(1H)-yl)ethyl)-7-methoxy-[1,2,4]triazolo[1,5-c]quinazolin-5-amine;

2-(2-(5,6-dihydro-1,7-naphthyridin-7(8H)-yl)ethyl)-7-methoxy-[1,2,4]triazolo[1,5-c]quinazolin-5-amine;

7-methoxy-2-(2-(5-(trifluoromethyl)isoindolin-2-yl)ethyl)-[1,2,4]triazolo[1,5-c]quinazolin-5-amine;

2-(2-(5-fluoroisoindolin-2-yl)ethyl)-7-methoxy-[1,2,4]triazolo[1,5-c]quinazolin-5-amine;

2-(2-(5H-pyrrolo[3,4-b]pyridin-6(7H)-yl)ethyl)-7-methoxy-[1,2,4]triazolo[1,5-c]quinazolin-5-amine;

2-(2-(3-cyclopropyl-6,7-dihydro-1H-pyrazolo[4,3-b]pyridin-4(5H)-yl)ethyl)-7-methoxy-[1,2,4]triazolo[1,5-c]quinazolin-5-amine;

2-(2-(5,6-dihydropyrido[3,4-d]pyrimidin-7(8H)-yl)ethyl)-7-methoxy-[1,2,4]triazolo[1,5-c]quinazolin-5-amine;

2-(2-(7,8-dihydropyrido[4,3-d]pyrimidin-6(5H)-yl)ethyl)-7-methoxy-[1,2,4]triazolo[1,5-c]quinazolin-5-amine;

2-(2-(7,8-dihydropyrido[4,3-b]pyrazin-6(5H)-yl)ethyl)-7-methoxy-[1,2,4]triazolo[1,5-c]quinazolin-5-amine;

2-(2-(6,7-dihydrothiazolo[5,4-c]pyridin-5(4H)-yl)ethyl)-7-methoxy-[1,2,4]triazolo[1,5-c]quinazolin-5-amine;

2-(2-(6,7-dihydrothiazolo[4,5-c]pyridin-5(4H)-yl)ethyl)-7-methoxy-[1,2,4]triazolo[1,5-c]quinazolin-5-amine;

7-methoxy-2-(2-(2-(trifluoromethyl)-5,6-dihydroimidazo[1,2-a]pyrazin-7(8H)-yl)ethyl)-[1,2,4]triazolo[1,5-c]quinazolin-5-amine;

2-(2-(6,7-dihydropyrazolo[1,5-a]pyrimidin-4(5H)-yl)ethyl)-7-methoxy-[1,2,4]triazolo[1,5-c]quinazolin-5-amine;

7-methoxy-2-(2-(2-methyl-7,8-dihydro-4H-pyrazolo[1,5-a][1,4]diazepin-5(6H)-yl)ethyl)-[1,2,4]triazolo[1,5-c]quinazolin-5-amine;

5-(2-(5-amino-7-methoxy-[1,2,4]triazolo[1,5-c]quinazolin-2-yl)ethyl)-5,6,7,8-tetrahydro-4H-pyrazolo[1,5-a][1,4]diazepine-2-carbonitrile;

2-(2-(4,4-dimethyl-3,4-dihydroisoquinolin-2(1H)-yl)ethyl)-7-methoxy-[1,2,4]triazolo[1,5-c]quinazolin-5-amine;

7-methoxy-2-(2-(2-(4-methylpiperazin-1-yl)-5H-pyrrolo[3,4-b]pyridin-6(7H)-yl)ethyl)-[1,2,4]triazolo[1,5-c]quinazolin-5-amine;

7-methoxy-2-(2-(2-morpholino-5H-pyrrolo[3,4-b]pyridin-6(7H)-yl)ethyl)-[1,2,4]triazolo[1,5-c]quinazolin-5-amine;

7-methoxy-2-(2-(2-(pyrrolidin-1-yl)-5H-pyrrolo[3,4-b]pyridin-6(7H)-yl)ethyl)-[1,2,4]triazolo[1,5-c]quinazolin-5-amine;

2-(2-(2-(4-ethylpiperazin-1-yl)-5H-pyrrolo[3,4-b]pyridin-6(7H)-yl)ethyl)-7-methoxy-[1,2,4]triazolo[1,5-c]quinazolin-5-amine;

2-(2-(2-(2,2-dimethylmorpholino)-5H-pyrrolo[3,4-b]pyridin-6(7H)-yl)ethyl)-7-methoxy-[1,2,4]triazolo[1,5-c]quinazolin-5-amine;

2-(2-(2-((2S,6R)-2,6-dimethylmorpholino)-5H-pyrrolo[3,4-b]pyridin-6(7H)-yl)ethyl)-7-methoxy-[1,2,4]triazolo[1,5-c]quinazolin-5-amine;

2-(2-(2-(4-(cyclopropylmethyl)piperazin-1-yl)-5H-pyrrolo[3,4-b]pyridin-6(7H)-yl)ethyl)-7-methoxy-[1,2,4]triazolo[1,5-c]quinazolin-5-amine;

2-(2-(2-(4-(4-fluorophenyl)piperazin-1-yl)-5H-pyrrolo[3,4-b]pyridin-6(7H)-yl)ethyl)-7-methoxy-[1,2,4]triazolo[1,5-c]quinazolin-5-amine;

7-methoxy-2-(2-(2-(4-morpholinopiperidin-1-yl)-5H-pyrrolo[3,4-b]pyridin-6(7H)-yl)ethyl)-[1,2,4]triazolo[1,5-c]quinazolin-5-amine;

2-(2-(4-(4-ethylpiperazin-1-yl)-5,6-dihydro-1,7-naphthyridin-7(8H)-yl)ethyl)-7-methoxy-[1,2,4]triazolo[1,5-c]quinazolin-5-amine;

2-(2-(4-(diethylamino)-5,6-dihydro-1,7-naphthyridin-7(8H)-yl)ethyl)-7-methoxy-[1,2,4]triazolo[1,5-c]quinazolin-5-amine;

2-(2-(4-(3,3-difluoropyrrolidin-1-yl)-5,6-dihydro-1,7-naphthyridin-7(8H)-yl)ethyl)-7-methoxy-[1,2,4]triazolo[1,5-c]quinazolin-5-amine;

2-(5-amino-7-methoxy-[1,2,4]triazolo[1,5-c]quinazolin-2-yl)-1-(5H-pyrrolo[3,4-b]pyridin-6(7H)-yl)ethanone;

2-(5-amino-7-methoxy-[1,2,4]triazolo[1,5-c]quinazolin-2-yl)-1-(4,5-dihydro-1H-benzo[d]azepin-3(2H)-yl)ethanone;

2-(2-(5H-pyrrolo[3,4-b]pyridin-6(7H)-yl)ethyl)-7-(fluoromethoxy)-[1,2,4]triazolo[1,5-c]quinazolin-5-amine;

7-chloro-2-(2-(5-fluoroisoindolin-2-yl)ethyl)-[1,2,4]triazolo[1,5-c]quinazolin-5-amine;

7-chloro-2-(2-(3,4-dihydroquinolin-1(2H)-yl)ethyl)-[1,2,4]triazolo[1,5-c]quinazolin-5-amine;

2-[2-(5,7-dihydro-6H-pyrrolo[3,4-b]pyridin-6-yl)ethyl]-7-fluoro[1,2,4]triazolo[1,5-c]quinazolin-5-amine;

2-(2-(3,4-dihydroquinolin-1(2H)-yl)ethyl)-7-fluoro-[1,2,4]triazolo[1,5-c]quinazolin-5-amine;

7-fluoro-2-(2-(5-fluoroisoindolin-2-yl)ethyl)-[1,2,4]triazolo[1,5-c]quinazolin-5-amine;

2-(2-(3-ethyl-5,6-dihydro-[1,2,4]triazolo[4,3-a]pyrazin-7(8H)-yl)ethyl)-7-fluoro-[1,2,4]triazolo[1,5-c]quinazolin-5-amine;

2-(2-(3,4-dihydroisoquinolin-2(1H)-yl)ethyl)-7-fluoro-[1,2,4]triazolo[1,5-c]quinazolin-5-amine;

7-fluoro-2-(2-(2-(trifluoromethyl)-5H-pyrrolo[3,4-d]pyrimidin-6(7H)-yl)ethyl)-[1,2,4]triazolo[1,5-c]quinazolin-5-amine;

7-fluoro-2-(2-(4-fluoroisoindolin-2-yl)ethyl)-[1,2,4]triazolo[1,5-c]quinazolin-5-amine;

2-(2-(3,4-dihydroisoquinolin-2(1H)-yl)ethyl)-7-methyl-[1,2,4]triazolo[1,5-c]quinazolin-5-amine;

8-fluoro-2-(2-(5-fluoroisoindolin-2-yl)ethyl)-[1,2,4]triazolo[1,5-c]quinazolin-5-amine;

2-(2-(5H-pyrrolo[3,4-b]pyridin-6(7H)-yl)ethyl)-8-fluoro-[1,2,4]triazolo[1,5-c]quinazolin-5-amine;

2-(2-(3,4-dihydroisoquinolin-2(1H)-yl)ethyl)-8-fluoro-[1,2,4]triazolo[1,5-c]quinazolin-5-amine;

2-(2-(3,4-dihydroquinolin-1(2H)-yl)ethyl)-8-fluoro-[1,2,4]triazolo[1,5-c]quinazolin-5-amine;

2-(2-(3-ethyl-5,6-dihydro-[1,2,4]triazolo[4,3-a]pyrazin-7(8H)-yl)ethyl)-8-fluoro-[1,2,4]triazolo[1,5-c]quinazolin-5-amine;
8-fluoro-2-(2-(4-fluoroisoindolin-2-yl)ethyl)-[1,2,4]triazolo[1,5-c]quinazolin-5-amine;
2-(2-(5H-pyrrolo[3,4-b]pyridin-6(7H)-yl)ethyl)-7,8-dimethoxy-[1,2,4]triazolo[1,5-c]quinazolin-5-amine;
2-(2-(5H-pyrrolo[3,4-b]pyridin-6(7H)-yl)ethyl)-9-fluoro-7-methoxy-[1,2,4]triazolo[1,5-c]quinazolin-5-amine;
2-(2-(5H-pyrrolo[3,4-b]pyridin-6(7H)-yl)ethyl)-8,9-difluoro-[1,2,4]triazolo[1,5-c]quinazolin-5-amine;
2-(2-(5H-pyrrolo[3,4-b]pyridin-6(7H)-yl)ethyl)-7,9-difluoro-[1,2,4]triazolo[1,5-c]quinazolin-5-amine;
2-(3,3-difluoro-2-(5H-pyrrolo[3,4-b]pyridin-6(7H)-yl)propyl)-7-methoxy-[1,2,4]triazolo[1,5-c]quinazolin-5-amine;
(R)-2-(3,3-difluoro-2-(5H-pyrrolo[3,4-b]pyridin-6(7H)-yl)propyl)-7-methoxy-[1,2,4]triazolo[1,5-c]quinazolin-5-amine;
(S)-2-(3,3-difluoro-2-(5H-pyrrolo[3,4-b]pyridin-6(7H)-yl)propyl)-7-methoxy-[1,2,4]triazolo[1,5-c]quinazolin-5-amine;
2-(3-fluoro-2-(5H-pyrrolo[3,4-b]pyridin-6(7H)-yl)propyl)-7-methoxy-[1,2,4]triazolo[1,5-c]quinazolin-5-amine;
2-(2-(5H-pyrrolo[3,4-b]pyridin-6(7H)-yl)propyl)-7-methoxy-[1,2,4]triazolo[1,5-c]quinazolin-5-amine;
(S)-2-(2-(5H-pyrrolo[3,4-b]pyridin-6(7H)-yl)propyl)-7-methoxy-[1,2,4]triazolo[1,5-c]quinazolin-5-amine;
(R)-2-(2-(5H-pyrrolo[3,4-b]pyridin-6(7H)-yl)propyl)-7-methoxy-[1,2,4]triazolo[1,5-c]quinazolin-5-amine;
7-methoxy-2-(3,3,3-trifluoro-2-(5H-pyrrolo[3,4-b]pyridin-6(7H)-yl)propyl)-[1,2,4]triazolo[1,5-c]quinazolin-5-amine;
(S)-7-methoxy-2-(3,3,3-trifluoro-2-(5H-pyrrolo[3,4-b]pyridin-6(7H)-yl)propyl)-[1,2,4]triazolo[1,5-c]quinazolin-5-amine;
(R)-7-methoxy-2-(3,3,3-trifluoro-2-(5H-pyrrolo[3,4-b]pyridin-6(7H)-yl)propyl)-[1,2,4]triazolo[1,5-c]quinazolin-5-amine;
2-(2-(5H-pyrrolo[3,4-b]pyridin-6(7H)-yl)butyl)-7-methoxy-[1,2,4]triazolo[1,5-c]quinazolin-5-amine;
(R)-2-(2-(5H-pyrrolo[3,4-b]pyridin-6(7H)-yl)butyl)-7-methoxy-[1,2,4]triazolo[1,5-c]quinazolin-5-amine;
(S)-2-(2-(5H-pyrrolo[3,4-b]pyridin-6(7H)-yl)butyl)-7-methoxy-[1,2,4]triazolo[1,5-c]quinazolin-5-amine;
2-(2-(5-fluoroisoindolin-2-yl)propyl)-7-methoxy-[1,2,4]triazolo[1,5-c]quinazolin-5-amine;
2-(2-(5H-pyrrolo[3,4-b]pyridin-6(7H)-yl)pentyl)-7-methoxy-[1,2,4]triazolo[1,5-c]quinazolin-5-amine;
7-methoxy-2-(2-(2-methyl-6,7-dihydrooxazolo[5,4-c]pyridin-5(4H)-yl)propyl)-[1,2,4]triazolo[1,5-c]quinazolin-5-amine;
2-((5-fluoroisoindolin-2-yl)methyl)-7-methoxy-[1,2,4]triazolo[1,5-c]quinazolin-5-amine;
2-((5H-pyrrolo[3,4-b]pyridin-6(7H)-yl)methyl)-7-methoxy-[1,2,4]triazolo[1,5-c]quinazolin-5-amine;
2-((3,4-dihydroquinolin-1(2H)-yl)methyl)-7-methoxy-[1,2,4]triazolo[1,5-c]quinazolin-5-amine;
2-((2H-benzo[b][1,4]oxazin-4(3H)-yl)methyl)-7-methoxy-[1,2,4]triazolo[1,5-c]quinazolin-5-amine;
2-((3,4-dihydroisoquinolin-2(1H)-yl)methyl)-7-methoxy-[1,2,4]triazolo[1,5-c]quinazolin-5-amine;
2-((5-amino-7-methoxy-[1,2,4]triazolo[1,5-c]quinazolin-2-yl)methyl)-1,2,3,4-tetrahydroisoquinoline-6-carbonitrile;
2-((5,6-dihydro-1,7-naphthyridin-7(8H)-yl)methyl)-7-methoxy-[1,2,4]triazolo[1,5-c]quinazolin-5-amine;
7-methoxy-2-((7-methoxy-4,5-dihydro-1H-benzo[d]azepin-3(2H)-yl)methyl)-[1,2,4]triazolo[1,5-c]quinazolin-5-amine;
2-((3,4-dihydro-2,7-naphthyridin-2(1H)-yl)methyl)-7-methoxy-[1,2,4]triazolo[1,5-c]quinazolin-5-amine;
7-methoxy-2-((8-((4-(pyridin-2-yl)piperazin-1-yl)methyl)-3,4-dihydroisoquinolin-2(1H)-yl)methyl)-[1,2,4]triazolo[1,5-c]quinazolin-5-amine;
7-methoxy-2-(2-(2-(trifluoromethyl)isoindolin-2-yl)methyl)-[1,2,4]triazolo[1,5-c]quinazolin-5-amine;
7-methoxy-2-((2,3,4,5-tetrahydro-1H-benzo[b]azepin-1-yl)methyl)-[1,2,4]triazolo[1,5-c]quinazolin-5-amine;
7-methoxy-2-((3-(trifluoromethyl)-7,8-dihydro-1,6-naphthyridin-6(5H)-yl)methyl)-[1,2,4]triazolo[1,5-c]quinazolin-5-amine;
2-((6-fluoro-3,4-dihydroisoquinolin-2(1H)-yl)methyl)-7-methoxy-[1,2,4]triazolo[1,5-c]quinazolin-5-amine;
2-((4,5-dihydro-1H-benzo[d]azepin-3(2H)-yl)methyl)-7-methoxy-[1,2,4]triazolo[1,5-c]quinazolin-5-amine;
2-((4,5-dihydro-1H-benzo[c]azepin-2(3H)-yl)methyl)-7-methoxy-[1,2,4]triazolo[1,5-c]quinazolin-5-amine;
2-((3,4-dihydro-1,5-naphthyridin-1(2H)-yl)methyl)-7-methoxy-[1,2,4]triazolo[1,5-c]quinazolin-5-amine;
2-((3,4-dihydro-1,6-naphthyridin-1(2H)-yl)methyl)-7-methoxy-[1,2,4]triazolo[1,5-c]quinazolin-5-amine;
2-((3,4-dihydro-1,7-naphthyridin-1(2H)-yl)methyl)-7-methoxy-[1,2,4]triazolo[1,5-c]quinazolin-5-amine;
2-((7-chloro-4-methyl-2,3,4,5-tetrahydro-1H-benzo[e][1,4]diazepin-1-yl)methyl)-7-methoxy-[1,2,4]triazolo[1,5-c]quinazolin-5-amine;
2-((2-chloro-5H-pyrrolo[3,4-b]pyridin-6(7H)-yl)methyl)-7-methoxy-[1,2,4]triazolo[1,5-c]quinazolin-5-amine;
7-methoxy-2-((3-(methylthio)-5,6-dihydro-[1,2,4]triazolo[4,3-a]pyrazin-7(8H)-yl)methyl)-[1,2,4]triazolo[1,5-c]quinazolin-5-amine;
ethyl 7-((5-amino-7-methoxy-[1,2,4]triazolo[1,5-c]quinazolin-2-yl)methyl)-5,6,7,8-tetrahydro-[1,2,4]triazolo[4,3-a]pyrazine-3-carboxylate;
2-((3-bromo-5,6-dihydro-[1,2,4]triazolo[4,3-a]pyrazin-7(8H)-yl)methyl)-7-methoxy-[1,2,4]triazolo[1,5-c]quinazolin-5-amine;
2-((5,6-dihydro-[1,2,4]triazolo[4,3-a]pyrazin-7(8H)-yl)methyl)-7-methoxy-[1,2,4]triazolo[1,5-c]quinazolin-5-amine;
2-((3-ethyl-5,6-dihydro-[1,2,4]triazolo[4,3-a]pyrazin-7(8H)-yl)methyl)-7-methoxy-[1,2,4]triazolo[1,5-c]quinazolin-5-amine;
7-((5-amino-7-methoxy-[1,2,4]triazolo[1,5-c]quinazolin-2-yl)methyl)-N-tert-butyl-5,6,7,8-tetrahydro-[1,2,4]triazolo[4,3-a]pyrazine-3-carboxamide;
7-methoxy-2-((3-methoxy-5,6-dihydro-[1,2,4]triazolo[4,3-a]pyrazin-7(8H)-yl)methyl)-[1,2,4]triazolo[1,5-c]quinazolin-5-amine;
2-((5,5-dimethyl-3-(trifluoromethyl)-5,6-dihydro-[1,2,4]triazolo[4,3-a]pyrazin-7(8H)-yl)methyl)-7-methoxy-[1,2,4]triazolo[1,5-c]quinazolin-5-amine;
2-((8,8-dimethyl-3-(trifluoromethyl)-5,6-dihydro-[1,2,4]triazolo[4,3-a]pyrazin-7(8H)-yl)methyl)-7-methoxy-[1,2,4]triazolo[1,5-c]quinazolin-5-amine;
2-((4-bromo-5,6-dihydro-1,7-naphthyridin-7(8H)-yl)methyl)-7-methoxy-[1,2,4]triazolo[1,5-c]quinazolin-5-amine;
2-((7,8-dihydropyrido[4,3-b]pyrazin-6(5H)-yl)methyl)-7-methoxy-[1,2,4]triazolo[1,5-c]quinazolin-5-amine;

2-((5,6-dihydropyrido[3,4-d]pyrimidin-7(8H)-yl)methyl)-7-methoxy-[1,2,4]triazolo[1,5-c]quinazolin-5-amine;
7-methoxy-2-((2-(trifluoromethyl)-5H-pyrrolo[3,4-d]pyrimidin-6(7H)-yl)methyl)-[1,2,4]triazolo[1,5-c]quinazolin-5-amine;
7-methoxy-2-((3-(trifluoromethyl)-5,6-dihydro-[1,2,4]triazolo[4,3-a]pyrazin-7(8H)-yl)methyl)-[1,2,4]triazolo[1,5-c]quinazolin-5-amine;
2-((2,3-dihydro-1H-pyrrolo[2,3-b]pyridin-1-yl)methyl)-7-methoxy-[1,2,4]triazolo[1,5-c]quinazolin-5-amine;
2-((5-bromo-2,3-dihydro-1H-pyrrolo[2,3-b]pyridin-1-yl)methyl)-7-methoxy-[1,2,4]triazolo[1,5-c]quinazolin-5-amine;
7-methoxy-2-((7-methyl-3,4-dihydro-1,8-naphthyridin-1(2H)-yl)methyl)-[1,2,4]triazolo[1,5-c]quinazolin-5-amine;
2-((7,8-dihydro-5H-pyrido[2,3-b]azepin-9(6H)-yl)methyl)-7-methoxy-[1,2,4]triazolo[1,5-c]quinazolin-5-amine;
2-((2,3-dihydro-1H-pyrrolo[2,3-b]pyridin-1-yl)methyl)-7-methoxy-[1,2,4]triazolo[1,5-c]quinazolin-5-amine;
2-((2-chloro-7,8-dihydro-5H-pyrido[2,3-b]azepin-9(6H)-yl)methyl)-7-methoxy-[1,2,4]triazolo[1,5-c]quinazolin-5-amine;
2-((3,4-dihydro-1,8-naphthyridin-1(2H)-yl)methyl)-7-methoxy-[1,2,4]triazolo[1,5-c]quinazolin-5-amine;
7-methoxy-2-((2-(pyridin-2-yl)-7,8-dihydro-5H-pyrido[2,3-b]azepin-9(6H)-yl)methyl)-[1,2,4]triazolo[1,5-c]quinazolin-5-amine;
2-((4,4-dimethyl-3,4-dihydroisoquinolin-2(1H)-yl)methyl)-7-methoxy-[1,2,4]triazolo[1,5-c]quinazolin-5-amine;
2-((5H-pyrrolo[3,4-b]pyridin-6(7H)-yl)methyl)-9-fluoro-7-methoxy-[1,2,4]triazolo[1,5-c]quinazolin-5-amine;
7-methoxy-2-((7-(pyrimidin-5-yl)-3,4-dihydroisoquinolin-2(1H)-yl)methyl)-[1,2,4]triazolo[1,5-c]quinazolin-5-amine;
N-(2-((5-amino-7-methoxy-[1,2,4]triazolo[1,5-c]quinazolin-2-yl)methyl)-1,2,3,4-tetrahydroisoquinolin-7-yl)picolinamide;
N-(2-((5-amino-7-methoxy-[1,2,4]triazolo[1,5-c]quinazolin-2-yl)methyl)-1,2,3,4-tetrahydroisoquinolin-7-yl)acetamide;
2-((7-(3,4-difluorophenyl)-3,4-dihydroisoquinolin-2(1H)-yl)methyl)-7-methoxy-[1,2,4]triazolo[1,5-c]quinazolin-5-amine;
7-methoxy-2-(2-(7-(pyrimidin-5-yl)-3,4-dihydroisoquinolin-2(1H)-yl)ethyl)-[1,2,4]triazolo[1,5-c]quinazolin-5-amine;
2-(2-((5-amino-7-methoxy-[1,2,4]triazolo[1,5-c]quinazolin-2-yl)methyl)-1,2,3,4-tetrahydroisoquinolin-7-yl)-N-(pyridine-3-yl)acetamide;
7-methoxy-2-((5-(pyrimidin-5-yl)isoindolin-2-yl)methyl)-[1,2,4]triazolo[1,5-c]quinazolin-5-amine;
7-methoxy-2-((8-(pyrimidin-5-yl)-3,4-dihydroisoquinolin-2(1H)-yl)methyl)-[1,2,4]triazolo[1,5-c]quinazolin-5-amine;
7-methoxy-2-((7-(2-(trifluoromethyl)pyrimidin-5-yl)-3,4-dihydroisoquinolin-2(1H)-yl)methyl)-[1,2,4]triazolo[1,5-c]quinazolin-5-amine;
7-methoxy-2-((7-(1-methyl-1H-pyrazol-4-yl)-3,4-dihydroisoquinolin-2(1H)-yl)methyl)-[1,2,4]triazolo[1,5-c]quinazolin-5-amine;
7-methoxy-2-((7-(1-methyl-5-(trifluoromethyl)-1H-pyrazol-4-yl)-3,4-dihydroisoquinolin-2(1H)-yl)methyl)-[1,2,4]triazolo[1,5-c]quinazolin-5-amine;
7-methoxy-2-((7-(1-methyl-3-(trifluoromethyl)-1H-pyrazol-4-yl)-3,4-dihydroisoquinolin-2(1H)-yl)methyl)-[1,2,4]triazolo[1,5-c]quinazolin-5-amine;
7-methoxy-2-((7-(2-(trifluoromethyl)phenyl)-3,4-dihydroisoquinolin-2(1H)-yl)methyl)-[1,2,4]triazolo[1,5-c]quinazolin-5-amine;
2-((7-(2-amino-4-(trifluoromethyl)pyrimidin-5-yl)-3,4-dihydroisoquinolin-2(1H)-yl)methyl)-7-methoxy-[1,2,4]triazolo[1,5-c]quinazolin-5-amine;
7-methoxy-2-(2-(7-(2-(trifluoromethyl)pyrimidin-5-yl)-3,4-dihydroisoquinolin-2(1H)-yl)ethyl)-[1,2,4]triazolo[1,5-c]quinazolin-5-amine;
7-bromo-2-((5,6-dihydro-1,7-naphthyridin-7(8H)-yl)methyl)-[1,2,4]triazolo[1,5-c]quinazolin-5-amine;
2-((5H-pyrrolo[3,4-b]pyridin-6(7H)-yl)methyl)-7-bromo-[1,2,4]triazolo[1,5-c]quinazolin-5-amine;
5-amino-2-((5,6-dihydro-1,7-naphthyridin-7(8H)-yl)methyl)-[1,2,4]triazolo[1,5-c]quinazoline-7-carbonitrile;
2-((5H-pyrrolo[3,4-b]pyridin-6(7H)-yl)methyl)-5-amino-[1,2,4]triazolo[1,5-c]quinazoline-7-carbonitrile;
2-((5H-pyrrolo[3,4-b]pyridin-6(7H)-yl)methyl)-7-(methoxymethyl)-[1,2,4]triazolo[1,5-c]quinazolin-5-amine;
2-((5,6-dihydro-1,7-naphthyridin-7(8H)-yl)methyl)-7-(methoxymethyl)-[1,2,4]triazolo[1,5-c]quinazolin-5-amine;
2-((5H-pyrrolo[3,4-b]pyridin-6(7H)-yl)methyl)-7-methyl-[1,2,4]triazolo[1,5-c]quinazolin-5-amine;
2-((5,6-dihydro-1,7-naphthyridin-7(8H)-yl)methyl)-7-methyl-[1,2,4]triazolo[1,5-c]quinazolin-5-amine;
2-((5,6-dihydro-1,7-naphthyridin-7(8H)-yl)methyl)-7-(2-fluoroethoxy)-[1,2,4]triazolo[1,5-c]quinazolin-5-amine;
2-((5H-pyrrolo[3,4-b]pyridin-6(7H)-yl)methyl)-7-ethoxy-[1,2,4]triazolo[1,5-c]quinazolin-5-amine;
2-((5,6-dihydro-1,7-naphthyridin-7(8H)-yl)methyl)-7-ethoxy-[1,2,4]triazolo[1,5-c]quinazolin-5-amine;
2-((5,6-dihydro-1,7-naphthyridin-7(8H)-yl)methyl)-7-(fluoromethoxy)-[1,2,4]triazolo[1,5-c]quinazolin-5-amine;
(R)-7-methoxy-2-(2-(2-methyl-6,7-dihydrooxazolo[5,4-c]pyridin-5(4H)-yl)propyl)-[1,2,4]triazolo[1,5-c]quinazolin-5-amine;
(S)-7-methoxy-2-(2-(2-methyl-6,7-dihydrooxazolo[5,4-c]pyridin-5(4H)-yl)propyl)-[1,2,4]triazolo[1,5-c]quinazolin-5-amine;
7-methoxy-2-(2-(2-methyl-6,7-dihydrooxazolo[4,5-c]pyridin-5(4H)-yl)propyl)-[1,2,4]triazolo[1,5-c]quinazolin-5-amine;
(R)-7-methoxy-2-(2-(2-methyl-6,7-dihydrooxazolo[4,5-c]pyridin-5(4H)-yl)propyl)-[1,2,4]triazolo[1,5-c]quinazolin-5-amine;
(S)-7-methoxy-2-(2-(2-methyl-6,7-dihydrooxazolo[4,5-c]pyridin-5(4H)-yl)propyl)-[1,2,4]triazolo[1,5-c]quinazolin-5-amine;
(R)-7-methoxy-2-(2-(2-methyl-6,7-dihydrothiazolo[5,4-c]pyridin-5(4H)-yl)propyl)-[1,2,4]triazolo[1,5-c]quinazolin-5-amine;
(S)-7-methoxy-2-(2-(2-methyl-6,7-dihydrothiazolo[5,4-c]pyridin-5(4H)-yl)propyl)-[1,2,4]triazolo[1,5-c]quinazolin-5-amine;
(R)-7-methoxy-2-(2-(2-methyl-6,7-dihydrothiazolo[4,5-c]pyridin-5(4H)-yl)propyl)-[1,2,4]triazolo[1,5-c]quinazolin-5-amine;

(S)-7-methoxy-2-(2-(2-methyl-6,7-dihydrothiazolo[4,5-c]pyridin-5(4H)-yl)propyl)-[1,2,4]triazolo[1,5-c]quinazolin-5-amine;
(R)-7-methoxy-2-(2-(2-methyl-6,7-dihydropyrazolo[1,5-a]pyrazin-5(4H)-yl)propyl)-[1,2,4]triazolo[1,5-c]quinazolin-5-amine;
(S)-7-methoxy-2-(2-(2-methyl-6,7-dihydropyrazolo[1,5-a]pyrazin-5(4H)-yl)propyl)-[1,2,4]triazolo[1,5-c]quinazolin-5-amine;
(R)-2-(2-(2-(difluoromethyl)-6,7-dihydropyrazolo[1,5-a]pyrazin-5(4H)-yl)propyl)-7-methoxy-[1,2,4]triazolo[1,5-c]quinazolin-5-amine;
(S)-2-(2-(2-(difluoromethyl)-6,7-dihydropyrazolo[1,5-a]pyrazin-5(4H)-yl)propyl)-7-methoxy-[1,2,4]triazolo[1,5-c]quinazolin-5-amine;
(R)-2-(2-(2-(difluoromethyl)-6,7-dihydrothiazolo[5,4-c]pyridin-5(4H)-yl)propyl)-7-methoxy-[1,2,4]triazolo[1,5-c]quinazolin-5-amine;
(S)-7-methoxy-2-(2-(2-(trifluoromethyl)-6,7-dihydrothiazolo[4,5-c]pyridin-5(4H)-yl) propyl)-[1,2,4]triazolo[1,5-c]quinazolin-5-amine;
2-(3-(5H-pyrrolo[3,4-b]pyridin-6(7H)-yl) propyl)-7-methoxy-[1,2,4]triazolo[1,5-c]quinazolin-5-amine;
2-(3-(4-fluoroisoindolin-2-yl)propyl)-7-methoxy-[1,2,4]triazolo[1,5-c]quinazolin-5-amine;
2-(3-(5-fluoroisoindolin-2-yl)propyl)-7-methoxy-[1,2,4]triazolo[1,5-c]quinazolin-5-amine;
7-methoxy-2-(3-(5-(trifluoromethyl)isoindolin-2-yl)propyl)-[1,2,4]triazolo[1,5-c]quinazolin-5-amine;
7-methoxy-2-(2-(2,7,7-trimethyl-6,7-dihydrooxazolo[5,4-c]pyridin-5(4H)-yl)ethyl)-[1,2,4]triazolo[1,5-c]quinazolin-5-amine;
2-(2-(2,4-dimethyl-6,7-dihydrooxazolo[5,4-c]pyridin-5(4H)-yl)ethyl)-7-methoxy-[1,2,4]triazolo[1,5-c]quinazolin-5-amine;
2-(2-(2,6-dimethyl-6,7-dihydrooxazolo[5,4-c]pyridin-5(4H)-yl)ethyl)-7-methoxy-[1,2,4]triazolo[1,5-c]quinazolin-5-amine; or
7-methoxy-2-(2-(2,7,7-trimethyl-6,7-dihydrothiazolo[5,4-c]pyridin-5(4H)-yl)ethyl)-[1,2,4]triazolo[1,5-c]quinazolin-5-amine, or any of the foregoing in the form of a pharmaceutically acceptable salt.

13. A pharmaceutical composition comprising an inert carrier and a compound of claim 1, or a pharmaceutically acceptable salt thereof.

14. A dosage form comprising the composition of claim 13.

* * * * *